US012509439B2

(12) United States Patent
Guy et al.

(10) Patent No.: US 12,509,439 B2
(45) Date of Patent: Dec. 30, 2025

(54) ANTI-MALARIAL AGENTS

(71) Applicants: UNIVERSITY OF KENTUCKY RESEARCH FOUNDATION, Lexington, KY (US); MMV MEDICINES FOR MALARIA VENTURE, Geneva (CH)

(72) Inventors: Rodney Kiplin Guy, Lexington, KY (US); Jared T. Hammill, Fishers, IN (US); David Floyd, Pennington, NJ (US); Jeremy Burrows, La Rippe (CH); Stephen Brand, Alyth (GB)

(73) Assignees: UNIVERSITY OF KENTUCKY RESEARCH FOUNDATION, Lexington, KY (US); MMV MEDICINES FOR MALARIA VENTURE, Geneva (CH)

( * ) Notice: Subject to any disclaimer, the term of this patent is extended or adjusted under 35 U.S.C. 154(b) by 651 days.

(21) Appl. No.: 17/917,593

(22) PCT Filed: Apr. 8, 2021

(86) PCT No.: PCT/EP2021/059196
§ 371 (c)(1),
(2) Date: Oct. 7, 2022

(87) PCT Pub. No.: WO2021/204952
PCT Pub. Date: Oct. 14, 2021

(65) Prior Publication Data

US 2023/0174503 A1 Jun. 8, 2023

Related U.S. Application Data

(60) Provisional application No. 63/007,385, filed on Apr. 9, 2020.

(30) Foreign Application Priority Data

Apr. 9, 2020 (EP) .................................... 20169099

(51) Int. Cl.
*C07D 401/04* (2006.01)
*A61K 45/06* (2006.01)
*A61P 33/06* (2006.01)

(52) U.S. Cl.
CPC ............ *C07D 401/04* (2013.01); *A61K 45/06* (2013.01); *A61P 33/06* (2018.01)

(58) Field of Classification Search
CPC ............................... C07D 401/04; A61P 33/06
See application file for complete search history.

(56) References Cited

FOREIGN PATENT DOCUMENTS

WO WO 2013/027196 2/2013

OTHER PUBLICATIONS

Written Opinion in International Application No. PCT/EP2021/059196, May 19, 2021, pp. 1-12.

(Continued)

*Primary Examiner* — Andrew D Kosar
*Assistant Examiner* — John D McAnany
(74) *Attorney, Agent, or Firm* — SALIWANCHIK, LLOYD & EISENSCHENK

(57) ABSTRACT

The present invention is related to new derivatives in the manufacture of a medicament for preventing or treating malaria. Specifically, the present invention is related to dihydroisoquinoline derivatives useful for the preparation of a pharmaceutical formulation for the inhibition of malaria parasite proliferation.

20 Claims, 4 Drawing Sheets

(56) References Cited

OTHER PUBLICATIONS

Angulo-Barturen, I. et al. "A Murine Model of falciparum-Malaria by In Vivo Selection of Competent Strains in Non-Myelodepleted Mice Engrafted with Human Erythrocytes" *PLoS ONE*, May 2008, pp. 1-14, vol. 3, No. 5, e2252.
Bennett, T. N. et al. "Novel, Rapid, and Inexpensive Cell-Based Quantification of Antimalarial Drug Efficacy" *Antimicrobial Agents and Chemotherapy*, May 2004, pp. 1807-1810, vol. 48, No. 5.
Burrows J et al. "New developments in anti-malarial target candidate and product profiles" *Malaria Journal*, 2017, pp. 1-29, vol. 16, No. 26.
Dechering, K. et al. "Modelling mosquito infection at natural parasite densities identifies drugs targeting EF2, PI4K or ATP4 as key candidates for interrupting malaria transmission" *Scientific Reports*, published online Dec. 15, 2017, pp. 1-9, vol. 7, No. 17680.
Diarra, A. et al. "In situ calibration and [$H^+$] sensitivity of the fluorescent $Na^+$indicator SBFI" *Am J Physiol Cell Physiol*, Jan. 18, 2001, pp. C1623-C1633, vol. 280, No. 6.
Floyd, D. M. et al. "Hit-to-Lead Studies for the Antimalarial Tetrahydroisoquinolone Carboxanilides" *Journal of Medicinal Chemistry*, Aug. 9, 2016, pp. 7950-7962, vol. 59, No. 17.
Gaur, A. H. et al. "Safety, tolerability, pharmacokinetics, and antimalarial efficacy of a novel Plasmodium falciparum ATP4 inhibitor SJ733: a first-in-human and induced blood-stage malaria phase 1a/b trial" *Lancet Infect Dis*, Apr. 7, 2020, pp. 964-975, vol. 20.
Jiménez-Díaz, M. B. et al. "Improved Model of Malaria Using Plasmodium falciparum Competent Strains and Non-Myelodepleted NOD-scid IL2R$\gamma^{null}$ Mice Engrafted with Human Erythrocytes" *Antimicrobial Agents and Chemotherapy*, Oct. 2009, pp. 4533-4536, vol. 53, No. 10.
Jiménez-Díaz, M. B. et al. "Quantitative Measurement of Plasmodium-Infected Erythrocytes in Murine Models of Malaria by Flow Cytometry Using Bidimensional Assessment of SYTO-16 Fluorescence" *Cytometry Part A*, published online Sep. 10, 2008, pp. 225-235, vol. 75A.
Jiménez-Díaz, M. B. et al. "A New In Vivo Screening Paradigm to Accelerate Antimalarial Drug Delivery" *PLoS ONE*, Jun. 25, 2013, pp. 1-12, vol. 8, Issue 6, e66967.
Liu, J. et al. "N-Methylimidazole Promotes the Reaction of Homophthalic Anhydride with Imines" *The Journal of Organic Chemistry*, Jul. 18, 2014, pp. 7593-7599, vol. 79, No. 16.
Mischlinger, J. et al. "Single dose treatment of malaria—current status and perspectives" *Expert Review of Anti-infective Therapy*, Jun. 2, 2016, pp. 1-32.
Rosling, J. E. O. et al. "Biochemical characterization and chemical inhibition of PfATP4-associated $NA^+$-ATPase activity in Plasmodium falciparum membranes" *J. Biol. Chem.*, 2018, pp. 13327-13337, vol. 293, No. 34.
Sakamoto, Y. et al. "Structural and mutational analyses of dipeptidyl peptidase 11 from Porphyromonas gingivalis reveal the molecular basis for strict substrate specificity" *Scientific Reports*, Jun. 9, 2015, pp. 1-16, vol. 5, No. 11151.
Stone, W. J. R. et al. "A Scalable Assessment of Plasmodium falciparum Transmission in the Standard Membrane-Feeding Assay, Using Transgenic Parasites Expressing Green Fluorescent Protein-Lucferase" *The Journal of Infectious Diseases*, Nov. 1, 2014, pp. 1456-1463, vol. 210.
Trager, W. et al. "Human Malaria Parasites in Continuous Culture" *Science*, Aug. 20, 1976, pp. 673-675, vol. 193, No. 4254.
Wells, T. C. et al. "Malaria medicines: a glass half full?" *Nature Reviews Drug Discovery*, published online May 22, 2015, pp. 424-442, vol. 14.

ANTI-MALARIAL AGENTS

CROSS-REFERENCE TO RELATED APPLICATION

This application is the U.S. national stage application of International Patent Application No. PCT/EP2021/059196, filed Apr. 8, 2021.

FIELD OF THE INVENTION

The present invention relates to novel anti-malarial agents. Specifically, the present invention is related to agents useful for the preparation of a pharmaceutical formulation for preventing or treating malaria and methods of their use and manufacture.

BACKGROUND OF THE INVENTION

Malaria is caused by protozoan parasites of the genus *Plasmodium* that infect and destroy red blood cells, leading to fever, severe anemia, cerebral malaria and, if untreated, death. *Plasmodium falciparum*: is the dominant species in sub-Saharan Africa, and is responsible for almost half a million deaths each year. The disease burden is heaviest in African children under 5 years of age and in pregnant women. *Plasmodium vivax* causes 25-40% of the global malaria burden, particularly in South and Southeast Asia, and Central and South America. The other three main species that are known to infect humans are *Plasmodium ovale, Plasmodium malariae* and *Plasmodium knowlesi.*

Malaria is a disease that is prevalent in many developing countries. Approximately 40% of the world's population lives in countries where the disease is endemic; approximately 200 million people suffer from the disease every year.

Various chemical agents have been developed for the treatment and prevention of malaria over the past 20 years (*Malaria medicines: a glass half full*? Wells T. N. et al., 2015, *Nature Reviews Drug Discovery* 14: 424-442). However, many of these medications are costly and some exhibit significant toxicity and undesirable side effects in humans. Drugs used for treating malaria include artemisinin and its derivatives (such as artemether, artesunate or dihydroartemisinin), chloroquine, hydroxychloroquine, quinine, quinidine, mefloquine, amodiaquine, atovaquone/proguanil, clindamycin, doxycycline, lumefantrine, piperaquine, pyronaridine, halofantrine, pyrimethamine-sulfadoxine, primaquine, quinacrine, ferroquine, tafenoquine, arterolane, Spiro[3H-indole-3,1'-[1H]pyrido[3,4-b]indol]-2(1H)-one, 5,7'-dichloro-6'-fluoro-2',3',4',9'-tetrahydro-3'-methyl-,(1'R, 3'S)-] (Cipargamin, KAE609, CAS Registry Number: 1193314-23-6), 2-(1,1-difluoroethyl)-5-methyl-N-[4-(pentafluoro-λ$^6$-sulfanyl)phenyl]-[1,2,4]triazolo[1,5-a] pyrimidin-7-amine (DSM265, CAS Registry Number: 1282041-94-4), Morpholine, 4-[2-(4-cis-dispiro[cyclohexane-1,3'-[1,2,4]trioxolane-5',2''-tricyclo[3.3.1.13,7]decan]-4-ylphenoxy) ethyl]-] (Artefenomel, OZ439, CAS Registry Number: 1029939-86-3), 4-Quinolinecarboxamide, 6-fluoro-2-[4-(4-morpholinylmethyl) phenyl]-N-[2-(1-pyrrolidinyl)ethyl]- (DDD107498, CAS Registry Number: 1469439-69-7), Ethanone, 2-amino-1-[2-(4-fluorophenyl)-3-[(4-fluorophenyl)amino]-5,6-dihydro-8,8-dimethylimidazo[1,2-a]pyrazin-7(8H)-yl]- (Ganaplacide, KAF-156, CAS Registry Number 1261113-96-5), 5-[4-(Methylsulfonyl)phenyl]-6'-(trifluoromethyl)[3,3'-bipyridin]-2-amine (MMV390048, CAS Registry Number: 1314883-11-8), 4(1H)-Quinolinone, 6-chloro-7-methoxy-2-methyl-3-[4-[4-(trifluoromethoxy)phenoxy]phenyl]- (ELQ-300, CAS Registry Number: 1354745-52-0), 4-Isoquinolinecarboxamide, N-(3-cyano-4-fluorophenyl)-1,2,3,4-tetrahydro-1-oxo-3-(3-pyridinyl)-2-(2,2,2-trifluoroethyl)-, (3S,4S)- (SJ-733, CAS Registry Number 1424799-20-1).

Despite increased international efforts for control and ultimate elimination, malaria remains a major health problem. Currently, artemisinin-based combination therapies are the standard treatment for uncomplicated malaria exhibiting high efficacy in sub-Saharan Africa. However, their administration over a three-day period is associated with important problems of treatment adherence resulting in markedly reduced effectiveness under real world settings. Moreover, resistance is emerging against artemesin and the partner drugs. Therefore, in view of the widespread emergence of drug resistance of malaria parasites in endemic countries, there is a continued need for new chemotherapeutic approaches.

It is preferable, and The Malaria Policy Advisory Committee (MPAC) of the World Health Organisation recommends, that new drugs be developed for the treatment of malaria which have the potential for cure following a single dose, for reasons of treatment compliance and ease of use (Single dose treatment of malaria—current status and perspectives. Mischlinger J. et al., 2016, *Expert Rev. Anti. Infect. Ther.,* 14: 669-678). The Medicines for Malaria Venture (MMV) further recommends that the dose which provides cure (i.e. ~$10^{12}$-fold reduction in parasitemia) be ideally less than 100 mg for a 70 Kg person (*New developments in anti-malarial target candidate and product profiles*. Burrows, J. N. et al., 2017, *Malaria J.,* 16: 26).

Phenotypic screening against *Plasmodium falciparum* identified a dihydroisoquinoline series of compounds that exhibits significant potency against the intraerythrocytic stage of malaria via inhibition of the parasite ATP-4'ase, a sodium ion transporter. Optimisation of the series ultimately led to (+)-SJ000557733 (herein referred to as (+) SJ-733) which was progressed into clinical development for malaria. (+) SJ-733 and 58 other examples from the same dihydroisoquinoline series are claimed as antimalarials in WO 2013/027196 (*A New In Vivo Screening Paradigm to Accelerate Antimalarial Drug Discovery*. Jimẽnez-Diaz M. B. et al., 2013, *PLoS ONE* 8(6): e66967).

In phase 1a clinical trials, human pharmacokinetic studies of SJ-733 showed significant formation of an inactive N-oxide metabolite. Subsequent investigation in a phase 1b malaria infection study in human volunteers showed that parasitological cure was not achieved following a single dose of 600 milligrams and that multiple dosing regimens would be required (Gaur et al., 2020, *Lancet Infect Dis.,* 20: 30611-5).

SUMMARY OF THE INVENTION

The present invention is directed towards novel tetrahydroisoquinoline derivatives which are useful in the treatment and/or prophylaxis of malaria, pharmaceutical formulation, use and manufacture thereof. It has been found that those compounds unexpectedly present several advantages over current clinical candidate (+) SJ-733. In particular, it has been found that new compounds of the invention which has similar or improved in-vitro potency present significantly improved metabolic stability compared to (+) SJ-733, imparting confidence that the predicted efficacious single dose in humans will be significantly lower (i.e. <500 mg for a 70 Kg person) and therefore have an additional advantage of improved compliance via reduced is pill burden.

A first aspect of the invention provides a compound according to the invention or a pharmaceutically acceptable salt thereof or a pharmaceutically active derivative thereof.

Another aspect of the invention relates to a compound or a pharmaceutically acceptable salt thereof or a pharmaceutically active derivative thereof according to the invention for use as a medicament.

Another aspect of the invention relates to a compound according to the invention or a pharmaceutically acceptable salt thereof or a pharmaceutically active derivative thereof for use in the prevention and/or treatment of malaria.

Another aspect of the invention relates to the use of a compound according to the invention or a pharmaceutically acceptable salt thereof or a pharmaceutically active derivative thereof for the preparation of a pharmaceutical composition for the prevention and/or treatment of malaria.

Another aspect of the invention resides in a pharmaceutical formulation comprising at least one compound according to the invention or a pharmaceutically acceptable salt thereof or a pharmaceutically active derivative thereof and a pharmaceutically acceptable carrier, diluent or excipient thereof.

Another aspect of the invention resides in a method for preventing and/or treating malaria in a subject. The method comprises administering a compound according to the invention or a pharmaceutically acceptable salt thereof or a pharmaceutically active derivative thereof in a subject in need thereof.

Another aspect of the invention provides a process for the preparation of a compound according to the invention or a pharmaceutically acceptable salt thereof or a pharmaceutically active derivative thereof according to the invention and intermediates thereof.

Another aspect of the invention provides a process for the preparation of a compound of Formula (I).

Another aspect of the invention provides an intermediate of Formula (III) or of Formula (IV-2) or of Formula (V-2) according to the invention.

Another aspect of the invention provides a process of preparation of an intermediate of Formula (III) according to the invention.

Other features and advantages of the invention will be apparent from the following detailed description.

DETAILED DESCRIPTION OF THE INVENTION

Figure 1:
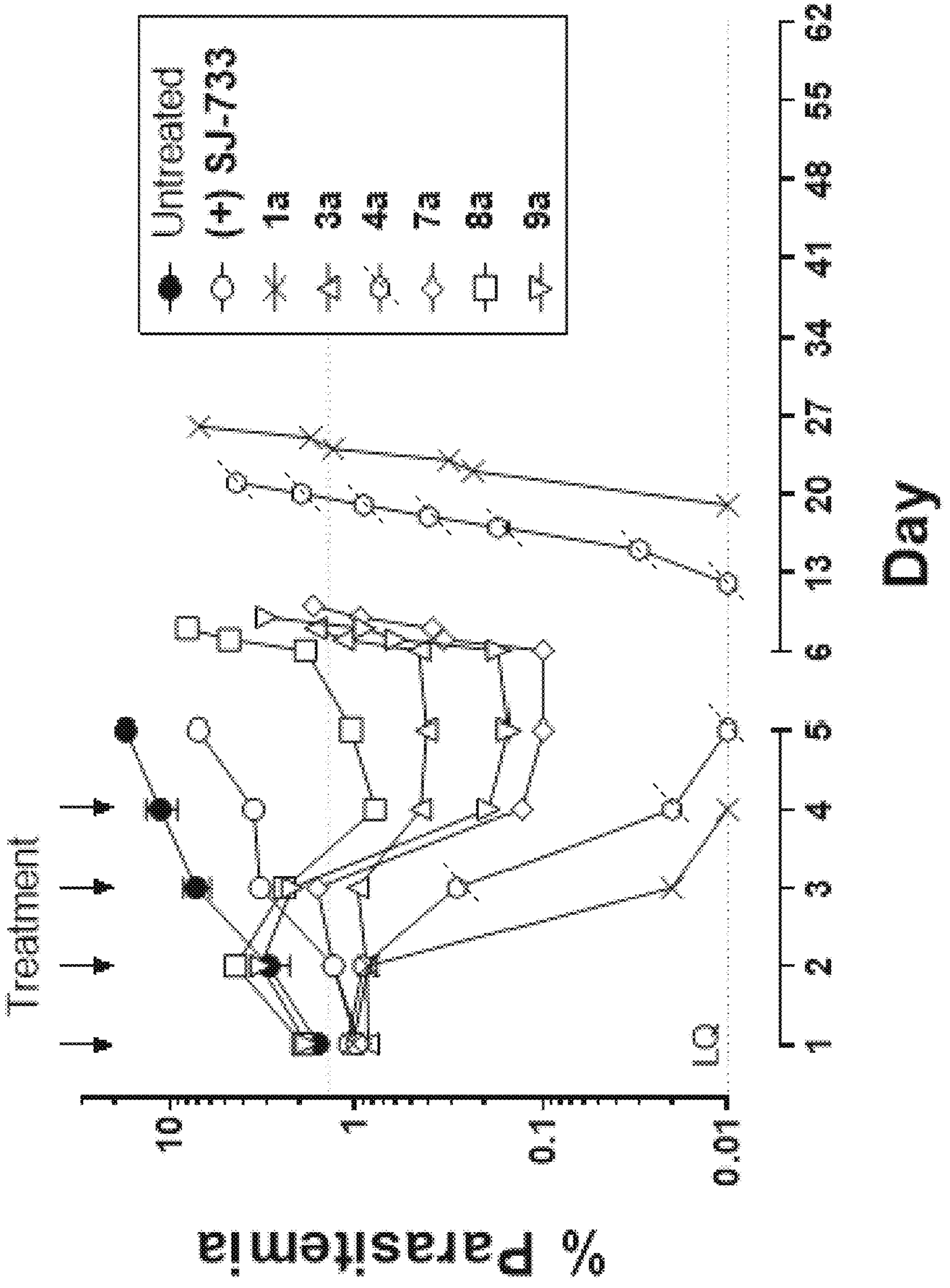
FIG. 1 represents the efficacy of compounds of the invention in a mouse SCID model of malaria, compared with the reference compound (+) SJ-733, as described in Example 3. All compounds were administered orally at a dose of 1 mg/kg b.i.d. for 4 days (arrows).
Figure 2:
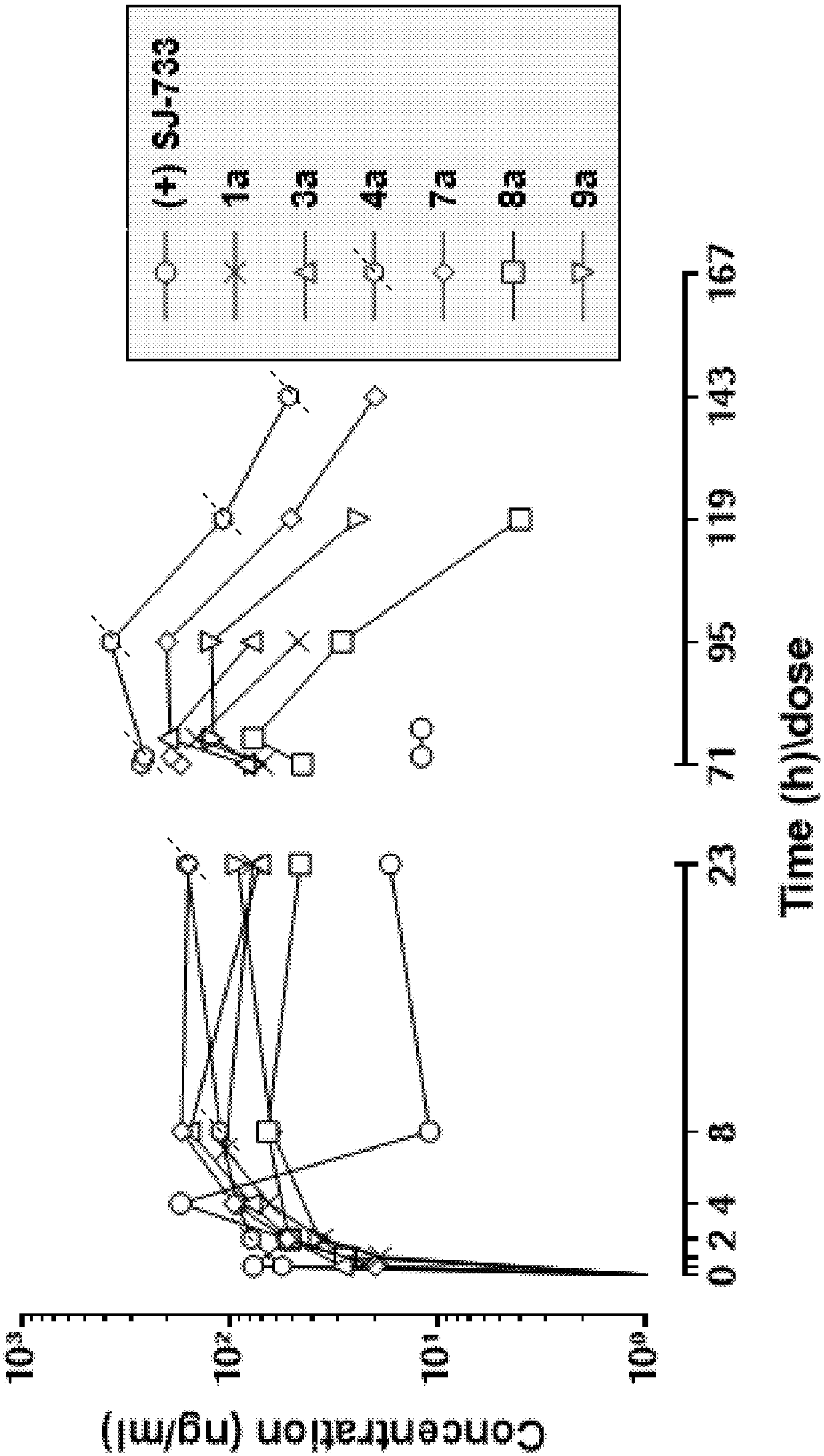
FIG. 2 represents the pharmacokinetic profile of compounds of the invention evaluated in the mouse SCID model of malaria, as described in Example 3, compared with the reference compound (+) SJ-733.
Figure 3:
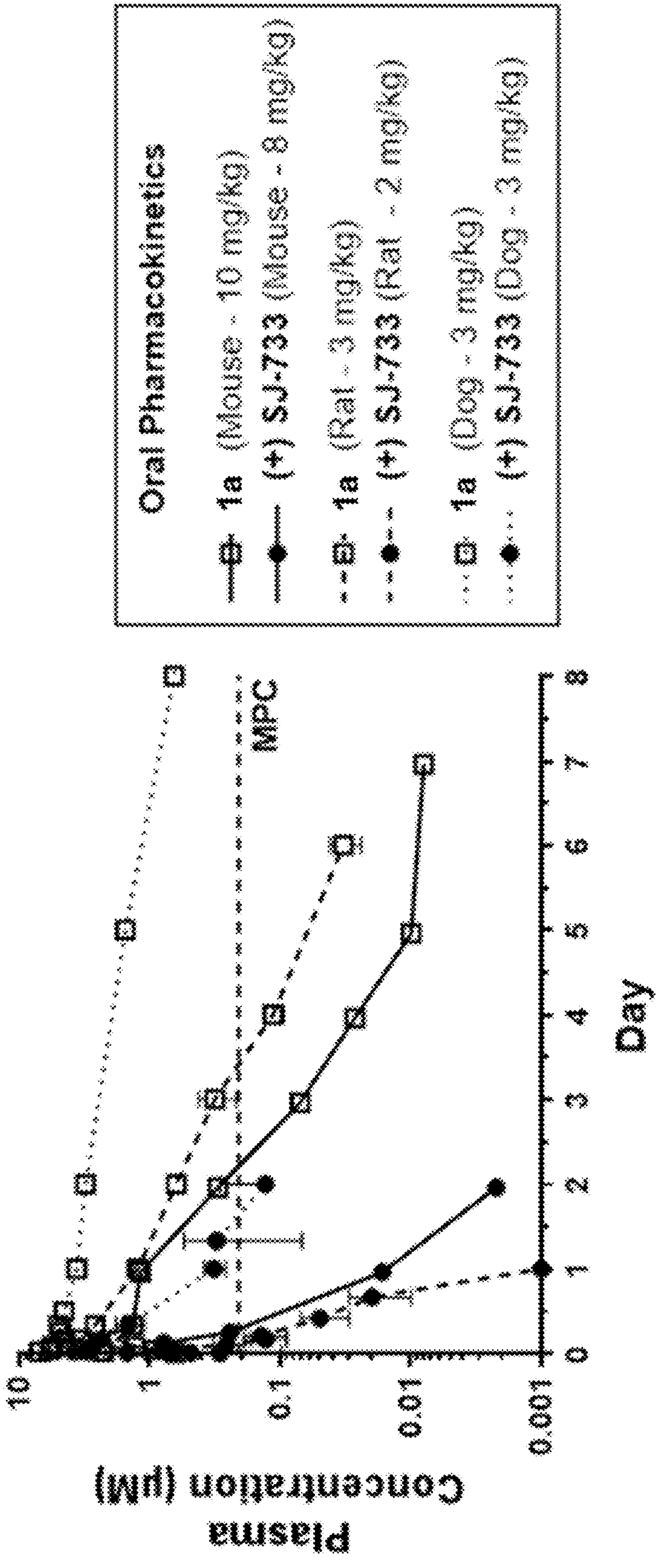
FIG. 3 represents the oral pharmacokinetic profile of compound 1a in mouse, rat and dog species, compared with the reference compound (+) SJ-733.

The following paragraphs provide definitions of the various chemical moieties that make up the compounds according to the invention and are intended to apply uniformly through-out the specification and claims, unless an otherwise expressly set out definition provides a broader definition.

The term "$C_1$-$C_6$ alkyl" when used alone or in combination with other terms, comprises a straight chain or branched $C_1$-$C_6$ alkyl which refers to monovalent alkyl groups having 1 to 6 carbon atoms. This term is exemplified by groups such as methyl, ethyl, n-propyl, i-propyl, n-butyl, s-butyl, i-butyl, t-butyl, n-pentyl, 1-ethylpropyl, 2-methylbutyl, 3-methylbutyl, 2,2-dimethylpropyl, n-hexyl, 2-methylpentyl, 3-methylpentyl, 4-methylpentyl, and the like.

The term "$C_2$-$C_6$ alkenyl" when used alone or in combination with other terms, comprises a straight chain or branched $C_2$-$C_6$ alkenyl. Particularly, it refers to groups having 2 to 6 carbon atoms and having at least 1 or 2 sites of alkenyl unsaturation. It may have any available number of double bonds in any available positions, and the configuration of the double bond may be the (E) or (Z) configuration. This term is exemplified by groups such as vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, and the like. Among others, are vinyl or ethenyl ($—CH═CH_2$), n-2-propenyl (allyl, $—CH_2CH═CH_2$), isopropenyl, 1-propenyl, 2-methyl-1-propenyl, 1-butenyl, 2-butenyl, and 3-methyl-2-butenyl and the like.

The term "$C_2$-$C_6$ alkynyl" when used alone or in combination with other terms, comprises a straight chain or branched $C_2$-$C_6$ alkynyl. It may have any available number of triple bonds in any available positions. This term is exemplified by groups such as alkynyl groups that may have a carbon number of 2-6, and optionally a double bond, such as ethynyl ($—C≡CH$), 1-propynyl, 2-propynyl (propargyl: $—CH_2C≡CH$), 2-butynyl, 2-pentene-4-ynyl, and the like.

The term "heteroalkyl" refers to $C_1$-$C_{12}$-alkyl, preferably $C_1$-$C_6$-alkyl, wherein at least one carbon has been replaced by a heteroatom selected from O, N or S, including 2-methoxy ethyl and the like.

The term "monocyclic aryl" refers to an unsaturated aromatic carbocyclic group of from 6 to 14 carbon atoms having a single ring (e.g. phenyl).

The term "$C_1$-$C_6$ alkyl aryl" refers to aryl groups having a $C_1$-$C_6$ alkyl substituent, including methyl phenyl, ethyl phenyl and the like.

The term "aryl $C_1$-$C_6$ alkyl" refers to $C_1$-$C_6$ alkyl groups having an aryl substituent, including 3-phenylpropanyl, benzyl and the like.

The term "heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, isoquinolinyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido [3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

The term "5-membered heterocycle" refers to a 5-membered heteroaryl or a 5-membered heterocycloalkyl. Examples of those include triazole, pyrazole, triazole, imidazole, and isoxazole.

The term "$C_1$-$C_6$ alkyl heteroaryl" refers to heteroaryl groups having a $C_1$-$C_6$ alkyl substituent, including methyl furyl and the like.

The term "heteroaryl $C_1$-$C_6$ alkyl" refers to $C_1$-$C_6$ alkyl groups having a heteroaryl substituent, including furyl methyl and the like.

The term "$C_2$-$C_6$ alkenyl aryl" refers to an aryl groups having a $C_2$-$C_6$ alkenyl substituent, including vinyl phenyl and the like.

The term "aryl $C_2$-$C_6$ alkenyl" refers to a $C_2$-$C_6$ alkenyl groups having an aryl substituent, including phenyl vinyl and the like.

The term "$C_2$-$C_6$ alkenyl heteroaryl" refers to heteroaryl groups having a $C_2$-$C_6$ alkenyl substituent, including vinyl pyridinyl and the like.

The term "heteroaryl $C_2$-$C_6$ alkenyl" refers to $C_2$-$C_6$ alkenyl groups having a heteroaryl substituent, including pyridinyl vinyl and the like.

The term "$C_3$-$C_8$-cycloalkyl" refers to a saturated carbocyclic group of from 3 to 8 carbon atoms having a single ring (e.g. cyclohexyl) or multiple condensed rings (e.g. norbornyl). $C_3$-$C_8$-cycloalkyl includes cyclopentyl, cyclohexyl, norbornyl and the like.

The term "heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include pyrrolidinyl, piperidinyl, piperazinyl, morpholinyl, tetrahydrofuranyl and the like.

The term "$C_1$-$C_6$ alkyl $C_3$-$C_8$-cycloalkyl" refers to $C_3$-$C_8$-cycloalkyl groups having a $C_1$-$C_6$ alkyl substituent, including methyl cyclopentyl and the like.

The term "$C_3$-$C_8$-cycloalkyl $C_1$-$C_6$ alkyl" refers to $C_1$-$C_6$ alkyl groups having a $C_3$-$C_8$-cycloalkyl substituent, including 3-cyclopentyl propyl and the like.

The term "$C_1$-$C_6$ alkyl heterocycloalkyl" refers to heterocycloalkyl groups having a $C_1$-$C_6$ alkyl substituent, including 4-methylpiperidinyl and the like.

The term "heterocycloalkyl $C_1$-$C_6$ alkyl" refers to $C_1$-$C_6$ alkyl groups having a heterocycloalkyl substituent, including (1-methylpiperidin-4-yl) methyl and the like.

The term "carboxy" refers to the group —C(O)OH.

The term "carboxy $C_1$-$C_6$ alkyl" refers to $C_1$-$C_6$ alkyl groups having a carboxy substituent, including 2-carboxyethyl and the like.

The term "acyl" refers to the group —C(O)R where R includes H, "$C_1$-$C_6$ alkyl," "aryl," "heteroaryl," "$C_3$-$C_8$-cycloalkyl," "heterocycloalkyl," "aryl $C_1$-$C_6$ alkyl," "heteroaryl $C_1$-$C_6$ alkyl," "$C_3$-$C_8$-cycloalkyl $C_1$-$C_6$ alkyl" or "heterocycloalkyl $C_1$-$C_6$ alkyl", including acetyl and the like.

The term "acyl $C_1$-$C_6$ alkyl" to $C_1$-$C_6$ alkyl groups having an acyl substituent, including 2-acetylethyl and the like.

The term "acyl aryl" refers to aryl groups having an acyl substituent, including 2-acetylphenyl and the like.

The term "acyloxy" refers to the group —OC(O)R where R includes H, "$C_1$-$C_6$ alkyl", "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl", including acetyloxy and the like.

The term "acyloxy $C_1$-$C_6$ alkyl" refers to alkyl groups having an acyloxy substituent, including 2-(ethylcarbonyloxy)ethyl and the like.

The term "alkoxy" refers to the group —O—R where R includes optionally substituted "$C_1$-$C_6$ alkyl", optionally substituted "aryl", optionally substituted "heteroaryl", optionally substituted "aryl $C_1$-$C_6$ alkyl" or optionally substituted "heteroaryl $C_1$-$C_6$ alkyl".

The term "alkoxy $C_1$-$C_6$ alkyl" refers to $C_1$-$C_6$ alkyl groups having an alkoxy substituent, including methoxyethyl and the like.

The term "alkoxycarbonyl" refers to the group —C(O)OR where R includes "$C_1$-$C_6$ alkyl", "aryl", "heteroaryl", "aryl $C_1$-$C_6$ alkyl", "heteroaryl $C_1$-$C_6$ alkyl" or "heteroalkyl".

The term "alkoxycarbonyl $C_1$-$C_6$ alkyl" refers to $C_1$-$C_6$ alkyl groups having an alkoxycarbonyl substituent, including 2-(benzyloxycarbonyl)ethyl and the like.

The term "aminocarbonyl" refers to the group —C(O)NRR' where R and R' are independently H, $C_1$-$C_6$ alkyl, aryl, heteroaryl, "aryl $C_1$-$C_6$ alkyl" or "heteroaryl $C_1$-$C_6$ alkyl," including N-phenyl carbonyl and the like.

The term "aminocarbonyl $C_1$-$C_6$ alkyl" refers to $C_1$-$C_6$ alkyl groups having an aminocarbonyl substituent, including 2-(dimethylaminocarbonyl)ethyl, N-ethyl acetamidyl, N,N-Diethyl-acetamidyl and the like.

The term "acylamino" refers to the group —NRC(O)R' where R and R' are independently H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl", including acetylamino and the like.

The term "acylamino $C_1$-$C_6$ alkyl" refers to $C_1$-$C_6$ alkyl groups having an acylamino substituent, including 2-(propionylamino)ethyl and the like.

The term "ureido" refers to the group —NRC(O)NR'R" where R, R and R" are independently H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_2$-$C_6$ alkyl," or "heterocycloalkyl $C_1$-$C_6$ alkyl," and where R' and R," together with the nitrogen atom to which they are attached, can optionally form a 3-8-membered heterocycloalkyl ring.

The term "ureido $C_1$-$C_6$ alkyl" refers to $C_1$-$C_6$-alkyl groups having an ureido substituent, including 2-(N'-methylureido)ethyl and the like.

The term "carbamate" refers to the group —NRC(O)OR' where R and R' are independently "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "$C_1$-$C_6$ alkyl aryl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl" and optionally R can also be hydrogen.

The term "amino" refers to the group —NRR' where R and R' are independently H, "$C_1$-$C_6$ alkyl", "aryl", "heteroaryl", "$C_1$-$C_6$ alkyl aryl", "$C_1$-$C_6$ alkyl heteroaryl," "$C_3$-$C_8$-cycloalkyl," or "heterocycloalkyl," and where R and R', together with the nitrogen atom to which they are attached, can optionally form a 3-8-membered heterocycloalkyl ring.

The term "amino $C_1$-$C_6$ alkyl" refers to alkyl groups having an amino substituent, including 2-(1-pyrrolidinyl) ethyl and the like.

The term "ammonium" refers to a positively charged group —N*RR'R" where R, R' and R" are independently "$C_1$-$C_6$ alkyl", "$C_1$-$C_6$ alkyl aryl", "$C_1$-$C_6$ alkyl heteroaryl," "$C_3$-$C_8$-cycloalkyl," or "heterocycloalkyl," and where R and R', together with the nitrogen atom to which they are attached, can optionally form a 3-8-membered heterocycloalkyl ring.

The term "ammonium $C_1$-$C_6$ alkyl" refers to alkyl groups having an ammonium substituent, including 1-ethylpyrrolidinium and the like.

The term "halogen" refers to fluoro, chloro, bromo and iodo atoms.

The term "sulfonyloxy" refers to a group —$OSO_2$—R wherein R is selected from "$C_1$-$C_6$ alkyl," "$C_1$-$C_6$ alkyl" substituted with halogens, e.g., an —$OSO_2$—$CF_3$ group, "$C_2$-$C_6$ alkenyl," "$C_2$-$C_6$ $C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfamate" refers to a group —$OSO_2$—NRR' wherein R and R' are independently selected from H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl" and the like.

The term "sulfonyloxy $C_1$-$C_6$ alkyl" refers to alkyl groups having a sulfonyloxy substituent, including 2-(methylsulfonyloxy)ethyl and the like.

The term "sulfonyl" refers to group "—$SO_2$—R" wherein R is selected from "aryl," "heteroaryl," "$C_1$-$C_6$ alkyl," "$C_1$-$C_6$ alkyl" substituted with halogens, e.g., an —$SO_2$—$CF_3$ group, "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfonyl $C_1$-$C_6$ alkyl" refers to alkyl groups having a sulfonyl substituent, including 2-(methylsulfonyl) ethyl and the like.

The term "sulfinyl" refers to a group "—S(O)—R" wherein R is selected from "$C_1$-$C_6$ alkyl," "$C_1$-$C_6$ alkyl" substituted with halogens, e.g., a —SO—$CF_3$ group, "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfinyl $C_1$-$C_6$ alkyl" refers to alkyl groups having a sulfinyl substituent, including 2-(methylsulfinyl) ethyl and the like.

The term "sulfanyl" refers to groups —S—R where R includes H, halogens, e.g. a —$SF_5$ group, optionally substituted "$C_1$-$C_6$ alkyl," in particular "$C_1$-$C_6$ alkyl" substituted with halogens, e.g., a —S—$CF_3$ group, "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "alkynylheteroaryl," "$C_3$-$C_8$-cycloalkyl $C_1$-$C_6$ alkyl," or "heterocycloalkyl $C_1$-$C_6$ alkyl".

The term "sulfanyl $C_1$-$C_6$ alkyl" refers to $C_1$-$C_5$-alkyl groups having a sulfanyl substituent, including 2-(ethylsulfanyl)ethyl and the like.

The term "sulfonylamino" refers to a group —$NRSO_2$—R' where R and R' are independently "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfonylamino $C_1$-$C_6$ alkyl" refers to alkyl groups having a sulfonylamino substituent, including 2-(ethylsulfonylamino)ethyl and the like.

The term "aminosulfonyl" refers to a group —$SO_2$—NRR' where R and R' are independently H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl", and where R and R', together with the nitrogen atom to which they are attached, can optionally form a 3-8-membered heterocycloalkyl ring. Aminosulfonyl groups include cyclohexylaminosulfonyl, piperidinylsulfonyl and the like.

The term "aminosulfonyl $C_1$-$C_6$ alkyl" refers to $C_1$-$C_6$ alkyl groups having an aminosulfonyl substituent, including 2-(cyclohexylaminosulfonyl)ethyl and the like.

Unless otherwise constrained by the definition of the individual substituent, the term "substituted" refers to groups substituted with from 1 to 5 substituents selected from the group consisting of "$C_1$-$C_6$ alkyl," "$C_2$-$C_6$ alkenyl," "$C_2$-$C_6$ alkynyl," "$C_3$-$C_8$-cycloalkyl," "heterocycloalkyl," "$C_1$-$C_6$ alkyl aryl," "$C_1$-$C_6$ alkyl heteroaryl," "$C_1$-$C_6$ alkyl $C_3$-$C_8$-cycloalkyl," "$C_1$-$C_6$ alkyl heterocycloalkyl," "acyl", "amino," "amide", "aminosulfonyl," "ammonium," "acyl amino," "aminocarbonyl," "aryl," "heteroaryl," "sulfinyl," "sulfonyl," "sulphonamide", "alkoxy," "alkoxy carbonyl," "carbamate," "sulfanyl," "halogen," trihalomethyl, cyano, hydroxy, mercapto, nitro, and the like.

The term "pharmaceutically acceptable salts or complexes" refers to salts or complexes of the compounds according to the invention. Examples of such salts are formed from acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, naphthalene disulfonic acid, methane sulfonic acid, p-toluene sulfonic acid and poly-galacturonic acid.

"Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism. The prodrug is a derivative of the compounds according to the invention and presenting anti-malarial activity that has a chemically or metabolically decomposable group, and a compound that may be converted into a pharmaceutically active compound according to the invention in vivo by solvolysis under physiological conditions. The prodrug is converted into a compound according to the present invention by a reaction with an enzyme, gastric acid or the like under a physiological condition in the living body, e.g. by oxidation, reduction, hydrolysis or the like, each of which is carried out enzymatically. These compounds can be produced from compounds of the present invention according to well-known methods.

The term "indirectly" also encompasses metabolites of compounds according to the invention.

The term "metabolite" refers to all molecules derived from any of the compounds according to the present invention in a cell or organism, preferably mammal.

In the context of the present invention are encompassed pharmaceutically acceptable salts, hydrates, solvates, or polymorphs and pharmaceutically active derivatives of compounds of the invention.

The term "malaria" includes disease and conditions related to an infection by *Plasmodium*.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or relieving the disease, i.e., causing regression of the disease and/or its symptoms or conditions.

The term "effective amount" includes "prophylaxis-effective amount" as well as "treatment-effective amount".

The term "prophylaxis-effective amount" refers to a concentration of compound of this invention that is effective in inhibiting, decreasing the likelihood of the disease by malarial parasites, or preventing malarial infection or preventing the delayed onset of the disease by malarial parasites, when administered before infection, i.e. before, during and/or slightly after the exposure period to malarial parasites.

The term "prophylaxis" includes causal prophylaxis, i.e. antimalarial activity comprising preventing the pre-erythrocytic development of the parasite, suppressive prophylaxis, i.e. antimalarial activity comprising suppressing the development of the blood stage infection and terminal prophylaxis, i.e. antimalarial activity comprising suppressing the development of intra-hepatic stage infection. This term includes primary prophylaxis (i.e. preventing initial infection) where the antimalarial compound is administered before, during and/or after the exposure period to malarial parasites and terminal prophylaxis (i.e. to prevent relapses or delayed onset of clinical symptoms of malaria) when the antimalarial compound is administered towards the end of and/or slightly after the exposure period to malarial parasites but before the clinical symptoms. Typically, against *P. falciparum* infections, suppressive phophylaxis is used whereas against *P. vivax* or a combination of *P. falciparum* and *P. vivax*, terminal prophylaxis is used.

Likewise, the term "treatment-effective amount" refers to a concentration of compound that is effective in treating malaria infection, e.g. leads to a reduction in parasite numbers in blood following microscopic examination when administered after infection has occurred.

The term "subject" as used herein refers to mammals. For examples, mammals contemplated by the present invention include humans and the like.

Compounds

According to one embodiment, is provided a compound according to Formula (I):

(I)

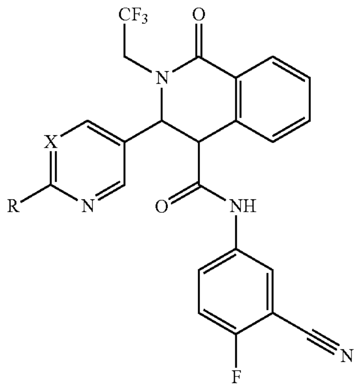

Wherein X is selected from N and CH; when X is CH: R is selected from $-CF_3$, $-CHF_2$, —O— cyclopropyl, —O-isopropyl, $-OCHF_2$, —CN, $-OCH_2CF_3$ and $-NH(C{=}O)CH_3$; and when X is N: R is $-CF_3$; as well as pharmaceutically acceptable salts, hydrates, solvates, tautomers, polymorphs, racemic mixtures, optically active forms and pharmaceutically active derivative thereof.

In a particular embodiment, the invention provides a compound according to the invention wherein X is CH.

In a particular embodiment, the invention provides a compound according to the invention wherein X is N.

In another particular embodiment, the invention provides a compound according to the invention wherein R is $-CF_3$.

In another particular embodiment, the invention provides a compound according to the invention wherein R is O-cyclopropyl.

In another particular embodiment, the invention provides a compound according to the invention wherein R is —O-isopropyl.

In another particular embodiment, the invention provides a compound according to the invention wherein R is $-OCHF_2$.

In another particular embodiment, the invention provides a compound according to the invention wherein R is —CN.

In another particular embodiment, the invention provides a compound according to the invention wherein R is $-OCH_2CF_3$.

In another particular embodiment, the invention provides a compound according to the invention wherein R is $-NH(C{=}O)CH_3$.

In a particular embodiment is provided a compound selected from the following group: N-(3-cyano-4-fluorophenyl)-1-oxo-2-(2,2,2-trifluoroethyl)-3-(6-(trifluoromethyl)pyridin-3-yl)-1,2,3,4-tetrahydroisoquinoline-4-carboxamide; N-(3-cyano-4-fluorophenyl)-3-(6-(difluoromethyl)pyridin-3-yl)-1-oxo-2-(2,2,2-trifluoroethyl)-1,2,3,4-tetrahydroisoquinoline-4-carboxamide; N-(3-cyano-4-fluorophenyl)-3-(6-cyclo propoxypyridin-3-yl)-1-oxo-2-(2,2,2-trifluoroethyl)-1,2,3,4-tetrahydroisoquinoline-4-carboxamide; N-(3-cyano-4-fluorophenyl)-3-(6-isopropoxypyridin-3-yl)-1-oxo-2-(2,2,2-trifluoroethyl)-1,2,3,4-tetrahydroisoquinoline-4-carboxamide; (3-cyano-4-fluorophenyl)-3-(6-(difluoromethoxy)pyridin-3-yl)-1-oxo-2-(2,2,2-trifluoroethyl)-1,2,3,4-tetrahydroisoquinoline-4-carboxamide; N-(3-cyano-4-fluorophenyl)-3-(6-cyanopyridin-3-yl)-1-oxo-2-(2,2,2-trifluoroethyl)-1,2,3,4-tetrahydroisoquinoline-4-carboxamide; N-(3-cyano-4-fluorophenyl)-3-(6-(difluoromethoxy)pyridin-3-yl)-1-oxo-2-(2,2,2-trifluoroethyl)-1,2,3,4-tetrahydroisoquinoline-4-carboxamide; N-(3-cyano-4-fluorophenyl)-1-oxo-3-(6-(2,2,2-trifluoroethoxy)pyridin-3-yl)-2-(2,2,2-trifluoroethyl)-1,2,3,4-tetrahydroisoquinoline-4-carboxamide; 3-(6-acetamidopyridin-3-yl)-N-(3-cyano-4-fluorophenyl)-1-oxo-2-(2,2,2-trifluoroethyl)-1,2,3,4-tetrahydroisoquinoline-4-carboxamide and N-(3-cyano-4-fluorophenyl)-1-oxo-2-(2,2,2-trifluoroethyl)-3-(2-(trifluoromethyl) pyrimidin-5-yl)-1,2,3,4-tetrahydroisoquinoline-4-carboxamide, as well as pharmaceutically acceptable salts, hydrates, solvates, tautomers, polymorphs, racemic mixtures, optically active forms and pharmaceutically active derivative thereof.

According to a further particular embodiment, a compound of the invention is selected among the following group: (3S,4S)—N-(3-cyano-4-fluorophenyl)-1-oxo-2-(2,2,2-trifluoroethyl)-3-(6-(trifluoromethyl) pyridin-3-yl)-1,2,3,4-tetrahydroisoquinoline-4-carboxamide; (3S,4S)—N-(3-cyano-4-fluorophenyl)-3-(6-(difluoromethyl)pyridin-3-yl)-1-oxo-2-(2,2,2-trifluoroethyl)-1,2,3,4-tetrahydroisoquinoline-4-carboxamide; (3S,4S)—N-(3-cyano-4-fluorophenyl)-3-(6-cyclo propoxypyridin-3-yl)-1-oxo-2-(2,2,2-trifluoroethyl)-1,2,3,4-tetrahydroisoquinoline-4-carboxamide; rac-(3S,4S)—N-(3-cyano-4-fluorophenyl)-3-(6-isopropoxypyridin-3-yl)-1-oxo-2-(2,2,2-trifluoroethyl)-1,2,3,4-tetrahydroisoquinoline-4-carboxamide; (3S,4S)—N-(3-cyano-4-fluorophenyl)-3-(6-(difluoromethoxy)pyridin-3-yl)-1-oxo-2-(2,2,2-trifluoroethyl)-1,2,3,4-tetrahydroisoquinoline-4-carboxamide; (3S,4S)—N-(3-cyano-4-fluorophenyl)-3-(6-cyano pyridin-3-yl)-1-oxo-2-(2,2,2-trifluoroethyl)-1,2,3,4-tetrahydroisoquinoline-4-carboxamide; (3S,4S)—N-(3-cyano-4-fluorophenyl)-3-(6-(difluoromethoxy)pyridin-3-yl)-1-oxo-2-(2,2,2-trifluoroethyl)-1,2,3,4-tetrahydroisoquinoline-4-carboxamide; (3S,4S)—N-(3-cyano-4-fluorophenyl)-1-oxo-3-(6-(2,2,2-trifluoroethoxy) pyridin-3-yl)-2-(2,2,2-trifluoroethyl)-1,2,3,4-tetrahydroisoquinoline-4-carboxamide; (3S,4S)-3-(6-acetamidopyridin-3-yl)-N-(3-cyano-4-fluorophenyl)-1-oxo-2-(2,2,2-trifluoroethyl)-1,2,3,4-tetrahydroisoquinoline-4-carboxamide and (3S,4S)—N-(3-cyano-4-fluorophenyl)-1-oxo-2-(2,2,2-trifluoroethyl)-3-(2-(trifluoromethyl) pyrimidin-5-yl)-1,2,3,4-tetrahydroisoquinoline-4-carboxamide, as well as pharmaceutically acceptable salts thereof.

In a further particular embodiment is provided a diastereoisomer of a compound according to the invention which is trans- in configuration.

In a further particular embodiment is provided an enantiomer of a compound according to the invention which is in the 3S,4S configuration.

The compounds of the invention are useful in the manufacture of a medicament for the prevention or treatment of malaria, are capable of killing and/or inhibiting malaria parasite replication.

Compositions

The invention provides pharmaceutical compositions useful for the prophylaxis or treatment of malaria. The invention further provides methods for treating a mammalian patient, and most preferably a human patient, who is suffering from malaria.

In another particular embodiment, is provided a pharmaceutical formulation containing at least one derivative according the invention and a pharmaceutically acceptable carrier, diluent or excipient thereof.

In another particular embodiment, is provided a pharmaceutical formulation comprising a compound according to Formula (I) and a further antimalarial agent as defined in the detailed description.

In another particular embodiment, is provided a pharmaceutical formulation comprising a compound according to Formula (I) and at least one further antimalarial agent selected from artemisinin and its derivatives such as artemisinin and its derivatives (such as artemether, artesunate or dihydroartemisinin), chloroquine, hydroxychloroquine, quinine, quinidine, mefloquine, amodiaquine, atovaquone/proguanil, clindamycin, doxycycline, lumefantrine, piperaquine, pyronaridine, halofantrine, pyrimethamine-sulfadoxine, primaquine, quinacrine, ferroquine, tafenoquine, arterolane, Spiro[3H-indole-3,1'-[1H]pyrido[3,4-b]indol]-2(1H)-one, 5,7'-dichloro-6'-fluoro-2',3',4',9'-tetrahydro-3'-methyl-,(1'R,3'S)-] (Cipargamin, KAE609, CAS Registry Number: 1193314-23-6), 2-(1,1-difluoroethyl)-5-methyl-N-[4-(pentafluoro-$\lambda^6$-sulfanyl)phenyl]-[1,2,4]triazolo[1,5-a] pyrimidin-7-amine (DSM265, CAS Registry Number: 1282041-94-4), Morpholine, 4-[2-(4-cis-dispiro[cyclohexane-1,3'-[1,2,4]trioxolane-5',2''-tricyclo[3.3.1.13,7]decan]-4-ylphenoxy) ethyl]-] (Artefenomel, OZ439, CAS Registry Number: 1029939-86-3), 4-Quinolinecarboxamide, 6-fluoro-2-[4-(4-morpholinylmethyl) phenyl]-N-[2-(1-pyrrolidinyl)ethyl]- (DDD107498, CAS Registry Number: 1469439-69-7), Ethanone, 2-amino-1-[2-(4-fluorophenyl)-3-[(4-fluorophenyl)amino]-5,6-dihydro-8,8-dimethylimidazo[1,2-a]pyrazin-7(8H)-yl]- (Ganaplacide, KAF-156, CAS Registry Number 1261113-96-5), 5-[4-(Methylsulfonyl)phenyl]-6'-(trifluoromethyl)[3,3'-bipyridin]-2-amine (MMV390048, CAS Registry Number: 1314883-11-8), 4(1H)-Quinolinone, 6-chloro-7-methoxy-2-methyl-3-[4-[4-(trifluoromethoxy)phenoxy]phenyl]- (ELQ-300, CAS Registry Number: 1354745-52-0).

Pharmaceutical compositions of the invention can contain one or more compound(s) of the invention in any form described herein. Compositions of this invention may further comprise one or more pharmaceutically acceptable additional ingredient(s), such as alum, stabilizers, antimicrobial agents, buffers, coloring agents, flavoring agents, adjuvants, and the like.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended dosage range to be employed. Compositions according to the invention are preferably oral.

Compositions of this invention may be liquid formulations, including, but not limited to, aqueous or oily suspensions, solutions, emulsions, syrups, and elixirs. Liquid forms suitable for oral administration may include a suitable aqueous or non-aqueous vehicle with buffers, suspending and dispensing agents, colorants, flavors and the like. The compositions may also be formulated as a dry product for reconstitution with water or other suitable vehicle before use. Such liquid preparations may contain additives, including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Non-aqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid. Further materials as well as processing techniques and the like are set out in out in *Part 5 of Remington's "The Science and Practice of Pharmacy", 22nd Edition,* 2012*, University of the Sciences in Philadelphia*, Lippincott Williams & Wilkins, which is incorporated herein by reference. Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maize starch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Injectable compositions are typically based upon injectable sterile saline or phosphate-buffered saline or other injectable carriers known in the art.

Compositions of this invention may also be formulated as suppositories, which may contain suppository bases including, but not limited to, cocoa butter or glycerides. Compositions of this invention may also be formulated for inhalation, which may be in a form including, but not is limited to, a solution, suspension, or emulsion that may be administered as a dry powder or in the form of an aerosol using a propellant, such as dichlorodifluoromethane or trichlorofluoromethane. Compositions of this invention may also be formulated transdermal formulations comprising aqueous or non-aqueous vehicles including, but not limited to, creams, ointments, lotions, pastes, medicated plaster, patch, or membrane.

Compositions of this invention may also be formulated for parenteral administration, including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents.

The composition may also be provided in a powder form for reconstitution with a suitable vehicle including, but not limited to, sterile, pyrogen-free water.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions of this invention may also be formulated as a liposome preparation. The liposome preparation can comprise liposomes which penetrate the cells of interest or the stratum corneum, and fuse with the cell membrane, resulting in delivery of the contents of the liposome into the cell. Other suitable formulations can employ niosomes. Niosomes are lipid vesicles similar to liposomes, with membranes consisting largely of non-ionic lipids, some forms of which are effective for transporting compounds across the stratum corneum.

The compounds of this invention can also be administered in sustained release forms or from sustained release drug delivery systems. A description of representative sustained release materials can also be found in the incorporated materials in Remington's Pharmaceutical Sciences.

Mode of Administration

Compositions of this invention may be administered in any manner, including, but not limited to, orally, parenterally, sublingually, transdermally, vaginally, rectally, transmucosally, topically, via inhalation, via buccal or intranasal administration, or combinations thereof. Parenteral administration includes, but is not limited to, intravenous, intraarterial, intra-peritoneal, subcutaneous, intramuscular, intrathecal, and intra-articular. The compositions of this invention may also be administered in the form of an implant, which allows slow release of the compositions as well as a slow controlled i.v. infusion. In a preferred embodiment, compounds according to the invention are administered orally.

This invention is further illustrated by the following examples that are not intended to limit the scope of the invention in any way.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Combination

According to the invention, the compounds of the invention and pharmaceutical formulations thereof can be administered alone or in combination with a co-agent useful in the treatment of malaria, such as substances useful in the treatment and/or prevention of malaria e.g. for example a co-agent including, but not limited to, artemisinin and its derivatives such as arthemether, artesunate, dihydroartemisinin, chloroquine, hydroxychloroquine, quinine, mefloquine, amodiaquine, atovaquone/proguanil, doxycycline, clindamycin, halofantrine, lumefantrine, pyronaridine, pyrimethamine-sulfadoxine, ferroquine, tafenoquine, piperaquine and primaquine.

Further co-agents useful in combination with the compounds of the invention are selected from Spiro[3H-indole-3,1'-[1H]pyrido[3,4-b]indol]-2(1H)-one, 5,7'-dichloro-6'-fluoro-2',3',4',9'-tetrahydro-3'-methyl-,(1'R,3'S)-] (Cipargamin, CAS Registry Number: 1193314-23-6), 2-(1,1-difluoroethyl)-5-methyl-N-[4-(pentafluoro-$\lambda^6$-sulfanyl) phenyl]-[1,2,4]triazolo[1,5-a]pyrimidin-7-amine (DSM265, CAS Registry Number: 1282041-94-4), Morpholine, 4-[2-(4-cis-dispiro[cyclohexane-1,3'-[1,2,4]trioxolane-5',2"-tricyclo[3.3.1.13,7]decan]-4-ylphenoxy) ethyl]-] (Artefenomel, OZ439, CAS Registry Number: 1029939-86-3), 4-Quinolinecarboxamide, 6-fluoro-2-[4-(4-morpholinylmethyl)phenyl]-N-[2-(1-pyrrolidinyl) ethyl]- (DDD107498, CAS Registry Number: 1469439-69-7), Ethanone, 2-amino-1-[2-(4-fluorophenyl)-3-[(4-fluorophenyl)amino]-5,6-dihydro-8,8-dimethylimidazo[1,2-a]pyrazin-7(8H)-yl]- (Ganaplacide, KAF-156, CAS Registry Number 1261113-96-5), 5-[4-(Methylsulfonyl)phenyl]-6'-(trifluoromethyl)[3,3'-bipyridin]-2-amine (MMV390048, CAS Registry Number: 1314883-11-8), 4(1H)-Quinolinone, 6-chloro-7-methoxy-2-methyl-3-[4-[4-(trifluoromethoxy)phenoxy]phenyl]- (ELQ-300, CAS Registry Number: 1354745-52-0), 4-Isoquinolinecarboxamide, N-(3-cyano-4-fluorophenyl)-1,2,3,4-tetrahydro-1-oxo-3-(3-pyridinyl)-2-(2,2,2-trifluoroethyl)-, (3S,4S)- (SJ-733, CAS Registry Number 1424799-20-1), (R)—N2-(4-Cyclopropyl-5-fluoro-6-methylpyridin-2-yl)-N4-(1,5-dimethyl-1H-pyrazol-3-yl)-5-(3,4-dimethylpiperazin-1-yl)pyrimidine-2,4-diamine (CAS Registry Number 1821293-40-6, 4-(1,1-Dimethylethyl)-2-[[(1,1-dimethylethyl)amino]methyl]-6-[5-fluoro-6-(trifluoromethyl)-3-pyridinyl]phenol (JPC3210, CAS Registry Number 1609655-35-7, [(3R)-3-(4-fluorophenyl)-1-pyrrolidinyl][4-[(2R)-2-hydroxy-3-(2H-tetrazol-2-yl)propoxy]phenyl]-methanone (GSK701, CAS Registry Number 2366983-10-8).

The invention encompasses the administration of a compound according to the invention or of a pharmaceutical formulation thereof, wherein the compounds of the invention or the pharmaceutical formulation thereof are administered to an individual prior to, simultaneously or sequentially with other therapeutic regimens or co-agents useful in the treatment of malaria (e.g. multiple drug regimens), in an effective amount. Compounds of the invention or the pharmaceutical formulations thereof that are administered simultaneously with said co-agents can be administered in the same or different composition(s) and by the same or different route(s) of administration.

Patients

In an embodiment, patients according to the invention are patients suffering from malaria.

In another embodiment, patients according to the invention are patients with a high risk of being infected by *Plasmodium.*

In another embodiment, patients according to the invention are patients with a high risk of being infected by *Plasmodium falciparum.*

In another embodiment, patients according to the invention are patients with a high risk of being infected by *Plasmodium vivax.*

In another embodiment, patients according to the invention are patients with a high risk of being infected by *Plasmodium ovale.*

In another embodiment, patients according to the invention are patients with a high risk of being infected by *Plasmodium malariae.*

In another embodiment, patients according to the invention are patients with a high risk of being infected by *Plasmodium knowlesi.*

Use According to the Invention

In one embodiment, the invention provides a compound according to Formula (I) as well as pharmaceutically acceptable salts, hydrates, solvates, or polymorphs, and pharmaceutically active derivative thereof for the treatment or prophylaxis of malaria.

In another embodiment, the invention provides a method for preventing or treating malaria in a subject. The method comprises administering an effective amount of a compound according to the invention, or a pharmaceutically acceptable salt or a pharmaceutically active derivative thereof or a pharmaceutical formulation thereof in a subject in need thereof.

In another embodiment, the invention provides a use of a compound or a method according to the invention wherein the compound is to be administered in combination with a co-agent useful in the treatment of malaria.

In another embodiment, the invention provides a pharmaceutical composition comprising a compound according to the invention in combination with a co-agent useful in the treatment of malaria.

In another embodiment, the invention provides a process for the preparation of a compound according to the invention comprising a step of transforming a compound according to Formula (II) into a compound of Formula (III) in presence of an isochromane-1,3-dione as described under Scheme 1 below:

Scheme 1

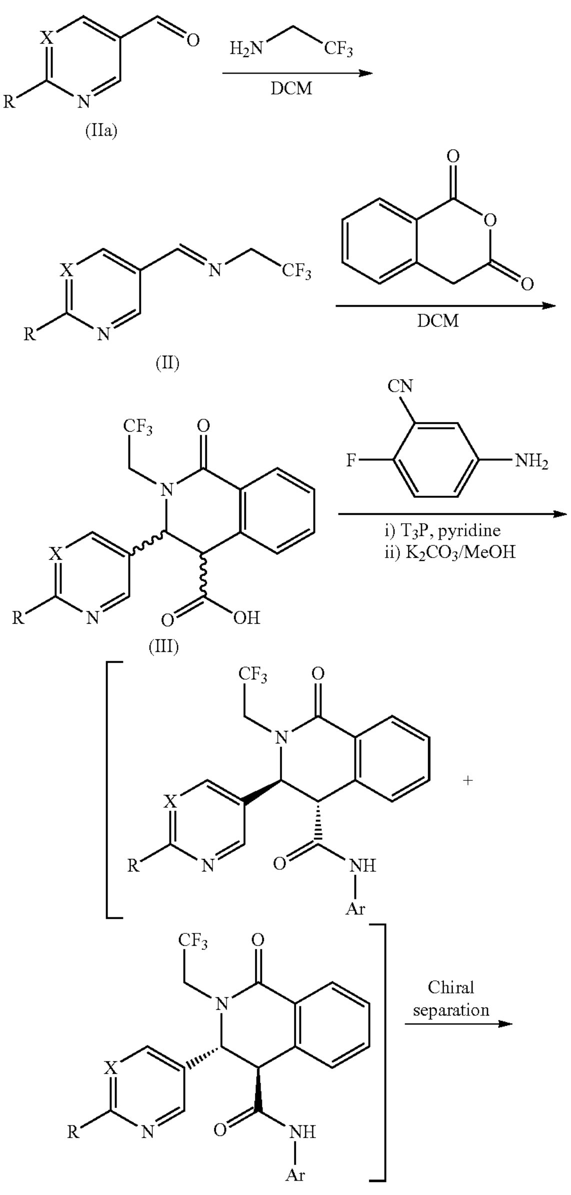

(IIa)

(II)

(III)

(I)

(+,-) trans-racemate

-continued

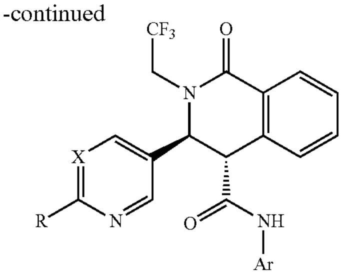

(Ia)
(+) S,S-enantiomer wherein R and X are defined herein.

In another embodiment, the invention provides a process for the preparation of a compound according to the invention comprising a step of transforming a compound according to Formula (III) into a compound of Formula (I) in presence of an optionally substituted phenylamine, e.g. 3-cyano, 4-fluoroaniline as illustrated above.

In another further embodiment, the invention provides a method of preparation of an intermediate of the aldehyde of Formula (IIa) from a corresponding cyano derivative of Formula (IIb), for example as illustrated in Scheme 1b below.

Scheme 1a

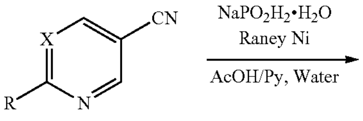

(IIb)

-continued

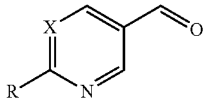

(IIa)

According to a particular embodiment, the use of intermediates (IIb), for example intermediate (viii) results in improved yields, use of cheaper reagents and an easier purification of the intermediates (IIa), in particular intermediate (IIa-1).

In another embodiment, the invention provides a process for the preparation of a compound according to the invention, said method comprising a step of separation of the enantiomers of Formula (III) by stereoselective salt recrystallization employing 1-2 equivalents of a chirally pure amine, such as (1S,2S)-(+)-trans-1-Amino-2-indanol. The specific enantiomer of Formula (III) is then transformed into the corresponding enantiomer of Formula (I), in presence of an optionally substituted phenylamine, e.g. 3-cyano, 4-fluoroaniline.

Scheme 1b

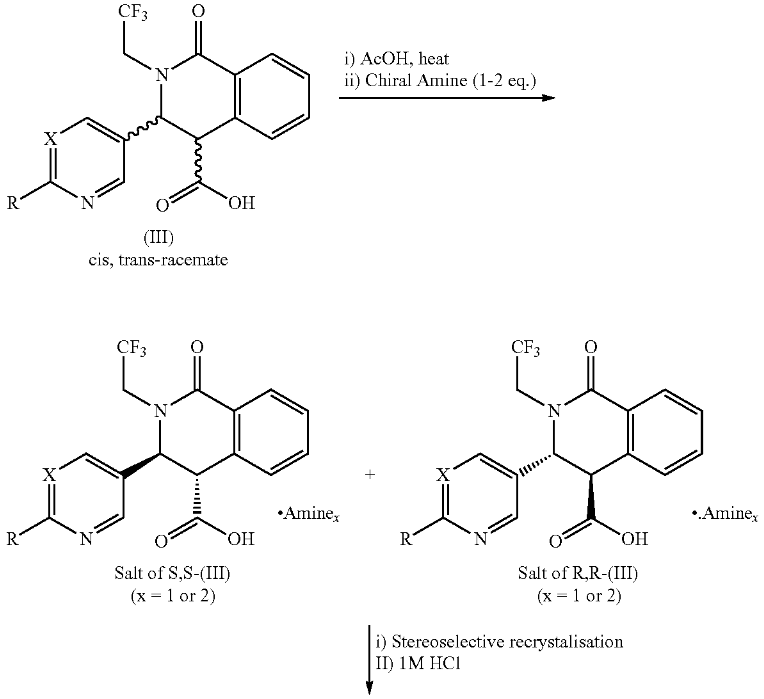

(III)
cis, trans-racemate

Salt of S,S-(III)
(x = 1 or 2)

+

Salt of R,R-(III)
(x = 1 or 2)

-continued

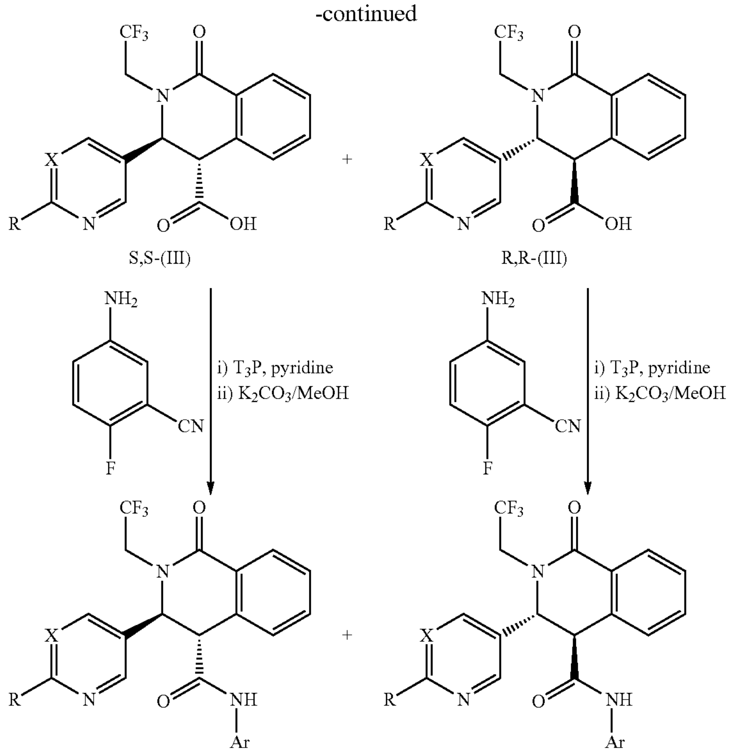

S,S-(III)
R,R-(III)
(Ia)
(+)-S,S-enantiomer
(Ib)
(-)-R,R-enantiomer

In another further embodiment, the invention provides an intermediate of Formula (III), as defined herein, in particular the following compounds: 3-(6-cyclopropoxypyridin-3-yl)-1-oxo-2-(2,2,2-trifluoroethyl)-1,2,3,4-tetrahydroisoquinoline-4-carboxylic acid (III-1), 3-(6-methoxypyridin-3-yl)-1-oxo-2-(2,2,2-trifluoroethyl)-1,2,3,4-tetrahydroisoquinoline-4-carboxylic acid (III-2), 1-oxo-2-(2,2,2-trifluoroethyl)-3-(6-(trifluoromethyl)pyridin-3-yl)-1,2,3,4-tetrahydroisoquinoline-4-carboxylic acid (III-3), 1-oxo-3-(6-(2,2,2-trifluoroethoxy)pyridin-3-yl)-2-(2,2,2-trifluoroethyl)-1,2,3,4-tetrahydroisoquinoline-4-carboxylic acid (III-4), 3-(6-acetamidopyridin-3-yl)-1-oxo-2-(2,2,2-trifluoroethyl)-1,2,3,4-tetrahydroisoquinoline-4-carboxylic acid (III-5), 3-(6-cyanopyridin-3-yl)-1-oxo-2-(2,2,2-trifluoroethyl)-1,2,3,4-tetrahydroisoquinoline-4-carboxylic acid (III-6), 3-(6-(difluoromethoxy)pyridin-3-yl)-1-oxo-2-(2,2,2-trifluoroethyl)-1,2,3,4-tetrahydroisoquinoline-4-carboxylic acid (III-7), 3-(6-(difluoromethyl)pyridin-3-yl)-1-oxo-2-(2,2,2-trifluoroethyl)-1,2,3,4-tetrahydroisoquinoline-4-carboxylic acid (III-8), 1-oxo-2-(2,2,2-trifluoroethyl)-3-(2-(trifluoromethyl)pyrimidin-5-yl)-1,2,3,4-tetrahydroisoquinoline-4-carboxylic acid (III-9).

In another further embodiment, the invention provides an intermediate of Formula (IV), as defined herein, in particular the following compounds: N-(3-cyano-4-fluorophenyl)-3-(6-methoxypyridin-3-yl)-1-oxo-2-(2,2,2-trifluoroethyl)-1,2,3,4-tetrahydroisoquinoline-4-carboxamide (IV-2) In another further embodiment, the invention provides an intermediate of Formula (V), as defined herein, in particular the following compounds: N-(3-cyano-4-fluorophenyl)-3-(6-hydroxypyridin-3-yl)-1-oxo-2-(2,2,2-trifluoroethyl)-1,2,3,4-tetrahydroisoquinoline-4-carboxamide (V-2).

References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. In the following the present invention shall be illustrated by means of some examples, which are not to be viewed as limiting the scope of the invention.

EXAMPLES

The following abbreviations refer respectively to the definitions below:

HEPES (4-(2-hydroxyethyl)-1-piperazineethanesulfonic acid), DCM (dichloromethane), DMSO (Dimethyl Sulfoxide), (LCMS (liquid chromatography mass spectrometry), NADPH (reduced form of nicotinamide adenine dinucleotide phosphate), NEAA (Non-essential amino acids), PBS (Phosphate-buffered saline), RPMI (Roswell Park Memorial Institute), SBFI (Sodium-binding benzofuran isophthalate), TLC (thin layer chromatography), The compounds of invention have been named according to the IUPAC standards used in the program ChemDraw (PerkinElmer, Version 16.0.1.4).

All reagents and starting materials were obtained from Angene, Sigma-Aldrich, Enamine, Apollo Scientific or Fluorochem.

Example 1: Synthesis of Compounds According to the Invention

The compounds of the invention can be prepared from readily available starting materials using methods and procedures known from the skilled person. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

Compounds 1 to 9 of the invention are synthesized as described in the general synthetic routes described herein. In particular, Compounds of Formula (I) are synthesized according to Scheme 2 below. For the sake of clarity and consistency, the following nomenclature is used: the compounds are represented with their compound number and when an isolated trans single enantiomer of the (3S,4S) configuration is described, this would correspond to this number with an "a". When an isolated trans single enantiomer of the (3R,4R) configuration is described, this would correspond to this number with a "b".

Synthesis of (3S,4S)—N-(3-cyano-4-fluorophenyl)-3-(6-cyclopropoxypyridin-3-yl)-1-oxo-2-(2,2,2-trifluoroethyl)-1,2,3,4-tetrahydroisoiuinoline-4-carboxamide (1a)

Scheme 2

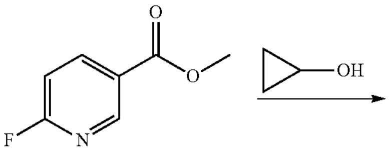

(i)

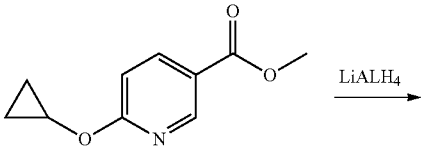

(ii)

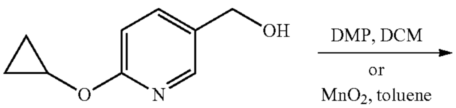

(iii)

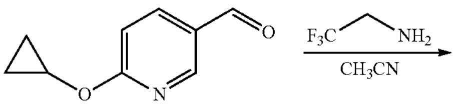

(IIa-1)

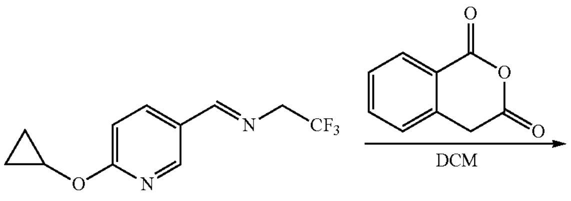

(II-1)

-continued

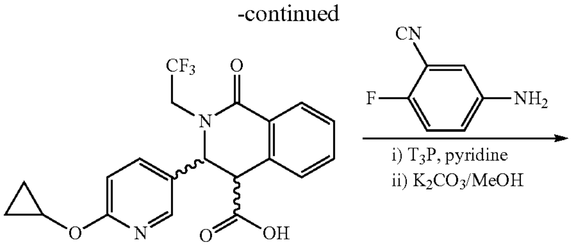

(III-1)

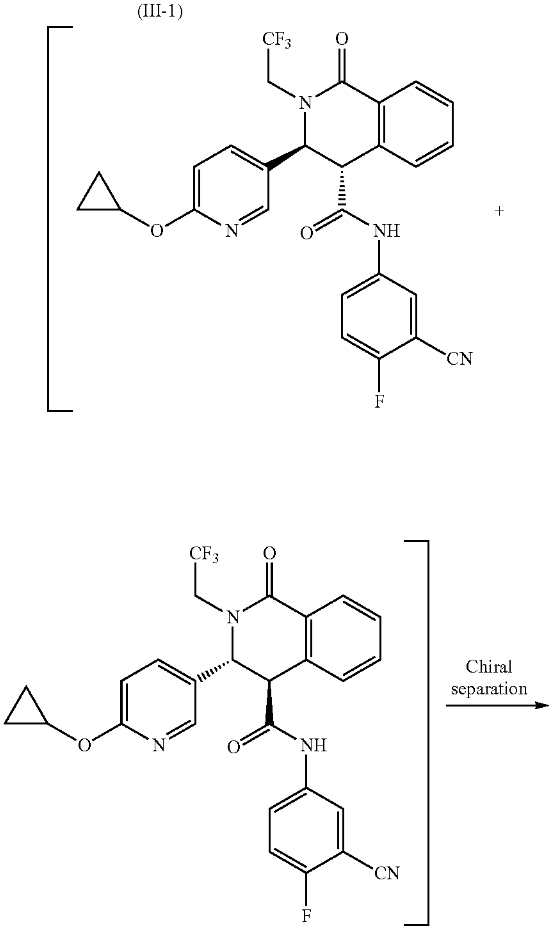

(1)

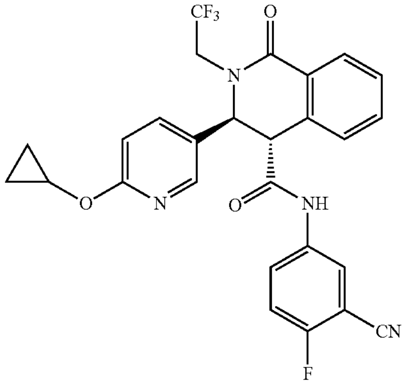

(1a)

Methyl 6-Cyclopropoxynicotinate (Intermediate of Formula (ii))

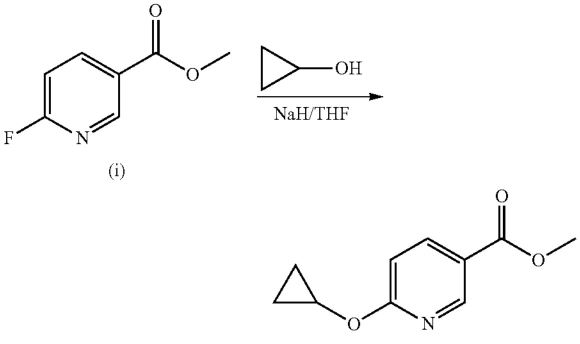

(i)
(ii)

To a stirred solution of cyclopropanol (1.2 mL, 19.3 mmol) in THF (10 mL) at 0° C. under nitrogen was added sodium hydride (0.6 g, 25.8 mmol) portion wise; the reaction mixture was allowed to stir at the same temperature for 30 minutes. To the reaction mixture was added a THE solution (10 mL) of 6-fluoronicotinic acid methyl ester (1) (2 g, 12.9 mmol) (i) drop wise at 0° C. and the reaction mixture was allowed to warm to room temperature over 2 h under nitrogen. After complete consumption of the starting material (monitored by TLC and LCMS), the excess NaH was quenched by addition of saturated aqueous ammonium chloride solution (1 mL). The reaction mixture was then diluted with ethyl acetate (50 mL), washed successively with water (10 mL) and brine solution (10 mL). The organic layer was then dried over sodium sulphate, filtered and the solvent evaporated under reduced pressure to obtain the crude compound as a viscous oil which was then purified by column chromatography over silica gel (100-200 mesh; eluent 10-20% ethyl acetate in hexane) to give methyl 6-cyclopropoxynicotinate (ii) as a colourless oil (1.4 g, 7.25 mmol, 56%). $^1$H NMR (400 MHz, $CDCl_3$): δ 8.87 (d, J=2.0 Hz, 1H), 8.16 (dd, J=8.6 Hz, 2.2 Hz, 1H), 6.78 (d, J=8.7 Hz, 1H), 4.29-4.26 (m, 1H), 3.90 (s, 3H), 0.83-0.78 (m, 4H). LCMS ($NH_4OAc$:$CH_3CN$): m/z: MH+194, $R_t$=3.13 min.

(6-Cyclopropoxyyridin-3-yl)methanol (Intermediate of Formula (iii))

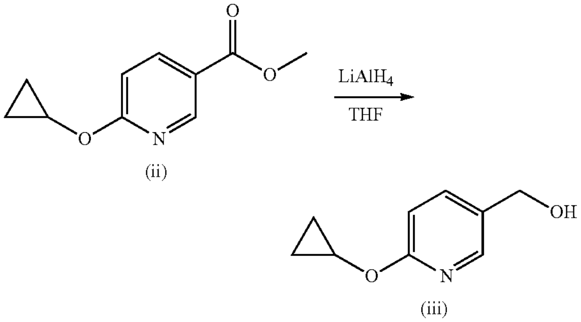

(ii)
(iii)

To a stirred solution of methyl 6-cyclopropoxynicotinate (ii) (1.83 g, 9.5 mmol) in THE (50 mL) at 0° C. under nitrogen was added lithium aluminum hydride (1 M solution in THF) (14 mL, 14.2 mmol) and the reaction mixture was allowed to stir at 0° C. for 1 h. After complete consumption of the starting material (monitored by TLC and LCMS), saturated aqueous sodium sulphate solution (1 mL) was added to quench the excess $LiAlH_4$. The reaction mixture was filtered over a bed of celite, dried (sodium sulphate), filtered and the filtrate concentrated in vacuo to give the title compound (iii) (1.3 g, 7.9 mmol, 83%) of as a colorless liquid. $^1$H NMR (400 MHz, $CDCl_3$): δ 8.19 (s, 1H), 7.63 (dd, J=8.4 Hz, 2.0 Hz, 1H), 6.78 (d, J=8.4 Hz, 1H), 4.63 (d, J=5.2 Hz, 2H), 4.19-4.16 (m, 1H), 1.64 (t, J=5.5 Hz, 1H), 0.80-0.76 (m, 4H). LCMS (Formic acid:$CH_3CN$): m/z: MH+166, $R_t$=1.33.

6-Cyclopropoxynicotinaldehyde (Intermediate of Formula (IIa-1))

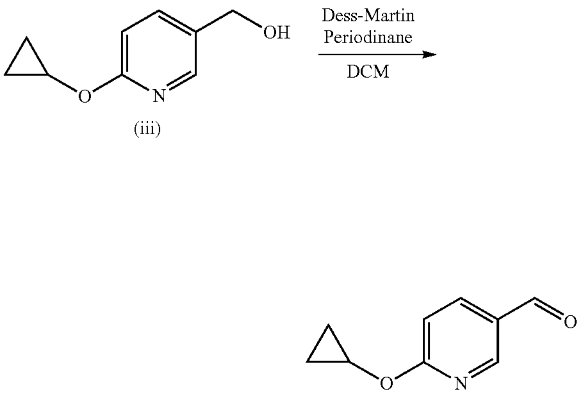

(iii)
(IIa-1)

To a stirred solution of (6-cyclopropoxypyridin-3-yl) methanol (iii) (500 mg, 3.03 mmol) in dichloromethane (15 mL) at 0° C. under nitrogen was added Dess-Martin periodinane (2.5 g, 6.06 mmol) and the reaction mixture was allowed to warm to rt then stirred for a further 1 h. After complete consumption of the starting material (monitored by TLC and LCMS) the reaction mixture was filtered over a bed of celite, the filtrate concentrated in vacuo and the resulting oil purified by column chromatography over silica gel (100-200 mesh; eluent 5% ethyl acetate in hexane) to give the title compound (IIa-1) (400 mg, 2.45 mmol, 81%) as a colourless oil. $^1$H NMR (400 MHz, $CDCl_3$): δ 9.96 (s, 1H), 8.68 (d, J=2.08 Hz, 1H), 8.07 (dd, J=22.4 Hz, 2.2 Hz, 1H), 6.84 (d, J=8.6 Hz, 1H), 4.37-4.32 (m, 1H), 0.88-0.78 (m, 4H). LCMS (Formic acid:$CH_3CN$): m/z: MH+164, $R_t$=1.55 min.

Alternative method using $MnO_2$: A well-stirred solution of (6-cyclopropoxypyridin-3-yl)methanol (iii) (1.2 g, 7.3 mmol) in toluene (30 mL) at room temperature under nitrogen, was treated portion-wise with freshly activated, finely divided manganese (IV) oxide (1.89 g, 21.8 mmol, 3.0 equiv.) and the slurry was heated to 80° C. with continuous monitoring by TLC. After 3 h the mixture was allowed to cool to room temperature, filtered through celite, and the filtrate was concentrated in vacuo to afford a crude oil which was subjected to column chromatography ($SiO_2$, 10:1 hexanes:ethyl acetate) to give the title compound (IIa-1) as a white powder (1.06 g, 6.5 mmol, 89%).

An alternative way of synthesizing an intermediate compound of Formula (IIa-1) is the following:

6-Cyclopropoxynicotinonitrile (Intermediate of Formula (viii))

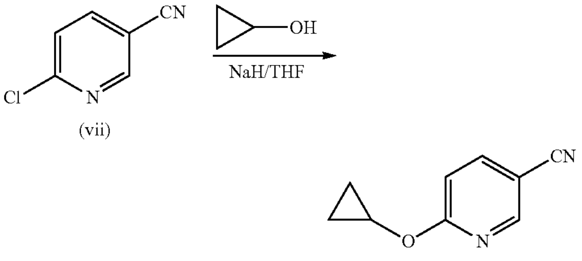

(vii)

(viii)

A solution of cyclopropanol (43.9 ml, 692 mmol) in THE (50 mL) was added slowly to a well-stirred suspension of sodium hydride (27.7 g, 692 mmol, 60% w/w in mineral oil) in THF (1.2 L), under nitrogen at 0° C. After 10 min, 6-chloropyridine-3-carbonitrile (80.0 g, 577.4 mmol, 1.0 equiv.) was added dropwise over 5 min. with continuous stirring. Following consumption of the nitrile as determined by TLC and LCMS, the reaction mixture was quenched by the addition of saturated aqueous ammonium chloride solution (250 mL), followed by dilution with ethyl acetate (250 mL). The organic phase was separated, washed with brine (3x100 mL), dried ($Na_2SO_4$), filtered, and concentrated to give 6-cyclopropoxynicotinonitrile (viii) as a colourless oil (92.1 g, 575.01 mmol, 99% yield), which was used in the next step without further purification. 1H NMR (400 MHz, DMSO-d6) δ 8.72 (d, J=2.1 Hz, 1H), 8.18 (dd, J=2.3, 8.8 Hz, 1H), 7.05 (d, J=8.7 Hz, 1H), 4.35-4.26 (m, 1H), 0.85-0.78 (m, 2H), 0.78-0.70 (m, 2H). LCMS ($NH_4OAc$:$CH_3CN$): m/z: MH+161, $R_t$=1.70 min.

6-Cyclopropoxynicotinaldehyde (Intermediate of Formula (IIa-1))

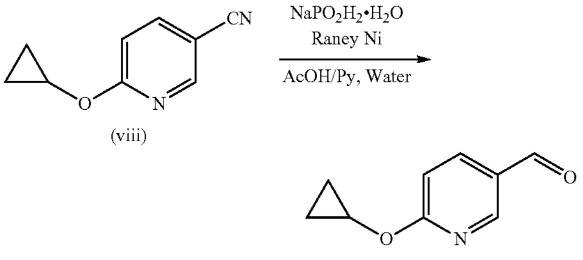

(viii)

(IIa-1)

A solution of sodium hypophosphite monohydrate (192.1 g, 1.81 mol) in water (180 mL) was added to a stirred solution of 6-cyclopropoxynicotinonitrile (58.0 g, 362.5 mmol) (viii) in AcOH/Pyridine (2:1, 540 mL) at room temperature. Raney-Ni (12.0 g) was then carefully added portionwise and the resulting suspension was heated at 80° C. for 60 min. with stirring. The mixture was then filtered through a bed of celite (500 g), the celite washed with EtOAc (500 mL) and the combined filtrates were further diluted with EtOAc (1 L) then washed with water (4x300 mL), saturated aqueous bicarbonate solution (100 mL), and brine (100 mL). The organic phase was dried ($MgSO_4$) and concentrated in vacuo to give the title compound (IIa-1) (54.0 g, 330.94 mmol, 91%) as a colourless oil. 1H NMR (400 MHz, DMSO-d6) δ 9.97 (s, 1H), 8.78 (d, J=2.0 Hz, 1H), 8.14 (dd, J=2.0, 8.6 Hz, 1H), 7.02 (d, J=8.6 Hz, 1H), 4.40-4.25 (m, 1H), 0.90-0.78 (m, 2H), 0.78-0.65 (m, 2H). LCMS (Formic acid:$CH_3CN$): m/z: MH+164, $R_t$=1.55 min.

(E)-1-(6-cyclopropoxypyridin-3-yl)-N-(2,2,2-trifluoroethyl)methanimine (Intermediate of Formula (II-1))

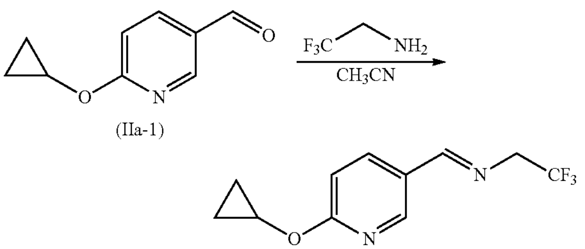

(IIa-1)

(II-1)

To a stirred solution of 6-cyclopropoxynicotinaldehyde (IIa-1) (1 g, 6.1 mmol) in acetonitrile (40 mL) at 0° C. under nitrogen was added 2,2,2-trifluoroethyl amine (3.0 g, 24.4 mmol). The reaction was allowed to warm to rt then stirred for 48 h, during which time the starting materials were completely consumed (monitored by $^1$H NMR). The reaction was concentrated in vacuo to give 1.2 g of a crude oil (II-1) which was used in the next step without further purification.

Cis/trans-(+,−)-3-(6-cyclopropoxypyridin-3-yl)-1-oxo-2-(2,2,2-trifluoroethyl)-1,2,3,4-tetrahydroisoquinoline-4-carboxylic Acid (Intermediate of Formula (III-1))

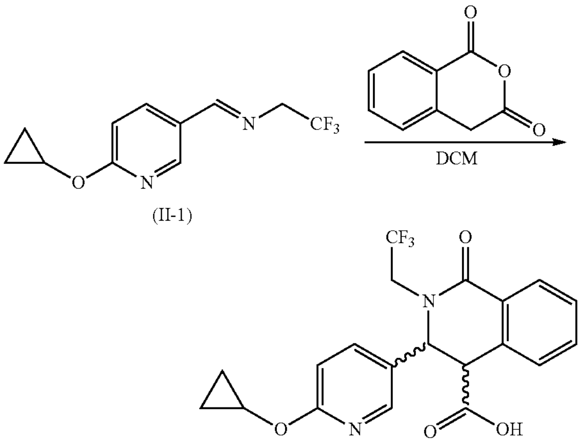

(II-1)

(III-1)

To a stirred solution of (E)-1-(6-cyclopropoxypyridin-3-yl)-N-(2,2,2-trifluoroethyl) methanimine (II-1) (1.2 g, 4.9 mmol) in dichloromethane (15 mL) at room temperature under nitrogen was added homophthalic anhydride (0.8 g, 4.9 mmol) and the reaction mixture stirred for 16 h. The crude reaction was concentrated in vacuo to give 1.85 g of a crude oil which contained 3-(6-cyclopropoxypyridin-3-yl)-1-oxo-2-(2,2,2-trifluoroethyl)-1,2,3,4-tetrahydro isoquinoline-4-carboxylic acid (III-1) as a (1:1) mixture of cis and trans isomers. The crude material was used in the next step without further purification. LCMS (Formic acid:$CH_3CN$): m/z: MH+407, $R_t$=1.53 and 1.55 min.

(3S,4S)—N-(3-cyano-4-fluorophenyl)-3-(6-cyclopropoxypyridin-3-yl)-1-oxo-2-(2,2,2-trifluoroethyl)-1,2,3,4-tetrahydroisoquinoline-4-carboxamide (1a) (Compound of Formula (I) wherein X is CH and R is —O-cyclopropyl)

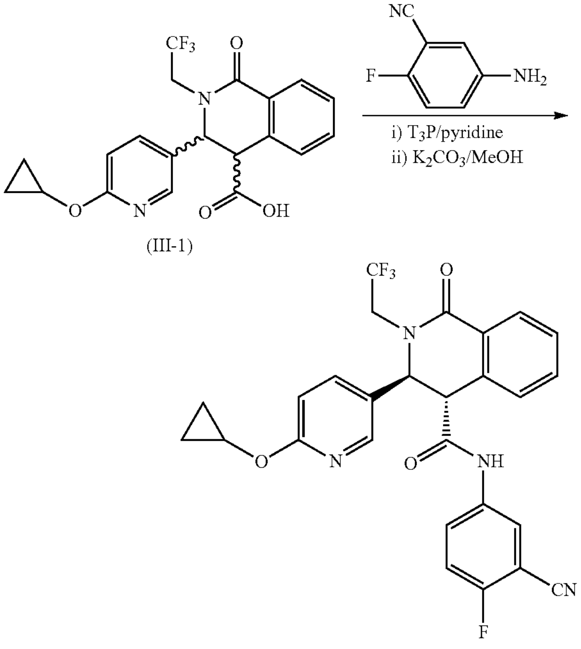

(III-1)

(1a)

To a stirred solution of the 3-(6-cyclopropoxypyridin-3-yl)-1-oxo-2-(2,2,2-trifluoroethyl)-1,2,3,4-tetrahydroisoquinoline-4-carboxylic acid (III-1) as a (1:1) mixture of cis and trans isomers (1.55 g, 3.82 mmol) in pyridine (30.0 mL) at rt under nitrogen was added propylphosphonic anhydride (50% solution in ethyl acetate, 24.3 mL, 38.2 mmol). The mixture was then treated with 5-amino-2-fluorobenzonitrile (0.68 g, 4.96 mmol) and the reaction heated at 60° C. for 16 h. The reaction was then cooled to rt, diluted with ethyl acetate (100 mL), washed with $CuSO_4$ solution (3×10 mL), the organic phase dried ($MgSO_4$), filtered and concentrated in vacuo. The resulting crude oil was diluted with MeOH (30 mL) and stirred with $K_2CO_3$ (1.0 g) at rt for 4 h to induce complete epimerization to the trans isomer. The reaction mixture was then filtered through celite, concentrated in vacuo and the resulting oil purified by chromatography over silica gel (100-200 mesh; 3:7 ethyl acetate:hexane) to give the title compound (1) (1.3 g, 2.48 mmol, 65%) as a white solid. $^1H$ NMR (400 MHz, DMSO-d6): δ 10.79 (s, 1H), 8.05-7.98 (m, 3H), 7.84-7.82 (m, 1H), 7.56-7.46 (m, 4H), 7.30 (d, J=7.0 Hz, 1H), 6.79 (d, J=8.6 Hz, 1H), 5.39 (s, 1H), 4.66-4.58 (m, 1H), 4.24 (s, 1H), 4.11 (bs, 1H), 4.04-3.96 (m, 1H), 0.70 (s, 2H), 0.59 (s, 2H). LCMS (Formic acid: $CH_3CN$): m/z: MH+525, Rt=1.68 min. The desired (3S,4S) trans-enantiomer (1a) could be isolated by preparative chiral HPLC separation of the enantiomers (Chiralpak IC 20×250 mm column with 5μ particle size, eluting with 85/15/0.1 hexane/EtOH/i-propylamine at ambient temperature using a flow rate of 18 mL/min. Compound was detected at a wave length of 220 nm. $[\alpha]_D^{25}$=+111.80° (c=0.5, dichloromethane).

Alternatively, compound (1a) can be synthesized from an intermediate of Formula (III-1), through an isolated enantiomer as follows:

a) Epimerization of cis/trans, racemic 3-(6-cyclopropoxypyridin-3-yl)-1-oxo-2-(2,2,2-trifluoroethyl)-1,2,3,4-tetrahydroisoquinoline-4-carboxylic acid (trans, racemic-Intermediate of Formula III-I)

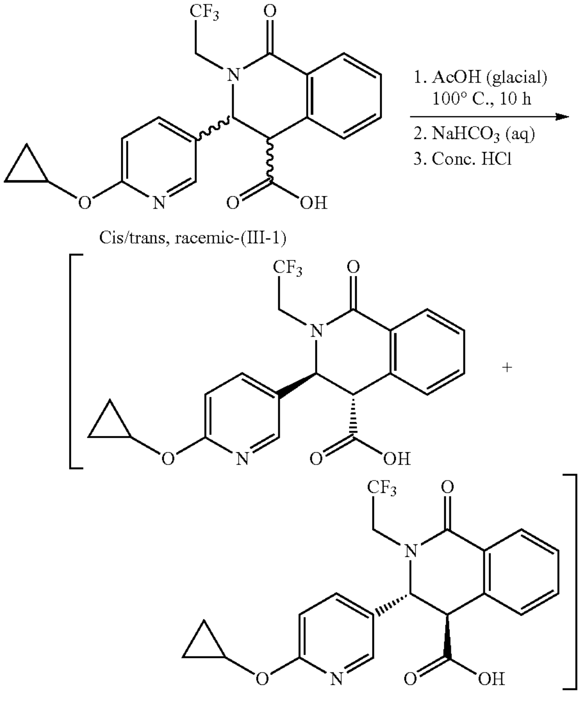

Cis/trans, racemic-(III-1)

Trans, racemic-(III-1')

A stirred solution of a cis/trans-racemic mixture of 3-(6-cyclopropoxypyridin-3-yl)-1-oxo-2-(2,2,2-trifluoroethyl)-1,2,3,4-tetrahydroisoquinoline-4-carboxylic acid (III-1) (230.0 g, 566.4 mmol) in glacial acetic acid (1.0 L) was heated to 100° C. for 10 h, during which time the mixture was completely converted to the trans-racemate as determined by LCMS. The reaction mixture was then cooled to room temperature, diluted with ethyl acetate (2.0 L) and was washed with water (3×500 mL) followed by brine (3×100 mL). The organic layer was dried ($MgSO_4$) and concentrated in vacuo to give a colourless gum which was then dissolved in saturated aqueous sodium bicarbonate solution (250 mL), washed with dichloromethane (3×100 mL). The stirred aqueous phase was then cooled to 0° C., acidified to pH 1 by dropwise addition of concentrated hydrochloric acid and the resulting white solid collected by filtration and dried. Additional material was isolated from the aqueous filtrate, which was extracted with ethyl acetate (2×200 mL) and the organic phase washed with brine (2×100 mL), dried ($MgSO_4$), filtered, and concentrated in vacuo to give an off-white solid which was combined with the solid collected by filtration to give the intermediate of Formula (III-I') as a trans-racemate (152.0 g, 374.1 mmol, 66%). 1H NMR (400 MHz, DMSO-d6) δ 13.12 (br s, 1H), 7.97 (d, J=7.8 Hz, 1H), 7.89 (s, 1H), 7.54-7.41 (m, 2H), 7.33 (d, J=6.7 Hz, 1H), 7.28 (d, J=7.8 Hz, 1H), 6.73 (d, J=8.6 Hz, 1H), 5.49 (s, 1H), 4.75-4.60 (m, 1H), 4.23 (s, 1H), 4.15-4.05 (m, 1H), 4.05-3.85 (m, 1H), 0.80-0.65 (m, 2H), 0.65-0.50 (m, 2H). LCMS (Formic acid: $CH_3CN$): m/z: MH+=407, $R_t$=4.3 min.

b) Resolution of (+, −) trans-3-(6-cyclopropoxy-pyridin-3-yl)-1-oxo-2-(2,2,2-trifluoroethyl)-1,2,3,4-tetrahydroisoquinoline-4-carboxylic acid (Intermediate of Formula III-I)

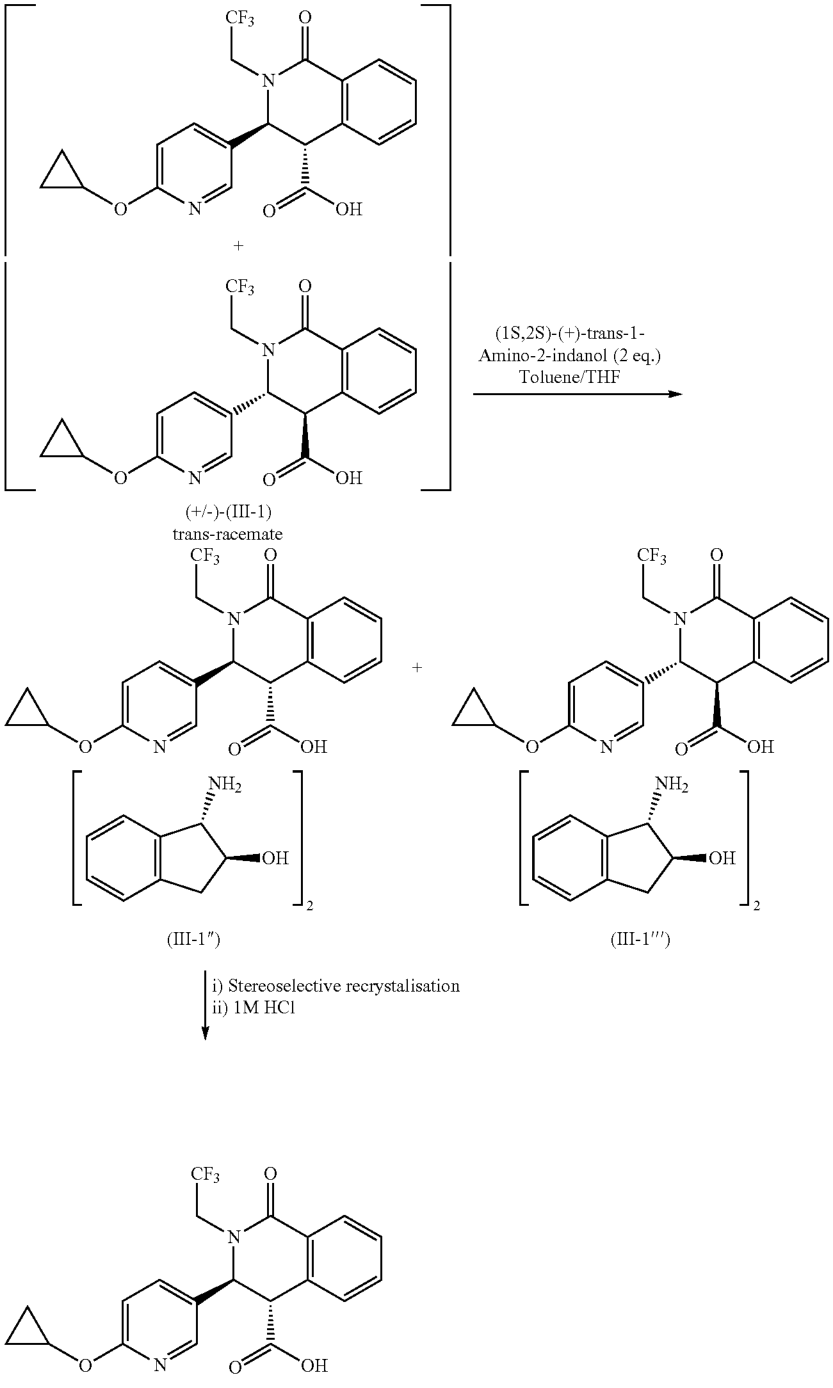

(+/-)-(III-1)
trans-racemate (III-1″)

(III-1‴)

(+)-(S,S)-(III-1′)

To a solution of the trans racemate of the intermediate of Formula III-I' (30.0 g, 73.8 mmol) in toluene and THE (toluene:THF 4:1, 900 mL) at room temperature was added (1S,2S)-(+)-trans-1-amino-2-indanol (22.03 g, 147.6 mmol, 2.0 equiv.) and the slurry purged with nitrogen for 10 min. before warming to 90° C. to give a homogeneous solution. The solution was allowed to cool slowly to room temperature, then cooled to 5° C. After 48 h the resulting crystals were collected by filtration, the residue carefully washed with an ice-cold mixture of toluene and THE (toluene:THF 4:1, 2×30 mL) and the solid dried to give a salt which by NMR consisted of a 2:1 ratio of (1S,2S)-(+)-trans-1-Amino-2-indanol: trans-acid (III-I") (21.1 g, 81% yield with respect to the single enantiomer of the acid III-1, 95% e.e.). All of this material was recrystallized from toluene and THE (toluene:THF 4:1, 440 mL) to give mixed salt with further enhanced optical purity with respect to the acid III-1 (18.8 g, 26.7 mmol, 72%, >99% e.e., $[\alpha]_D^{25}$=+82.8° (c=0.5, dichloromethane)). This material was then dissolved in DCM (200 mL) and hydrochloric acid (1M, 300 mL) added to the stirred solution at room temperature. The organic phase was separated, the aqueous phase washed with DCM (5×50 mL), the organic extracts combined, dried ($MgSO_4$) and concentrated in vacuo to give the (+)-dextrorotatory-(S, S)-acid of intermediate (III-I') as a single enantiomer (9.67 g, 23.8 mmol, >99% e.e., 65% yield based on recovery of the single enantiomer) as a white powder. 1H NMR (400 MHz, DMSO-d6) δ 13.08 (br s, 1H), 7.97 (d, J=7.2 Hz, 1H), 7.89 (s, 1H), 7.54-7.41 (m, 2H), 7.33 (d, J=8.8 Hz, 1H), 7.28 (d, J=6.9 Hz, 1H), 6.73 (d, J=8.6 Hz, 1H), 5.49 (s, 1H), 4.75-4.60 (m, 1H), 4.23 (s, 1H), 4.15-4.05 (m, 1H), 4.05-3.85 (m, 1H), 0.80-0.65 (m, 2H), 0.65-0.50 (m, 2H). LCMS (Formic acid:$CH_3CN$): m/z: MH+=407, Rt=3.51 min. Chiral HPLC: Daicel Chiralpak IG, n-hexane/i-PrOH/TFA (70/30/0.1), Flow rate=1 mL/min, UV=210 nm, Rt=9.6 min (minor) and Rt=11.8 min (major). $[\alpha]_D^{25}$=+75.30° (c=0.51, dichloromethane).

c) Synthesis of the Enantiomer (3S,4S)—N-(3-cyano-4-fluorophenyl)-3-(6-cyclopropoxypyridin-3-yl)-1-oxo-2-(2,2,2-trifluoroethyl)-1,2,3,4-tetrahydroisoquinoline-4-carboxamide (1a) (Compound of Formula (I) Wherein X is CH and R is —O-Cyclopropyl) from the (+) Enantiomer of Trans-III-I'

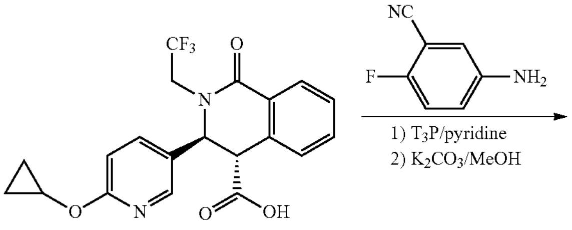

(III-1')

-continued

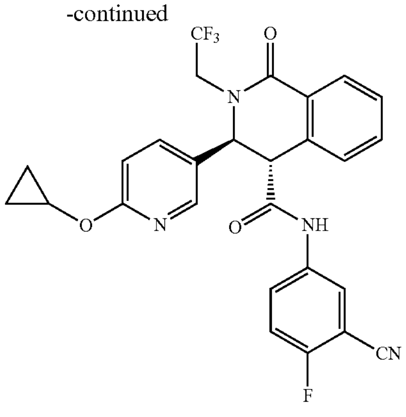

(+) Enantiomer of (1) = (1a)

Phosphoryl chloride (2.36 mL, 25.3 mmol) was added dropwise to a well stirred solution of (3S,4S)-3-(6-cyclopropoxypyridin-3-yl)-1-oxo-2-(2,2,2-trifluoroethyl)-1,2,3,4-tetrahydro isoquinoline-4-carboxylic acid (5.14 g, 12.65 mmol, >99% e.e.), 5-amino-2-fluorobenzonitrile (3.44 g, 25.3 mmol), DIPEA (4.0 mL, 38.0 mmol) and DMF (1.0 mL) in DCM (100 mL) at 0° C. then the reaction allowed to warm to room temperature. After 12 h the reaction was quenched by the addition of 1M hydrochloric acid (25 mL) then washed with saturated aqueous $NaHCO_3$ solution (2×50 mL) then brine (2×50 mL) then the organic phase dried ($MgSO_4$), filtered and concentrated in vacuo to give a white powder which was triturated from EtOAc, collected by filtration and dried to give compound (1a) as a white powder (5.17 g, 9.87 mmol, >99% e.e., 78%). 1H NMR (400 MHz, DMSO-d6) δ 10.78 (s, 1H), 8.10-7.95 (m, 3H), 7.86-7.80 (m, 1H), 7.58-7.42 (m, 4H), 7.30 (d, J=8.6 Hz, 1H), 6.80 (d, J=8.6 Hz, 1H), 5.39 (s, 1H), 4.68-4.56 (m, 1H), 4.24 (s, 1H), 4.14-4.07 (m, 1H), 4.06-3.92 (m, 1H), 0.75-0.65 (m, 2H), 0.65-0.55 (m, 2H). LCMS (Formic acid: $CH_3CN$): m/z: MH+525, Rt=1.68 min. $[\alpha]_D^{25}$=+101.210 (c=0.55, dichloromethane).

Synthesis of (+/−)-N-(3-cyano-4-fluorophenyl)-3-(6-isopropoxypyridin-3-yl)-1-oxo-2-(2,2,2-trifluoroethyl)-1,2,3,4-tetrahydroisoquinoline-4-carboxamide (2)

(E)-1-(6-methoxypyridin-3-yl)-N-(2,2,2-trifluoroethyl)methanimine (Intermediate of Formula (II-2))

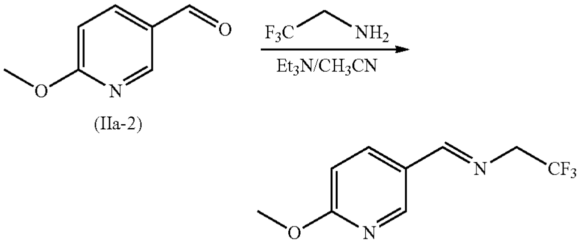

(IIa-2)

(II-2)

To a stirred solution of 6-Methoxynicotinaldehyde (IIa-2) (2.0 g, 14.6 mmol) in acetonitrile (15 ml) at 0° C. under nitrogen was added 2,2,2-trifluoroethanamine hydrochloride (6 g, 43.8 mmol) followed by triethylamine (6.0 ml, 43.8 mmol) and the reaction mixture was allowed to stir at room temperature for 48 h. After complete consumption of the starting material, according to NMR, the reaction was concentrated in vacuo, the residual oil diluted with diethyl ether (50 mL), dried ($MgSO_4$) and filtered. The filtrate was concentrated in vacuo to give the title compound (II-2) as a crude oil which was used in the next step without further purification.

Cis/trans-(+,−)-3-(6-methoxypyridin-3-yl)-1-oxo-2-(2,2,2-trifluoroethyl)-1,2,3,4-tetrahydroisoquinoline-4-carboxylic Acid (Intermediate of Formula (III-2))

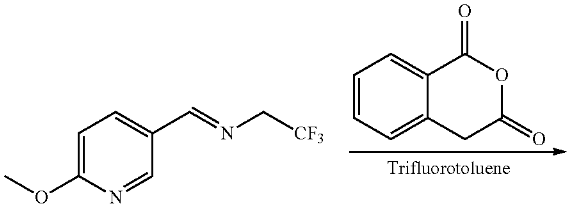

(II-2)

-continued

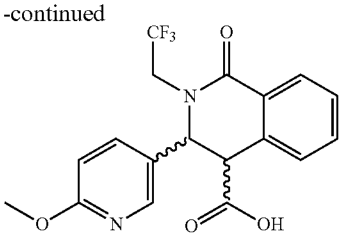

(III-2)

A stirred solution of crude (E)-1-(6-methoxypyridin-3-yl)-N-(2,2,2-trifluoroethyl)methanimine (1 g, 6.17 mmol) (II-2) in trifluorotoluene (10 ml) under nitrogen was treated with homophthalic anhydride (1.3 g, 6.18 mmol) and the reaction mixture heated with stirring at 130° C. for 16 h. The reaction mixture was then concentrated in vacuo to give a crude oil which was triturated from DCM/n-pentane to give the title compound (II-2) as a (1:1) mixture of cis and trans isomer which was used without further purification in the next step. LCMS (Formic acid:$CH_3CN$): m/z: MH+376, $R_t$=1.53 and 1.44 min.

(+, −)-N-(3-cyano-4-fluorophenyl)-3-(6-methoxy-pyridin-3-yl)-1-oxo-2-(2,2,2-trifluoro ethyl)-1,2,3,4-tetrahydroisoquinoline-4-carboxamide (Intermediate of Formula (IV-2))

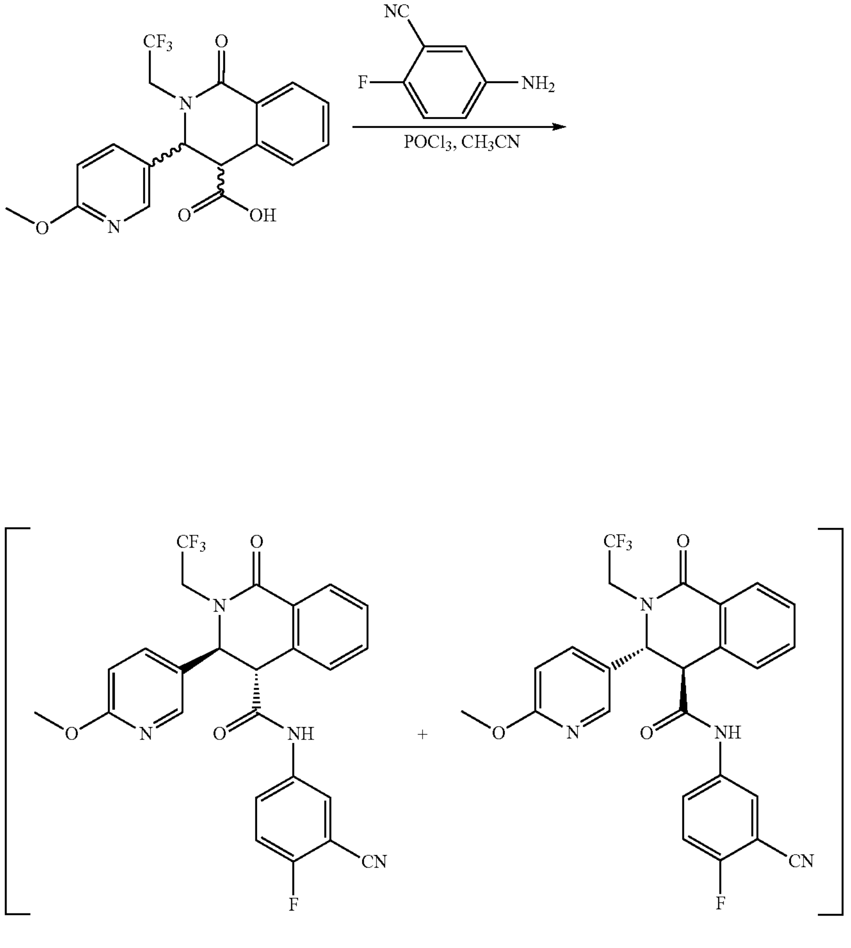

A stirred solution of crude (E)-1-(6-methoxypyridin-3-yl)-N-(2,2,2-trifluoroethyl)methanimine (II-2) (400 mg, 1.02 mmol) and 5-amino-2-fluorobenzonitrile (193 mg, 1.42 mmol) in acetonitrile (10 mL) under argon at 0° C. was treated with $POCl_3$ (0.11 ml, 1.15 mmol) and the reaction mixture was then heated to reflux for 2 h. The reaction mixture was concentrated in vacuo, diluted with ethyl acetate (25 mL), treated with saturated aqueous $NaHCO_3$ (10 mL), the organic phase separated, dried ($MgSO_4$), filtered and the filtrate concentrated in vacuo to give a crude oil. The crude compound was diluted with MeOH (10 mL), $K_2CO_3$ (700 mg, 5 mmol) added and the reaction mixture stirred at rt for 4 h, during which time the compound completely epimerized to the trans isomer. The reaction mixture was filtered through a celite bed, the filtrate concentrated in vacuo to give an oil which was subjected to column chromatography ($SiO_2$, 50-70% ethylacetate in hexane to 5% MeOH in DCM) to give racemic compound (IV-2) (200 mg, 0.4 mmol, 40%) as an off-white solid. $^1H$ NMR (400 MHz, DMSO-d6): δ 10.78 (s, 1H), 8.05-8.03 (m, 1H), 8.01 (d, J=7.12 Hz, 1H), 7.91 (s, 1H), 7.85-7.81 (m, 1H), 7.56-7.44 (m, 4H), 7.3 (d, J=8.08 Hz, 1H), 6.77 (d, J=8.68 Hz, 1H), 5.38 (s, 1H), 4.64-4.58 (m, 1H), 4.22 (s, 1H), 4.03-3.99 (m, 1H), 3.76 (s, 3H). LCMS (Formic acid:$CH_3CN$): m/z: MH+499, $R_t$=1.62 min.

(+, −)-N-(3-cyano-4-fluorophenyl)-3-(6-hydroxy-pyridin-3-yl)-1-oxo-2-(2,2,2-trifluoro ethyl)-1,2,3,4-tetrahydroisoquinoline-4-carboxamide (Intermediate of Formula (V-2))

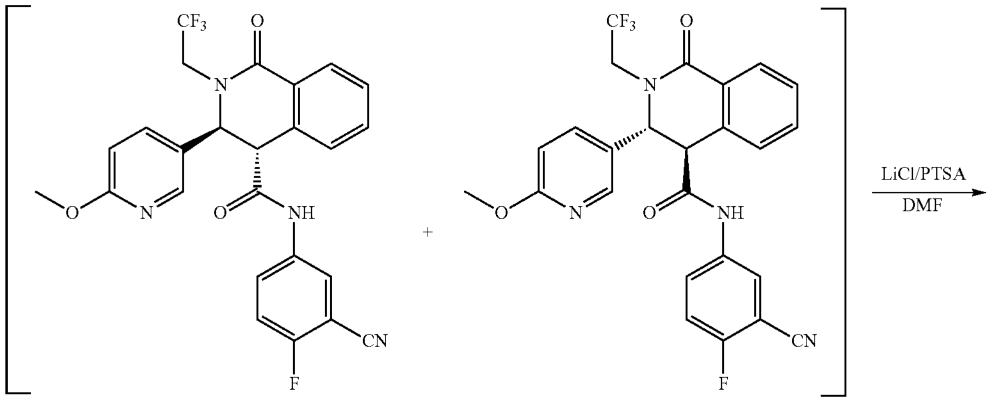

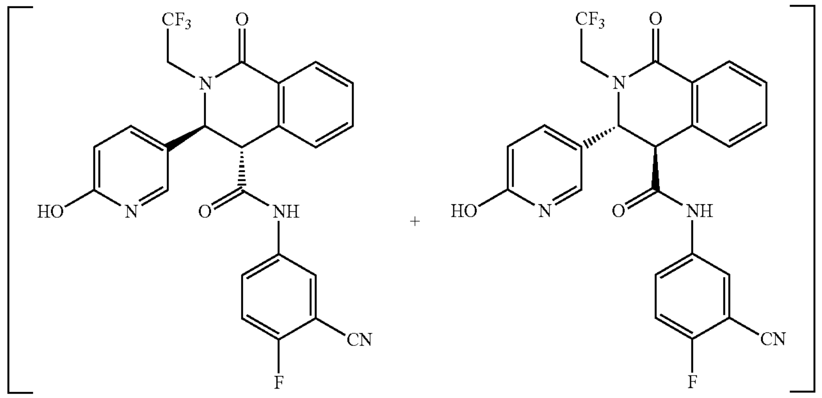

(V-2)

A solution of (rac)-N-(3-cyano-4-fluorophenyl)-3-(6-methoxypyridin-3-yl)-1-oxo-2-(2,2,2-trifluoroethyl)-1,2,3,4-tetrahydroisoquinoline-4-carboxamide (111-2) (180 mg, 0.36 mmol) in DMF (6 mL) was added treated with LiCl (76.6 mg, 1.81 mmol), followed by para-toluenesulfonic acid (311 mg, 1.81 mmol) and the reaction mixture heated with stirring at 120° C. in a microwave for 1 h. The cooled reaction mixture was diluted with ethyl acetate (20 mL), washed with water (10 mL), the organic phase dried ($Na_2SO_4$), filtered and concentrated in vacuo to give a crude oil which was purified by column chromatography ($SiO_2$, eluting with 7:3 ethylacetate:hexane) to give the title compound (V-2) (100 mg, 0.2 mmol, 57%) as an off-white solid.

$^1$H NMR (400 MHz, DMSO-d6): δ 11.47 (s, 1H), 10.75 (s, 1H), 8.03-7.98 (m, 2H), 7.83-7.80 (m, 1H), 7.56-7.48 (m, 3H), 7.35 (d, J=7.24 Hz, 1H), 7.23 (dd, J=9.24 Hz, 2 Hz, 1H), 7.00 (bs, 1H), 6.27 (d, J=9.56 Hz, 1H), 5.13 (s, 1H), 4.62-4.56 (m, 1H), 4.16 (s, 1H), 3.98-3.95 (m, 1H). LCMS (Formic acid:$CH_3CN$): m/z: MH+499, $R_t$=1.76 min.

(+, −)-N-(3-cyano-4-fluorophenyl)-3-(6-isopropoxy-pyridin-3-yl)-1-oxo-2-(2,2,2-trifluoro ethyl)-1,2,3,4-tetrahydroisoquinoline-4-carboxamide (2) (compound of Formula (I) wherein X is CH and R is O-isopropyl)

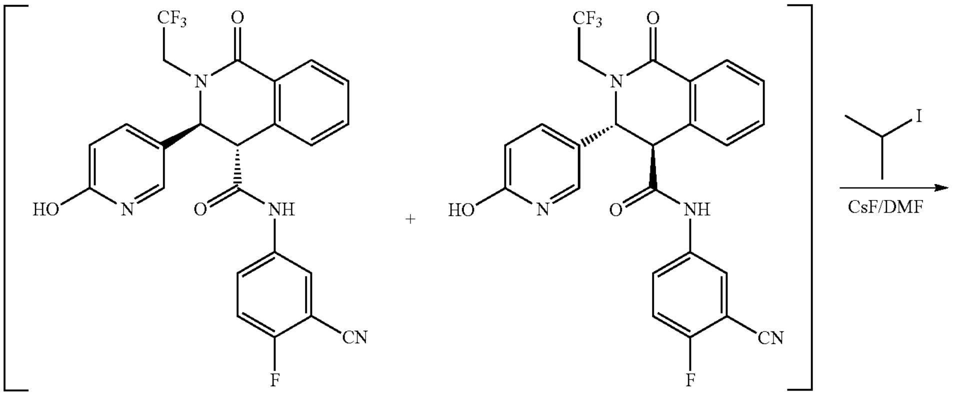

(V-2)

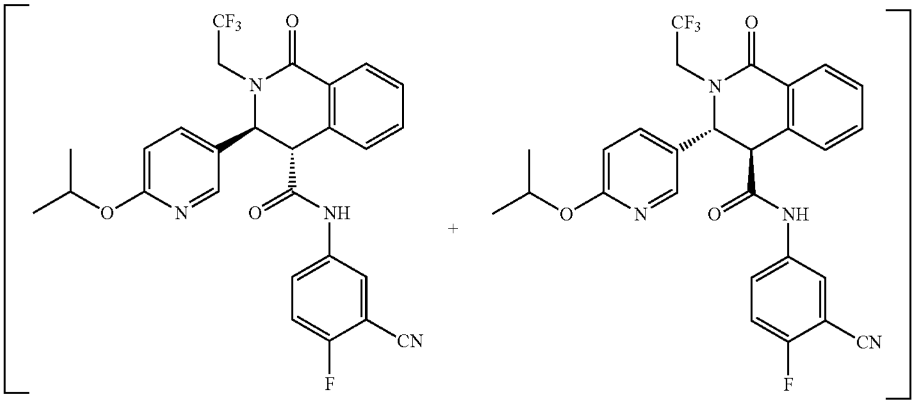

(2)

A solution of (rac)-N-(3-cyano-4-fluorophenyl)-3-(6-hydroxypyridin-3-yl)-1-oxo-2-(2,2,2-trifluoroethyl)-1,2,3,4-tetrahydroisoquinoline-4-carboxamide (V-2) (100 mg, 0.2 mmol), 2-iodopropane (0.1 mL) and CsF (94 mg, 0.6 mmol) in DMF (2 mL) was stirred at rt for 16 h. The reaction mixture was then diluted with ethyl acetate (25 mL), washed with water (10 mL) and brine (10 mL), then the organic phase dried ($Na_2SO_4$), filtered and concentrated in vacuo to give a crude oil which was subjected to reverse phase preparative HPLC chromatography to give the title compound (2) (25 mg, 0.16 mmol, 45%) as an off-white solid. $^1H$ NMR (400 MHz, DMSO-d6): δ 10.79 (s, 1H), 8.04-8.00 (m, 2H), 7.92 (s, 1H), 7.84-7.82 (m, 1H), 7.56-7.46 (m, 3H), 7.40 (d, J=9.92 Hz, 1H), 7.30 (d, J=7.16 Hz, 1H), 5.36 (s, 1H), 5.14-5.11 (m, 1H), 4.65-4.59 (m, 1H), 4.22 (s, 1H), 4.00-3.94 (m, 1H), 1.22 (s, 6H). LCMS (Formic acid: $CH_3CN$): m/z: MH+527, $R_t$=1.70 min.

Synthesis of (3S,4S)—N-(3-cyano-4-fluorophenyl)-1-oxo-2-(2,2,2-trifluoroethyl)-3-(6-(trifluoromethyl) pyridin-3-yl)-1,2,3,4-tetrahydroisoquinoline-4-carboxamide (3a)

(E)-N-(2,2,2-trifluoroethyl)-1-(6-(trifluoromethyl) pyridin-3-yl)methanimine (Intermediate of Formula (II-3))

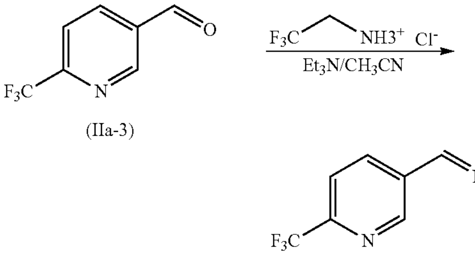

(IIa-3)

(II-3)

To a stirred solution of 2-(trifluoromethyl)pyridine-5-carboxaldehyde (IIa-3) (3.0 g, 17.1 mmol) in acetonitrile (100 mL) at 0° C. under nitrogen was added 2,2,2-trifluoroethanamine hydrochloride (6.9 g, 51.4 mmol), followed by triethylamine (7.2 mL, 51.4 mmol) and the reaction mixture stirred at rt for 48 h. The reaction was then concentrated in vacuo to give 3.5 g of the title compound (II-3) as a crude oil, which was used in the next step without further purification.

1-Oxo-2-(2,2,2-trifluoroethyl)-3-(6-(trifluoromethyl) pyridin-3-yl)-1,2,3,4-tetrahydro isoquinoline-4-carboxylic Acid (Intermediate of Formula (III-3))

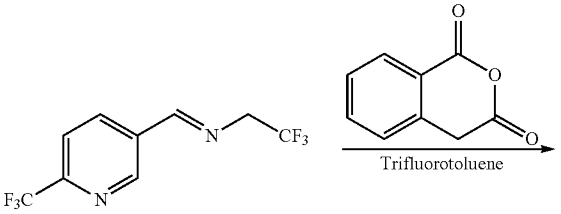

(II-3)

-continued

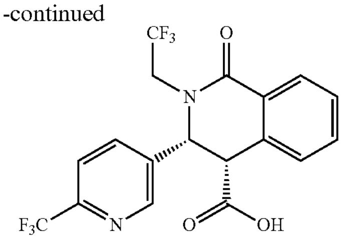

(III-3)

A stirred solution of crude (E)-N-(2,2,2-trifluoroethyl)-1-(6-(trifluoromethyl)pyridin-3-yl) methanimine (II-3) (3.0 g, 11.7 mmol) and homophthalic anhydride (1.9 g, 11.7 mmol) in trifluorotoluene (15 mL) under nitrogen was heated to 130° C. for 16 h. The reaction was then concentrated in vacuo to give 5.0 g of the crude title compound (III-3) as an approximate 1:1 mixture of cis and trans isomers, which was used in the next step without further purification.

(3S,4S)—N-(3-cyano-4-fluorophenyl)-1-oxo-2-(2,2,2-trifluoroethyl)-3-(6-(trifluoromethyl) pyridin-3-yl)-1,2,3,4-tetrahydroisoquinoline-4-carboxamide (3a) (Compound of Formula (I) Wherein X is CH and R is $CF_3$)

To a stirred solution of (rac)-1-oxo-2-(2,2,2-trifluoroethyl)-3-(6-(trifluoromethyl)pyridin-3-yl)-1,2,3,4-tetrahydroisoquinoline-4-carboxylic acid (II-3) (2.0 g, 4.78 mmol) in pyridine (30 ml) at rt under nitrogen was added propylphosphonic anhydride (50% solution in ethyl acetate, 28.0 ml, 47.8 mmol), followed by 5-amino-2-fluorobenzonitrile (0.7 g, 5.23 mmol) and the reaction heated at 50° C. for 16 h. The reaction mixture was then cooled to rt, diluted with ethyl acetate (50 mL), washed with $CuSO_4$ solution (3×10 mL), dried ($MgSO_4$), filtered and the filtrate concentrated in vacuo.

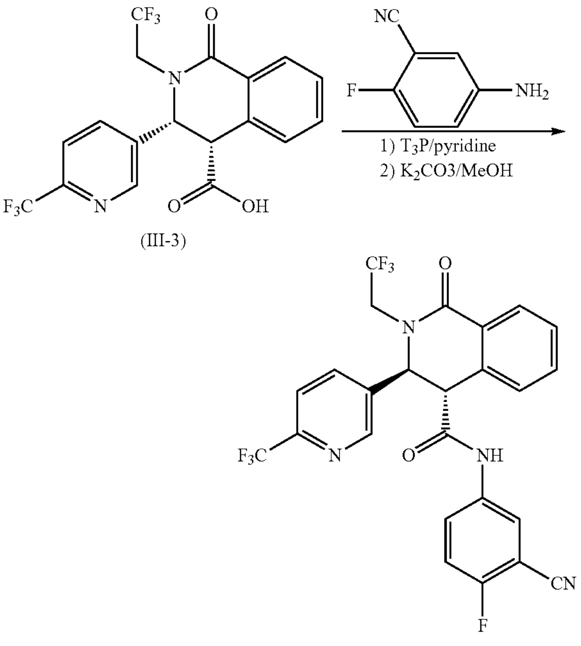

(III-3)

(3a)

The resulting oil was diluted with MeOH (20 mL) and stirred with $K_2CO_3$ (3.3 g, 24.0 mmol) for 4 h during which time the trans epimer was formed exclusively, according to NMR. The suspension was then filtered through a bed of celite, concentrated in vacuo and the resulting oil subjected to chromatography ($SiO_2$, 3:7 ethyl acetate:hexane) to give the title compound (3) as a racemate (1.0 g, 1.86 mmol, 39%). The (+)-enantiomer was obtained by preparative chiral HPLC (column: Chiralpak IA, 21×250 mm, 5μ. particle size, operating at ambient temperature and flow rate of 21 ml/min. Wave length: 222 nm, run time 20 min. Mobile phase: Hexane/Dichloromethane/EtOH:70/15/15), followed by lyophilization to give 200 mg of the title compound (3S,4S)—N-(3-cyano-4-fluorophenyl)-1-oxo-2-(2,2,2-trifluoroethyl)-3-(6-(trifluoromethyl)pyridin-3-yl)-1,2,3,4-tetrahydro isoquinoline-4-carboxamide (3a) >99% e.e. $^1H$ NMR (400 MHz, DMSO-d6): δ 10.88 (s, 1H), 8.72 (s, 1H), 8.06-8.00 (m, 2H), 7.87-7.82 (m, 2H), 7.74 (d, J=7.12 Hz, 1H), 7.57-7.47 (m, 3H), 7.29 (d, J=6.28 Hz, 1H), 5.64 (s, 1H), 4.66-4.58 (m, 1H), 4.35 (s, 1H), 4.20-4.09 (m, 1H). LCMS (Formic acid:$CH_3CN$): m/z: MH+537, Rt=1.68. $[\alpha]_D^{25}$=+59.07° (c=0.536, chloroform).

Synthesis of (3S,4S)—N-(3-cyano-4-fluorophenyl)-1-oxo-3-(6-(2,2,2-trifluoro ethoxy)pyridin-3-yl)-2-(2,2,2-trifluoroethyl)-1,2,3,4-tetrahydro isoquinoline-4-carboxamide (4a)

(E)-1-(6-(2,2,2-Trifluoroethoxy)pyridin-3-yl)-N-(2,2,2-trifluoroethyl)methanimine (Intermediate of Formula (II-4))

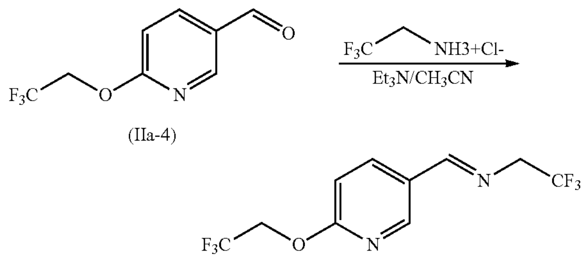

(IIa-4)

(II-4)

To a stirred solution of 2-(trifluoromethyl)pyrimidine-5-carbaldehyde (IIa-4) (2.0 g, 9.8 mmol) in acetonitrile (50 mL) at 0° C. under nitrogen was added 2,2,2-trifluoroethyl amine (6.5 g, 39.2 mmol) and the reaction mixture was allowed to stir at rt for 48 h. The reaction mixture was then concentrated in vacuo to give 2.7 g of the crude tile compound (II-4) as a colourless oil which was used in the next step without further purification.

1-Oxo-3-(6-(2,2,2-Trifluoroethoxy)pyridin-3-yl)-2-(2,2,2-trifluoroethyl)-1,2,3,4-tetrahydroisoquinoline-4-carboxylic Acid (Intermediate of Formula (III-4))

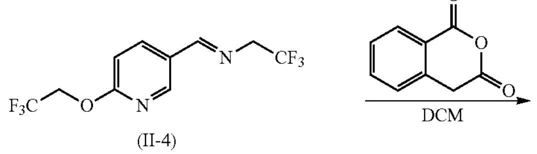

(II-4)

-continued

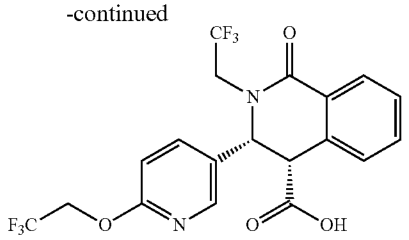

(III-4)

To a stirred solution of crude (E)-1-(6-(2,2,2-trifluoroethoxy)pyridin-3-yl)-N-(2,2,2-trifluoroethyl)methanimine (II-4) (1.8 g, 6.28 mmol) in dichloromethane (25 mL) under nitrogen was added homophthalic anhydride (1.12 g, 6.9 mmol) and the reaction mixture was allowed to stir at room temperature for 16 h. The reaction mixture was then concentrated in vacuo to give 2.0 g of the crude tile compound (III-4) as an approximately 1:1 mixture of cis and trans isomer as a colourless oil which was used in the next step without further purification. LCMS (Formic acid:$CH_3CN$): m/z: MH+449, $R_t$=1.83 min.

(3S,4S)—N-(3-cyano-4-fluorophenyl)-1-oxo-3-(6-(2,2,2-trifluoroethoxy)pyridin-3-yl)-2-(2,2,2-trifluoroethyl)-1,2,3,4-tetrahydroisoquinoline-4-carboxamide (4a) (Compound of Formula (I) Wherein X is CH and R is $OCH_2CF_3$)

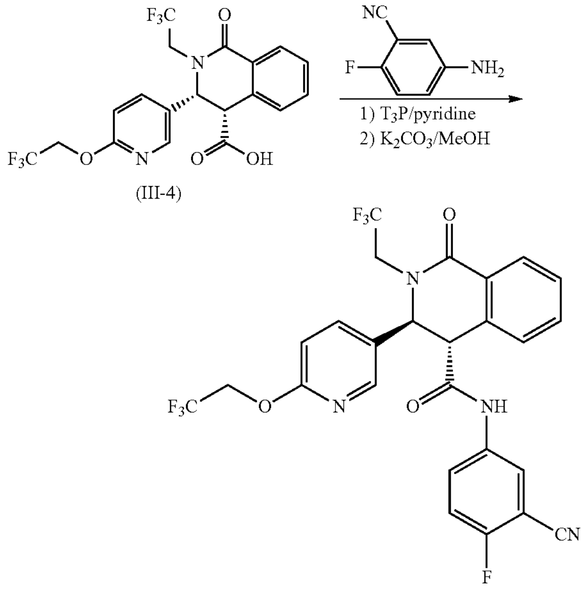

(III-4)

(4a)

To a stirred solution of 1-oxo-3-(6-(2,2,2-trifluoroethoxy) pyridin-3-yl)-2-(2,2,2-trifluoroethyl)-1,2,3,4-tetrahydroisoquinoline-4-carboxylic acid (III-4) (1 g, 2.23 mmol) in pyridine (10.0 ml) at rt was added propylphosphonic anhydride (50% solution in ethyl acetate, 13 ml, 22.3 mmol). Then to the mixture was added 5-amino-2-fluorobenzonitrile (0.42 g, 3.12 mmol) and the reaction mixture was heated at 50° C. with continued stirring for 16 h. The reaction mixture was then cooled to rt, diluted with ethyl acetate (50 mL), washed with $CuSO_4$ solution (3×10 mL), dried ($MgSO_4$), filtered and the filtrate concentrated in vacuo. The resulting oil was diluted with MeOH (20 mL) and stirred with $K_2CO_3$ (1.5 g, 10.9 mmol) for 4 h during which time the trans epimer was formed exclusively, according to NMR. The suspension was then filtered through a bed of celite, concentrated in vacuo and the resulting oil subjected to chromatography ($SiO_2$, 3:7 ethyl acetate:hexane) to give the title compound (4) as a racemate (700 mg, 1.33 mmol, 55%). The (+)-enantiomer was obtained by preparative chiral HPLC (column: Chiralpak IA, 21×250 mm, 5μ particle size, operating at ambient temperature and flow rate of 21 ml/min. Wave length: 222 nm, run time 20 min. Mobile phase: Hexane/Dichloromethane/EtOH:70/15/15), followed by lyophilization to give 250 mg of the title compound (4a) >99% e.e. $^1H$ NMR (400 MHz, DMSO-d6): δ 10.81 (s, 1H), 8.06-7.94 (m, 3H), 7.85-7.80 (m, 1H), 7.60-7.44 (m, 4H), 7.30 (d, J=6.72 Hz, 1H), 6.95 (d, J=8.6 Hz, 1H), 5.43 (s, 1H), 4.94-4.87 (m, 2H), 4.63-4.57 (m, 1H), 4.23 (s, 1H), 4.09-4.03 (m, 1H). LCMS (Formic acid:$CH_3CN$): m/z: MH+567, Rt=1.75 min. $[\alpha]_D^{25}$=+69.12° (c=0.37, dichloromethane).

Synthesis of (3S,4S)-3-(6-acetamidopyridin-3-yl)-N-(3-cyano-4-fluorophenyl)-1-oxo-2-(2,2,2-trifluoroethyl)-1,2,3,4-tetrahydroisoquinoline-4-carboxamide (5a)

(E)-N-(5-(((2,2,2-trifluoroethyl)imino)methyl)pyridin-2-yl)acetamide (Intermediate of Formula (II-5))

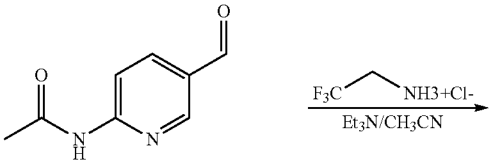

(IIa-5)

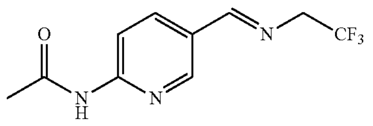

(II-5)

To a stirred solution of N-(5-Formylpyridin-2-yl)acetamide (IIa-5) (50 mg, 0.3 mmol) in acetonitrile (2 mL) at 0° C. under nitrogen was added 2,2,2-trifluoroethanamine hydrochloride (123 mg, 0.9 mmol) followed by triethylamine (127 μL, 0.9 mmol) and the reaction mixture was allowed to stir at rt for 48 h. The reaction was then concentrated in vacuo and the resulting slurry was diluted with diethylether (20 mL), filtered, then concentrated in vacuo to give the title compound (II-5) as a crude colourless oil which was used in the next step without further purification.

3-(6-Acetamidopyridin-3-yl)-1-oxo-2-(2,2,2-trifluoroethyl)-1,2,3,4-tetrahydro isoquinoline-4-carboxylic Acid (Intermediate of Formula (III-5))

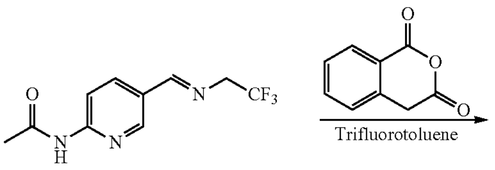

(II-5)

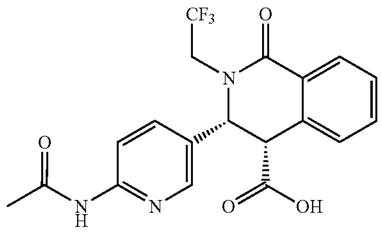

(III-5)

To a stirred solution of crude (E)-N-(5-(((2,2,2-trifluoroethyl)imino)methyl)pyridin-2-yl)acetamide (II-5) (50 mg, 0.2 mmol) in trifluorotoluene (5 mL) under nitrogen was added homophthalic anhydride (33 mg, 0.2 mmol) and the reaction mixture heated to 100° C. for 16 h. The reaction mixture was then concentrated in vacuo to give a slurry which was triturated with n-pentane/DCM and filtered to give the title compound (III-5) as an approximately 1:1 mixture of cis and trans isomer, which was used in the next step without further purification.

(3S,4S)-3-(6-acetamidopyridin-3-yl)-N-(3-cyano-4-fluorophenyl)-1-oxo-2-(2,2,2-trifluoroethyl)-1,2,3,4-tetrahydroisoquinoline-4-carboxamide (5a) (Compound of Formula (I) Wherein X is CH and R is $NHC(=O)CH_3$)

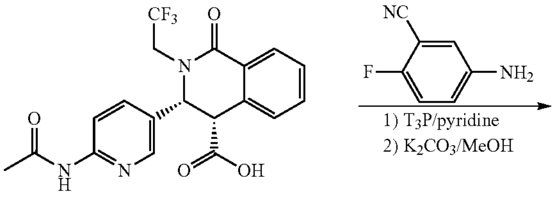

(III-5)

-continued

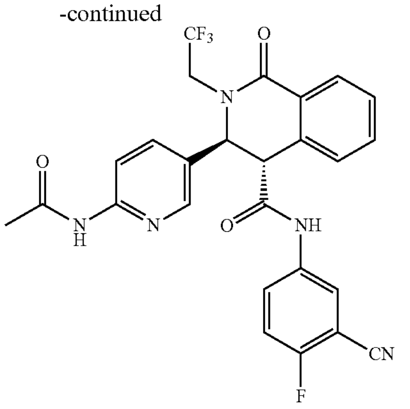

(5a)

To a stirred solution of 3-(6-acetamidopyridin-3-yl)-1-oxo-2-(2,2,2-trifluoroethyl)-1,2,3,4-tetrahydroisoquinoline-4-carboxylic acid (95 mg, 0.22 mmol) in pyridine (5 mL) under nitrogen was added propylphosphonic anhydride (0.7 ml, 2.2 mmol) followed by 5-amino-2-fluorobenzonitrile (48 mg, 0.35 mmol) and the reaction mixture heated to 50° C. for 16 h. The reaction mixture was then cooled to rt, diluted with ethyl acetate (50 mL), washed with $CuSO_4$ solution (3×10 mL), dried ($MgSO_4$), filtered and the filtrate concentrated in vacuo. The resulting oil was diluted with MeOH (5 mL) and stirred with $K_2CO_3$ (152 mg, 1.1 mmol) for 4 h during which time the trans epimer was formed exclusively, according to NMR. The suspension was then filtered through a bed of celite, concentrated in vacuo and the resulting oil subjected to chromatography ($SiO_2$, 3:7 ethyl acetate: hexane) to give the title compound (5) as a racemate (20 mg, 0.04 mmol, 12%). The (+)-enantiomer was obtained by preparative chiral HPLC (column: Chiralpak IA, 21×250 mm, 5μ. particle size, operating at ambient temperature and flow rate of 21 ml/min. Wave length: 222 nm, run time 20 min. Mobile phase: Hexane/Dichloromethane/EtOH:70/15/15), followed by lyophilization to give 8 mg of the title compound (5a) as a pale yellow solid >99% e.e. $^1$H NMR (400 MHz, DMSO-d6): δ 10.80 (s, 1H), 10.46 (s, 1H), 8.10 (s, 1H), 8.06-8.04 (m, 1H), 8.01 (d, J=8.28 Hz, 1H), 7.92 (d, J=8.72 Hz, 1H), 7.85-7.81 (m, 1H), 7.56-7.44 (m, 4H), 7.28 (d, J=6.68 Hz, 1H), 5.41 (s, 1H), 4.65-4.56 (m, 1H), 4.26 (s, 1H), 4.07-4.01 (m, 1H), 2.03 (s, 3H). LCMS (Formic acid:$CH_3CN$): m/z: MH+526, Rt=1.55 min. [α]$D^{25}$=+137.5° (c=0.28, EtOAc).

Synthesis of (3S,4S)—N-(3-cyano-4-fluorophenyl)-3-(6-cyanopyridin-3-yl)-1-oxo-2-(2,2,2-trifluoroethyl)-1,2,3,4-tetrahydroisoquinoline-4-carboxamide (6a)

(E)-5-(((2,2,2-trifluoroethyl)imino)methyl)picolinonitrile (Intermediate of Formula (II-6))

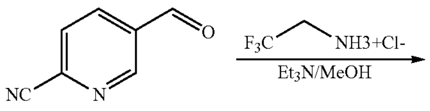

(IIa-6)

-continued

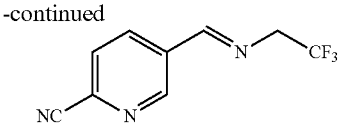

(II-6)

To a stirred solution of 5-formyl-2-pyridinecarbonitrile (IIa-6) (200 mg, 1.5 mmol) in methanol (6 mL) at 0° C. under nitrogen was added 2,2,2-trifluoroethanamine hydrochloride (818 mg, 6 mmol) followed by triethylamine (1.26 mL, 9 mmol) and the reaction mixture was allowed to stir at room temperature for 48 h. The reaction was then concentrated in vacuo and the resulting slurry was diluted with diethylether (20 mL), filtered, then concentrated in vacuo to give the title compound (II-6) as a crude colourless oil which was used in the next step without further purification.

3-(6-Cyanopyridin-3-yl)-1-oxo-2-(2,2,2-trifluoroethyl)-1,2,3,4-tetrahydroisoquinoline-4-carboxylic Acid (Intermediate of Formula (III-6)

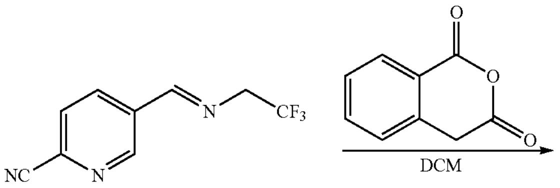

(II-6)

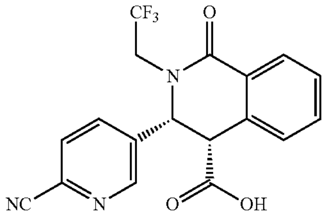

(III-6)

To a stirred solution of crude (E)-5-(((2,2,2-trifluoroethyl)imino)methyl)picolinonitrile (II-6) (70 mg, 0.33 mmol) in dichloromethane (5 mL) under nitrogen was added homophthalic anhydride (74 mg, 0.46 mmol) and the reaction mixture was allowed to stir at rt for 16 h. The reaction was then concentrated in vacuo to give a slurry which was triturated with n-pentane/DCM and filtered to give the title compound (III-6) as an approximate 1:1 mixture of cis and trans isomers which was used in the next step without further purification. LCMS (Formic acid:$CH_3CN$): m/z: MH+376, $R_t$=1.44 min.

(3S,4S)—N-(3-cyano-4-fluorophenyl)-3-(6-cyano-pyridin-3-yl)-1-oxo-2-(2,2,2-trifluoro ethyl)-1,2,3,4-tetrahydroisoquinoline-4-carboxamide (6a) (Compound of Formula (I) Wherein X is CH and R is CN)

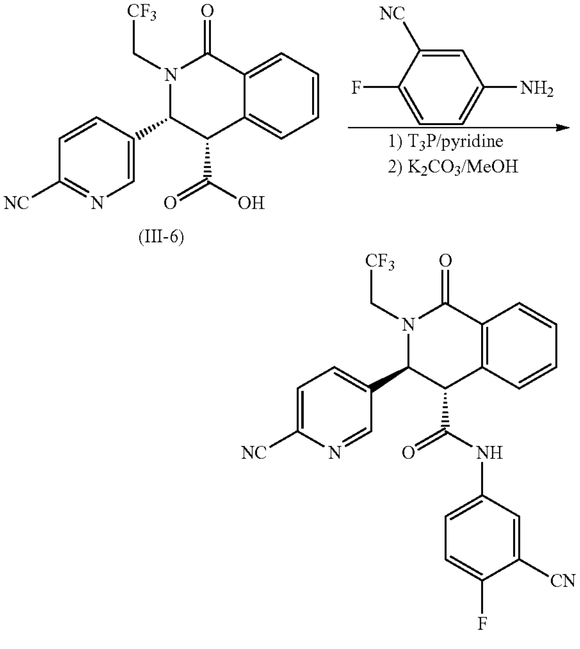

(III-6)
(6a)

To a stirred solution of crude 3-(6-cyanopyridin-3-yl)-1-oxo-2-(2,2,2-trifluoroethyl)-1,2,3,4-tetrahydroisoquinoline-4-carboxylic acid (III-6) (140 mg, 0.37 mmol) in pyridine (2 mL) under nitrogen was added propylphosphonic anhydride (50% solution in ethyl acetate, 1.1 mL, 3.77 mmol) followed by 5-amino-2-fluorobenzonitrile (61 mg, 0.45 mmol) and the reaction heated to 50° C. for 16 h. The reaction mixture was then cooled to rt, diluted with ethyl acetate (50 mL), washed with $CuSO_4$ solution (3×10 mL), dried ($MgSO_4$), filtered and the filtrate concentrated in vacuo. The resulting oil was diluted with MeOH (4 mL) and stirred with $K_2CO_3$ (255 mg, 1.85 mmol) for 4 h during which time the trans epimer was formed exclusively, according to NMR. The suspension was then filtered through a bed of celite, concentrated in vacuo and the resulting oil subjected to chromatography ($SiO_2$, 3:7 ethyl acetate:hexane) to give the title compound (6) as a racemate (82 mg, 0.16 mmol, 45%). The (+)-enantiomer was obtained by preparative chiral HPLC (column: Chiralpak IA, 21×250 mm, 5μ particle size, operating at ambient temperature and flow rate of 21 ml/min. Wave length: 222 nm, run time 20 min. Mobile phase: Hexane/Dichloromethane/EtOH:70/15/15), followed by lyophilization to give 27 mg of the title compound (6a) as an off-white solid >99% e.e. $^1$H NMR (400 MHz, DMSO-d6): δ 10.84 (s, 1H), 8.73 (s, 1H), 8.05-7.96 (m, 3H), 7.84-7.82 (m, 1H), 7.68 (d, J=6.48 Hz, 1H), 7.57-7.45 (m, 3H), 7.29 (d, J=6.04 Hz, 1H), 5.63 (s, 1H), 4.65-4.59 (m, 1H), 4.32 (s, 1H), 4.17-4.11 (m, 1H). LCMS (Formic acid:$CH_3CN$): m/z: MH+492, Rt=1.74 min. [α]D$^{25}$=+108.5° (c=0.25, DMSO).

Synthesis of (3S,4S)—N-(3-cyano-4-fluorophenyl)-3-(6-(difluoromethoxy)pyridin-3-yl)-1-oxo-2-(2,2,2-trifluoroethyl)-1,2,3,4-tetrahydroisoquinoline-4-carboxamide (7a) 6-(Difluoromethoxy)nicotinaldehyde (Intermediate of Formula (Intermediate of Formula (IIa-7))

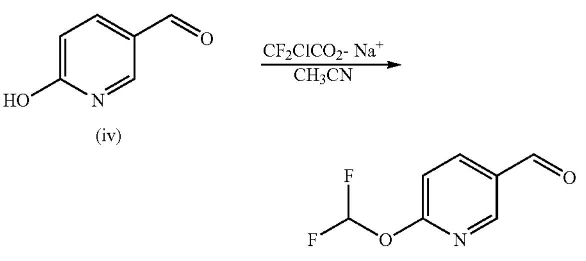

(iv)
(IIa-7)

To a stirred solution of 6-hydroxynicotinaldehyde (iv) (2.0 g, 16.2 mmol) in acetonitrile (60 mL) at rt under nitrogen was added sodium chlorodifluoroacetate (3.7 g, 24.4 mmol). The reaction mixture was heated at 85° C. for 72 h then the reaction was quenched by the addition of distilled water (10 mL) and the mixture extracted with ethylacetate (3×20 mL), the combined extracts dried ($Na_2SO_4$), filtered and concentrated in vacuo and the resulting white gum subjected to column chromatography ($SiO_2$, 1:5 ethyl acetate:hexane) to give the title compound (IIa-7) (1.8 g, 10.4 mmol, 64%) as an off-white solid. $^1$H NMR (400 MHz, DMSO-d6): δ 10.06 (s, 1H), 8.84 (s, 1H), 8.34 (dd, J=8.52, Hz, 2.16 Hz, 1H), 8.01-7.65 (m, 1H), 7.28 (d, J=8.56 Hz, 1H).

(E)-1-(6-(difluoromethoxy)pyridin-3-yl)-N-(2,2,2-trifluoroethyl)methanimine (Intermediate of Formula (II-7))

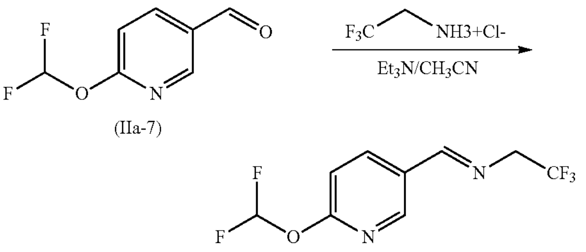

(IIa-7)
(II-7)

To a stirred solution of 6-(difluoromethoxy)nicotinaldehyde (IIa-7) (500 mg, 2.89 mmol) in acetonitrile (20 ml) at 0° C. under nitrogen was added 2,2,2-trifluoroethanamine hydrochloride (1.5 g, 11.5 mmol), followed by triethylamine (2.4 ml, 17.3 mmol) and the reaction mixture stirred at rt for 48 h. The reaction was concentrated in vacuo to give the title compound (II-7) as a crude oil which was used in the next step without further purification.

3-(6-(Difluoromethoxy)pyridin-3-yl)-1-oxo-2-(2,2,2-trifluoroethyl)-1,2,3,4-tetrahydro isoquinoline-4-carboxylic Acid (Intermediate of Formula (III-7))

To a stirred solution of (E)-1-(6-(difluoromethoxy)pyridin-3-yl)-N-(2,2,2-trifluoroethyl)methanimine (II-7) (1.1 g, 4.3 mmol) in dichloromethane (20 mL) under nitrogen at rt was added homophthalic anhydride (0.7 g, 4.3 mmol) and the reaction mixture was stirred for 16 h. Concentration of the mixture in vacuo gave 2 g of crude material (III-7) which was used in the next step without further purification.

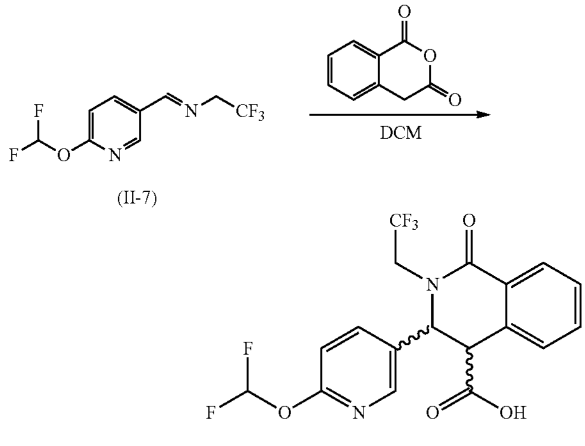

(II-7)

(III-7)

(3S,4S)—N-(3-cyano-4-fluorophenyl)-3-(6-(difluoromethoxy)pyridin-3-yl)-1-oxo-2-(2,2,2-trifluoroethyl)-1,2,3,4-tetrahydroisoquinoline-4-carboxamide (7a) (Compound of Formula (I) wherein X is CH and R is $OCHF_2$)

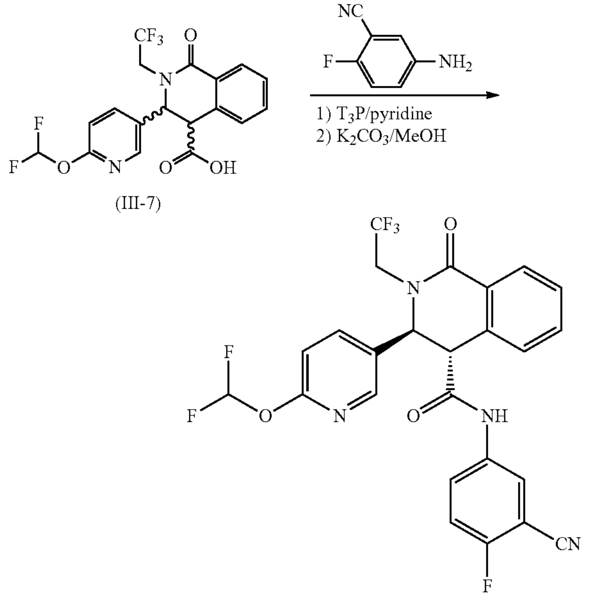

(III-7)

(7a)

To a stirred solution of crude 3-(6-(difluoromethoxy)pyridin-3-yl)-1-oxo-2-(2,2,2-trifluoroethyl)-1,2,3,4-tetrahydroisoquinoline-4-carboxylic acid (III-7) (2 g, 4.8 mmol) in pyridine (30 mL) at rt under nitrogen was added propylphosphonic anhydride (50% solution in ethyl acetate, 30.0 ml, 48.1 mmol) followed by 5-amino-2-fluorobenzonitrile (0.78 g, 5.8 mmol) and the reaction heated to 50° C. for 16 h. The reaction mixture was then cooled to rt, diluted with ethyl acetate (50 mL), washed with $CuSO_4$ solution (3×10 mL), dried ($MgSO_4$), filtered and the filtrate concentrated in vacuo. The resulting oil was diluted with MeOH (50 mL) and stirred with $K_2CO_3$ (1.0 g, 7.25 mmol) for 4 h during which time the trans epimer was formed exclusively, according to NMR. The suspension was then filtered through a bed of celite, concentrated in vacuo and the resulting oil subjected to chromatography ($SiO_2$, 3:7 ethylacetate: hexane) to give the title compound (7) as a racemate (1.1 g, 2.06 mmol, 42%). The (+)-enantiomer was obtained by preparative chiral HPLC (column: Chiralpak IA, 21×250 mm, 5μ particle size, operating at ambient temperature and flow rate of 21 ml/min. Wave length: 222 nm, run time 20 min. Mobile phase: Hexane/Dichloromethane/EtOH: 70/15/15), followed by lyophilization to give 205 mg of the title compound (7a) as an off-white solid >99% e.e. $^1H$ NMR (400 MHz, DMSO-d6): δ 10.82 (s, 1H), 8.06-8.00 (m, 3H), 7.84-7.82 (m, 1H), 7.70-7.45 (m, 4H), 7.31 (d, J=6.92 Hz, 1H), 7.06 (d, J=8.52 Hz, 1H), 5.49 (s, 1H), 4.64-4.58 (m, 1H), 4.26 (s, 1H), 4.11-4.05 (m, 1H). LCMS (Formic acid:$CH_3CN$): m/z: MH+536, $R_t$=1.68 min. $[\alpha]_D^{25}$=+56.38° (c 0.418, dichloromethane).

Synthesis of (3S,4S)—N-(3-cyano-4-fluorophenyl)-3-(6-(difluoromethyl)pyridin-3-yl)-1-oxo-2-(2,2,2-trifluoroethyl)-1,2,3,4-tetrahydroisoquinoline-4-carboxamide (8a) 5-Bromo-2-(difluoromethyl)pyridine (Intermediate of Formula (vi))

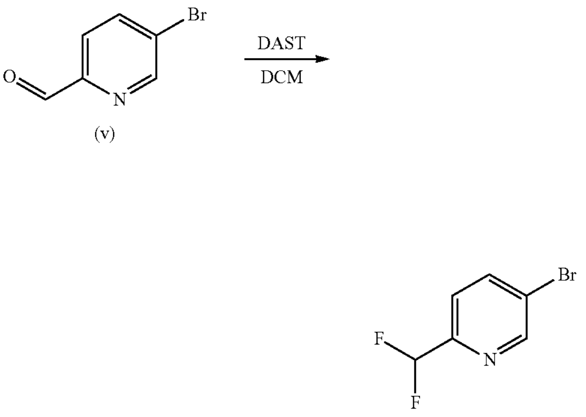

(v)

(vi)

To a stirred solution of 5-bromo-2-formylpyridine (v) (10.0 g, 53.8 mmol) in dichloromethane (100 mL) at −78° C. under nitrogen was added diethyl amino sulfur trifluoride (DAST) (15.6 ml, 118.3 mmol). The reaction mixture was allowed to warm slowly to rt then stirred for a further 6 h. The reaction mixture was then diluted with dichloromethane (100 mL), washed with saturated aqueous sodium bicarbonate solution (3×50 mL) and brine (2×50 mL), dried ($MgSO_4$), filtered and concentrated in vacuo to give an oil which was subjected to chromatography ($SiO_2$, 1:5 ethylacetate:hexanes) to give the title compound (vi) (5.6 g, 27.2 mmol, 50%) as a colourless oil. $^1H$ NMR (400 MHz, $CDCl_3$): δ 8.71 (s, 1H), 7.97 (d, J=8.36 Hz, 1H), 7.53 (d, J=8.28 Hz, 1H), 6.73-6.45 (m, 1H).

Methyl 6-(difluoromethyl)nicotinate (Intermediate of Formula (ii-8))

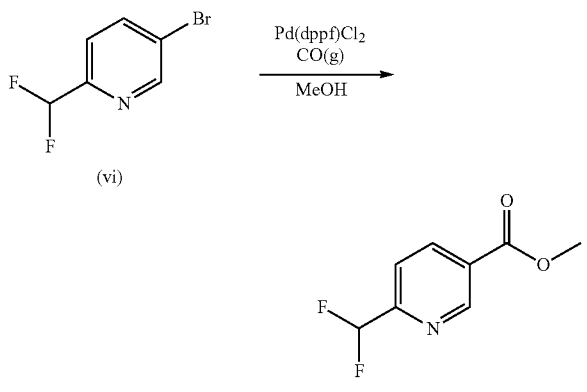

(vi)

(ii-8)

A solution of 5-bromo-2-(difluoromethyl)pyridine (v) (5 g, 24.03 mmol) in MeOH (50 mL) under an atmosphere of carbon monoxide was treated with triethylamine (10 mL, 72 mmol) followed by 1,1'-bis-(diphenylphosphino)-ferrocene dichloropalladium (II) (1.7 g, 2.4 mmol) and heated at 80° C. and 60 PSI for 6 h in an autoclave. The reaction mixture was then allowed to cool and filtered through a bed of celite, the filtrate concentrated in vacuo to give a slurry which was subjected to chromatography ($SiO_2$, 1:5 ethylacetate: hexane) to give the title compound (ii-8) (2.9 g, 15.5 mmol, 64%) as a brown gum. $^1H$ NMR (400 MHz, $CDCl_3$): δ 9.23 (s, 1H), 8.44 (d, J=8.08 Hz, 1H), 7.72 (d, J=8.12 Hz, 1H), 6.80-6.53 (m, 1H), 3.97 (s, 1H). LCMS (Formic acid: $CH_3CN$): m/z: MH+188, $R_t$=1.43 min.

(6-(Difluoromethyl)pyridin-3-yl)methanol (Intermediate of Formula (iii-8))

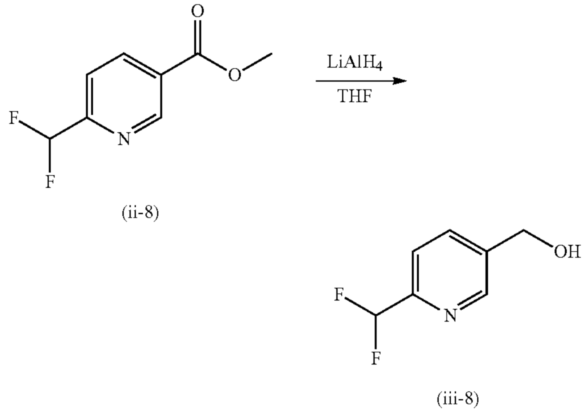

(ii-8)

(iii-8)

To a stirred solution of methyl 6-(difluoromethyl)nicotinate (ii-8) (2.0 g, 10.7 mmol) in THE (25 mL) at 0° C. under nitrogen was gradually added a 1M solution of lithium aluminum hydride in THE (21.0 ml, 21.0 mmol). After 2 h at 0° C. the starting material had been completely consumed and the reaction was quenched by the slow addition of 5 mL of saturated aqueous sodium sulphate solution. The crude reaction mixture was then filtered through a bed of celite, the filtrate concentrated in vacuo and the resulting residue subjected to chromatography ($SiO_2$, 1:1 ethylacetate: hexanes) to give the title compound (iii-8) (1.6 g, 10.0 mmol, 94%) as a white waxy solid. $^1H$ NMR (400 MHz, $CDCl_3$): δ 8.60 (s, 1H), 7.85 (d, J=7.68 Hz, 1H), 7.62 (d, J=7.96 Hz, 1H), 6.76-6.48 (m, 1H), 4.78 (s, 2H). LCMS (Formic acid:$CH_3CN$): m/z: MH+160, $R_t$=1.19 min.

6-(Difluoromethyl)nicotinaldehyde (Intermediate of Formula (IIa-8))

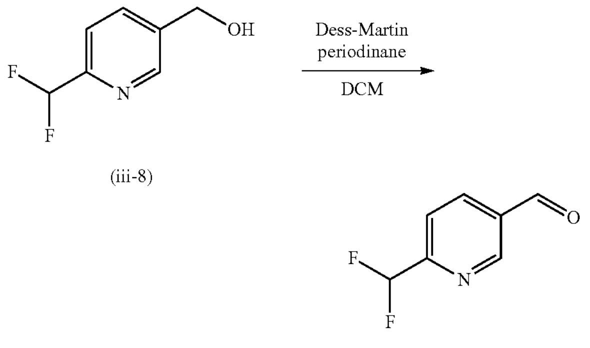

(iii-8)

(IIa-8)

To a stirred solution of (6-(difluoromethyl)pyridin-3-yl) methanol (iii-8) (1.5 g, 9.5 mmol) in dichloromethane (50 mL) at 0° C. under nitrogen was added Dess-Martin periodinane (8.0 g, 19.0 mmol) and the reaction mixture was gradually allowed to warm to rt over 2 h. The reaction mixture was then filtered through a bed of celite bed, the filtrate concentrated in vacuo and the resulting oil subjected to chromatography ($SiO_2$, 1:5 ethylacetate:hexanes) to give the title compound (IIa-8) (700 mg, 4.45 mmol, 47%) as a colorless liquid. $^1H$ NMR (400 MHz, DMSO-d6): δ 10.17 (s, 1H), 9.17 (s, 1H), 8.45 (d, J=8.04 Hz, 1H), 7.92 (d, J=8.00 Hz, 1H), 7.21-6.94 (m, 1H). LCMS (Formic acid:$CH_3CN$): m/z: MH+158, $R_t$=1.17 min.

(E)-1-(6-(Difluoromethyl)pyridin-3-yl)-N-(2,2,2-trifluoroethyl)methanimine (Intermediate of Formula (II-8))

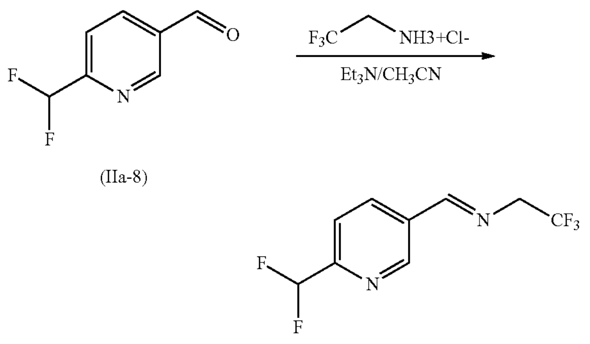

(IIa-8)

(II-8)

To a stirred solution of 6-(difluoromethyl)nicotinaldehyde (IIa-8) (500 mg, 3.18 mmol) in acetonitrile (20 mL) at 0° C. under nitrogen was added a solution of 2,2,2-trifluoroethyl amine hydrochloride (1.7 g, 12.7 mmol) in triethylamine (0.5 mL) and the reaction mixture was allowed to warm to rt and stirred for a further 48 h. The reaction mixture was then concentrated in vacuo to give 1.2 g of the title compound (II-8) as a crude oil which was used in the next step without further purification.

3-(6-(Difluoromethyl)pyridin-3-yl)-1-oxo-2-(2,2,2-trifluoroethyl)-1,2,3,4-tetrahydroisoauinoline-4-carboxylic Acid (Intermediate of Formula (TUI-8))

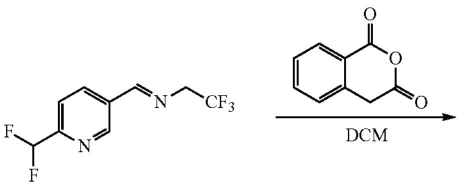

(II-8)

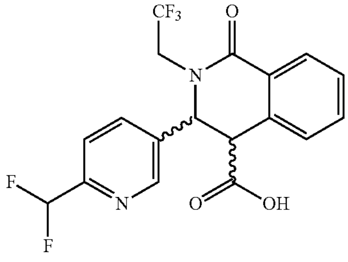

(III-8)

To a stirred solution of crude (E)-1-(6-(difluoromethyl) pyridin-3-yl)-N-(2,2,2-trifluoroethyl)methanimine (II-8) (1.2 g, 5.2 mmol) in dichloromethane (15 mL) at rt under nitrogen was added homophthalic anhydride (0.87 g, 5.2 mmol) and the reaction mixture was allowed to stir for 16 h. The reaction mixture was then concentrated in vacuo to give 2.1 g of the crude title compound (III-8) as an approximate 1:1 mixture of cis and trans isomers which was used in the next step without further purification. LCMS (Formic acid: $CH_3CN$): m/z: MH+401, $R_t$=1.52 min.

(3S,4S)—N-(3-cyano-4-fluorophenyl)-3-(6-(difluoromethyl)pyridin-3-yl)-1-oxo-2-(2,2,2-trifluoroethyl)-1,2,3,4-tetrahydroisoquinoline-4-carboxamide (8a) (Compound of Formula (I) wherein X is CH and R is $CHF_2$)

To a stirred solution of crude 3-(6-(difluoromethyl)pyridin-3-yl)-1-oxo-2-(2,2,2-trifluoroethyl)-1,2,3,4-tetrahydroisoquinoline-4-carboxylic acid (III-8) (1.0 g, 2.5 mmol) in pyridine (10 mL) at rt under nitrogen was added propylphosphonic anhydride (50% solution in ethyl acetate, 15.0 ml, 25.0 mmol) followed by 5-amino-2-fluorobenzonitrile (0.45 g, 3.25 mmol) and the reaction heated to 50° C. for 16 h. The reaction mixture was then cooled to rt, diluted with ethyl acetate (50 mL), washed with $CuSO_4$ solution (3×10 mL), dried ($MgSO_4$), filtered and the filtrate concentrated in vacuo.

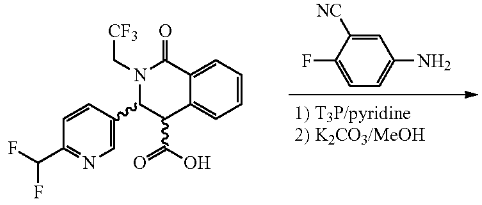

(III-8)

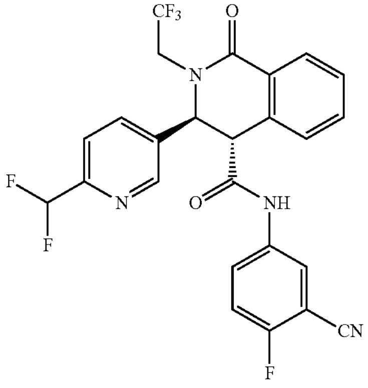

(8a)

The resulting oil was diluted with MeOH (50 mL) and stirred with $K_2CO_3$ (2.0 g, 14.5 mmol) for 4 h during which time the trans epimer was formed exclusively, according to NMR. The suspension was then filtered through a bed of celite, concentrated in vacuo and the resulting oil subjected to chromatography ($SiO_2$, 3:7 ethylacetate:hexane) to give the title compound (8) as a racemate (400 mg, 0.77 mmol, 31%). The (+)-enantiomer was obtained by preparative chiral HPLC (column: Chiralpak IA, 21×250 mm, 5μ. particle size, operating at ambient temperature and flow rate of 21 ml/min. Wave length: 222 nm, run time 20 min. Mobile phase: Hexane/Dichloromethane/EtOH:70/15/15), followed by lyophilization to give 197 mg of the title compound (8a) as an off-white solid >99% e.e. $^1$H NMR (400 MHz, DMSO-d6): δ 10.84 (s, 1H), 8.61 (s, 1H), 8.06-8.00 (m, 2H), 7.85-7.83 (m, 1H), 7.68-7.46 (m, 5H), 7.28 (d, J=7.48 Hz, 1H), 7.03-6.75 (m, 1H), 5.59 (s, 1H), 4.65-4.59 (m, 1H), 4.32 (s, 1H), 4.17-4.10 (m, 1H). LCMS (Ammonium acetate: $CH_3CN$): m/z: MH+519, Rt=2.66 min in 5 mins run. $[\alpha]D^{25}$=+49.28° (c=0.303, dichloromethane).

Synthesis of (3S,4S)—N-(3-cyano-4-fluorophenyl)-1-oxo-2-(2,2,2-trifluoroethyl)-3-(2-(trifluoromethyl)pyrimidin-5-yl)-1,2,3,4-tetrahydroisoquinoline-4-carboxamide (9a) (E)-N-(2,2,2-trifluoroethyl)-1-(2-(trifluoromethyl)pyrimidin-5-yl)methanimine (Intermediate of Formula (IIa-9))

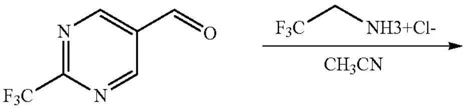

(IIa-9)

-continued

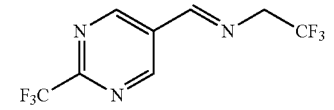

(II-9)

To a stirred solution of 2-(trifluoromethyl)pyrimidine-5-carbaldehyde (IIa-9) (1.0 g, 5.7 mmol) in acetonitrile (20 mL) at 0° C. under nitrogen was added a solution of 2,2,2-trifluoroethyl amine hydrochloride (2.25 g, 22.7 mmol) in triethylamine (0.5 mL). The reaction was allowed to warm to rt then stirred for a further 48 h. The reaction mixture was then concentrated in vacuo to give 1.46 g of the crude title compound (II-9) which was used in the next step without further purification.

1-Oxo-2-(2,2,2-trifluoroethyl)-3-(2-(trifluoromethyl) pyrimidin-5-yl)-1,2,3,4-tetrahydroisoquinoline-4-carboxylic Acid (Intermediate of Formula (III-9))

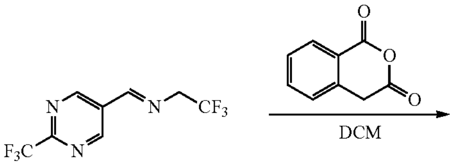

(II-9)

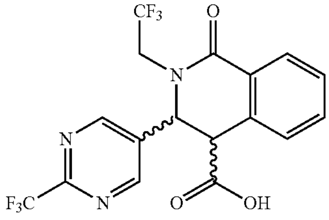

(III-9)

To a stirred solution of crude (E)-N-(2,2,2-trifluoroethyl)-1-(2-(trifluoromethyl)pyrimidin-5-yl)methanimine (II-9) (1.46 g, 4.3 mmol) in dichloromethane (15 mL) at rt under nitrogen was added homophthalic anhydride (920 mg, 5.67 mmol). After 16 h the reaction was concentrated in vacuo to give 2.3 g of the crude title compound (III-9) as an approximate 1:1 mixture of cis and trans isomers which was used in the next step without further purification. LCMS (Formic acid:$CH_3CN$): m/z: MH+420, $R_t$=1.68 min.

(3S,4S)—N-(3-cyano-4-fluorophenyl)-1-oxo-2-(2,2,2-trifluoroethyl)-3-(2-(trifluoromethyl) pyrimidin-5-yl)-1,2,3,4-tetrahydroisoquinoline-4-carboxamide (9a) (Compound of Formula (I) wherein X is N and R is $CF_3$)

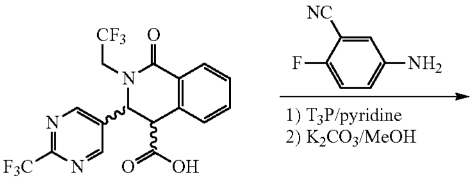

(III-9)

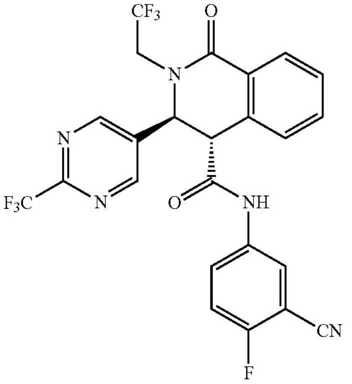

(9a)

To a stirred solution of crude 1-oxo-2-(2,2,2-trifluoroethyl)-3-(2-(trifluoromethyl)pyrimidin-5-yl)-1,2,3,4-tetrahydroisoquinoline-4-carboxylic acid (III-9) (1.95 g, 4.65 mmol) in pyridine (30.0 ml) at rt was added propylphosphonic anhydride (50% solution in ethyl acetate, 29.6 ml, 46.5 mmol) followed by 5-amino-2-fluorobenzonitrile (0.8 g, 6.05 mmol) and the reaction heated to 50° C. for 16 h. The reaction mixture was then cooled to rt, diluted with ethyl acetate (50 mL), washed with $CuSO_4$ solution (3×10 mL), dried ($MgSO_4$), filtered and the filtrate concentrated in vacuo. The resulting oil was diluted with MeOH (20 mL) and stirred with $K_2CO_3$ (1.0 g, 7.3 mmol) for 4 h during which time the trans epimer was formed exclusively, according to NMR. The suspension was then filtered through a bed of celite, concentrated in vacuo and the resulting oil subjected to chromatography ($SiO_2$, 3:7 ethylacetate:hexane) to give the title compound (9) as a racemate (1.2 g, 2.23 mmol, 48%). The (+)-enantiomer was obtained by preparative chiral HPLC (column: Chiralpak IA, 21×250 mm, 5μ particle size, operating at ambient temperature and flow rate of 21 ml/min. Wave length: 222 nm, run time 20 min. Mobile phase: Hexane/Dichloromethane/EtOH:70/15/15), followed by lyophilization to give 410 mg of the title compound (9a) as an off-white solid >99% e.e. $^1$H NMR (400 MHz, DMSO-d6): δ 10.84 (s, 1H), 8.86 (s, 2H), 8.05-8.01 (m, 2H), 7.84-7.82 (m, 1H), 7.57-7.47 (m, 3H), 7.33 (d, J=6.88 Hz, 1H), 5.69 (s, 1H), 4.73-4.65 (m, 1H), 4.41 (s, 1H), 4.18-4.07 (m, 1H). LCMS (Formic acid:$CH_3CN$): m/z: MH+536, Rt=1.84 min. [α]D$^{25}$=+27.12° (c=0.47, dichloromethane).

Example 2: In-Vitro Potency Against *P. falciparum* (3D7 Strain)

Cultures of the widely-used malaria reference strain of chloroquine-sensitive *Plasmodium falciparum* (3D7) were maintained in a 1.25% suspension of human red blood cells cultured in RPMI 1640 medium (pH 7.3) supplemented with 0.5% Albumax II (Gibco Life Technologies, San Diego, CA), 12 mM sodium bicarbonate, 0.2 mM hypoxanthine, and 20 mg/L gentamicin at 37° C., in an atmosphere of 1% $O_2$, 3% $CO_2$ with a balance of nitrogen (*Human malaria parasites in continuous culture*. Trager W et al., 1976, *Science,* 193: 673-675). Growth inhibition was quantified using a fluorescence assay utilising the binding of SYBR Green (*Novel, rapid, and inexpensive cell-based quantification of antimalarial drug efficacy*. Bennett T. N. et al., 2004, *Antimicrob. Agents Chemother.,* 48: 1807-1810) to double stranded DNA, which emits a fluorescent signal at 528 nm after excitation at 485 nm. Mefloquine was used as a drug control to monitor the quality of the assay (Z'=0.6 to 0.8, where Z' is a measure of the discrimination between the positive and negative controls on a screen plate). Hits were confirmed by full-potency curves with dose-response curves determined from a minimum of 3 independent experiments. Compound bioactivity was expressed as $EC_{50}$, the effective concentration of compound causing 50% parasite death. All data were processed using IDBS ActivityBase. Raw data was converted into percent inhibition through linear regression by setting the high inhibition control as 100% and the no inhibition control as 0%. Quality control criteria for passing plates were as follows: z'>0.5, S:B>3, % $CV_{(no\ inhibition\ control)}$<15. The formula used to calculate z' is $$1 - \frac{3 \times (\text{StDev\_high} + \text{StDev\_low})}{\text{ABS}(\text{Mean\_high} - \text{Mean\_low})}.$$

Curve fitting was carried out using the following 4 parametric equation:

$$y = A + \frac{B - A}{1 + (C/x)^D},$$

where A=% inhibition at bottom, B=% inhibition at top, C=$EC_{50}$, D=slope, x=inhibitor concentration and y=% inhibition. If curve definition was poor, B was fixed to 100. The data are presented in Table 1 below:

TABLE 1

| Compound | 3D7 $EC_{50}$(nM) |
|---|---|
| (1a) | 19 nM |
| (2) | 80 nM* |
| (3a) | 70 nM |
| (4a) | 53 nM |
| (5a) | 40 nM |
| (6a) | 68 nM |
| (7a) | 68 nM |
| (8a) | 59 nM |
| (9a) | 103 nM |
| (+) SJ-733, (3S,4S)-N-(3-cyano-4-fluoro-phenyl)-1-oxo-3-(pyridin-3-yl)-2-(2,2,2-trifluoro-ethyl)-1,2,3,4-tetrahydro-isoquinoline-4-carboxamide (comparative compound not from the invention) | 145 nM |

Note:
Compounds indicated with * are trans-racemic.

These data show that the compounds of the invention are able to inhibit the growth of the asexual intraerythrocytic stage of *Plasmodium falciparum*: at a half-maximal concentration (i.e. $IC_{50}$) which is significantly lower than that of the reference compound (+) SJ-733. Moreover, potency is predominantly associated with the dextrorotatory, i.e. (+) enantiomer.

Example 3: Anti-Malarial In Vivo Efficacy of Compounds According to the Invention in NSG SCID Mice In-vivo efficacy was measure against *P. falciparum* Pf3D70087/N9 (*A Murine Model of falciparum-Malaria by In Vivo Selection of Competent* Strains *in Non-Myelodepleted Mice Engrafted with Human Erythrocytes*. Angulo-Barturen I. et al., 2008, *Plos One.,* 3(5):e2252) in female NOD-scid IL-2Rγnull mice (NSG) (purchased from Charles River, France) engrafted to have a minimum of 40% of human erythrocytes (*Improved Murine Model of Malaria Using Plasmodium falciparum Competent Strains and Non-Myelodepleted NOD-scid IL2Rγnull Mice Engrafted with Human Erythrocytes*. Jiménez-Diaz M. B. et al., 2009, *Antimicrob Agents Chemother.,* 53(10): 4533-4536) (Basque Center of Transfusion and Human Tissues, Galdakao, Spain, Centro de Transfusiones de la Comunidad de Castilla y León, Valladolid, Spain and Bank of Blood and Tissues, Barcelona, Spain), and in intravenously infected parasitized human erythrocytes 72 h before drug treatment inception. Treatment started on Day 1 of the study, when the mice reached an average parasitemia of approximately 1% (PO). Compounds were administered orally as formulations in 1% Hydroxypropyl-Cyclodextrin, 40% PEG-400, 10% Propylenglycol, 10% Ethanol, 40% PBS, at 10 ml/kg bodyweight, either at a single dose of 10 mg/kg bodyweight or in a daily dose of 1 mg/kg body weight over 4 days. Parasitemia in peripheral blood was assessed every 24 h by flow cytometry (Attune NxT Acoustic Focusing Flow Cytometer (InvitroGen)), using TER-119-Phycoerythrine monoclonal antibody as a marker of murine erythrocytes and SYTO-16, non-selective fluorescent nucleic acid dye to detect intraerythrocytic parasites, as previously described (*Quantitative measurement of Plasmodium-infected erythrocytes in murine models of malaria by flow cytometry using bidimensional assessment of SYTO-*16 *fluorescence*. Jiménez-Diaz M. B. et al., 2009, *Cytometry A.,* 75(3):225-35). The therapeutic efficacy was estimated as the percentage of growth inhibition compared to untreated mice after one (% inhibition at Day 3) or two (% inhibition at Day 5) cycles of parasite replication. Data analysis was performed using GraphPad Prism 7.0 (GraphPad Software). Samples of peripheral blood (25 μl) were continuously taken during the study after the first dosing, mixed with 25 μl of $H_2O$ MilliQ and immediately stored −80° C. until analysis. The drugs were extracted from 10 μl of lysates obtained by protein precipitation of blood samples using standard liquid-liquid extraction methods. The samples are analyzed by LC-MS/MS for quantification in a Waters Micromass UPLC-TQD (Waters, Manchester, UK). Blood concentration vs time was analyzed by non-compartmental analysis (NCA) using Phoenix WinNonlin vers.7.0 (Certara) or R or Excel (Microsoft), from which exposure-related values (tmax, Cmax and AUC0-t) were estimated. Treated mice that reached the limit of detection by standard flow cytometry (<0.01% from total circulating erythrocytes) were maintained until day 60 of the study with a chimerism >50% of total circulating erythrocytes. During the follow up period, Parasitemia in peripheral blood was assessed every 2 or 3 days and analyzed by flow cytometry with a limit of quantification of 0.01%. Day of recrudescence (DoR) was estimated by linear interpolation of % parasitemia the day before the rise to PO and the % parasitemia the day after reaching PO. Mice were deemed cured if they were free of detectable parasite in peripheral blood by flow cytometry at 0.01% limit of quantification by day 60 of the study. DoR was only computed for parasites showing growth kinetics in blood comparable to the initial infection.

Altogether, those data support that the compounds of the invention clearly have exposure as required for a malarial drug via the oral route and that the antimalarial efficacy is significantly improved compared to the reference compound (+) SJ-733.

Example 4: Determination of In-Vitro Toxicity Against Mammalian HepG2 Cells

Actively growing HepG2 human cells (85011430, European Collection of Authenticated Cell Cultures) were detached from the culture surface with trypsin and counted using a Cellometer (Nexcelom). Then, 12 ml of culture per plate required were prepared at a density of $1.0\times10^5$ cells per ml using Minimum Essential Medium (41090, Gibco Life Technologies) supplemented with 10% foetal bovine serum (10106-169, Gibco Life Technologies) and 1% NEAA solution (11140-035, Gibco Life Technologies). Cells were seeded (25 µl per well) in 384-well plates (781098, Greiner) with prestamped compounds and controls (DMSO and Doxorubicin 50 µM) (125 nl per well) using a WellMate dispenser (Thermo Scientific). Cells were incubated at 37° C. and 5% $CO_2$ in a humidified incubator for 48 h. After incubation, 5 µl of Resazurin (R7017, Sigma) per well (45 µM final concentration) were added and plates were kept at 37° C. for 3.5-4 h. Plates were then read on Pherastar LS plate reader (BMG) and percentage of inhibition for each test compound was calculated using the equation: % Inhibition=100−(((Test compound−Blank)/(DMSO control−Blank))×100). Toxicity $IC_{50}$'s were calculated using ActivityBase templates.

Example 5: Determination of Microsomal Intrinsic Clearance ($Cl_{int}$) and Hepatocycte Intrinsic Clearance ($Cl_{int}$)

The compounds of the invention (1 µM) were incubated in suspension with human (rat or mouse) liver microsomes pooled from multiple donors (>10) and samples taken at 5 time points over the course of a 45 min experiment and analysed by LC MS/MS. Microsomes (final protein concentration 0.5 mg/mL), 0.1 M phosphate buffer pH 7.4 and test compound (final substrate concentration 1 µM; final DMSO concentration 0.25%) were pre-incubated at 37° C. prior to the addition of NADPH (final concentration 1 mM) to initiate the reaction. A minus cofactor control incubation was included for each compound tested where 0.1 M phosphate buffer pH 7.4 is added instead of NADPH (minus NADPH). All incubations were performed in duplicate for each test compound and the results averaged. Each compound is incubated for 0, 5, 15, 30 and 45 min. The control (minus NADPH) was incubated for 45 min only. The reactions were stopped by transferring incubate into acetonitrile at the appropriate time points, in a 1:3 ratio.

The termination plates were centrifuged at 3,000 rpm for 20 min at 4° C. to precipitate the protein. Following protein precipitation, the sample supernatants were combined in cassettes of up to 4 compounds, internal standard added and samples analysed by LC-MS/MS. From a plot of ln peak area ratio (compound peak area/internal standard peak area) against time, the gradient of the line is determined. Subsequently, half-life (t½) and intrinsic clearance (CLint) are calculated using the equations below:

$$\text{Elimination rate constant } (k)=(-\text{gradient})$$

$$\text{Half-life } (t_{1/2})(\text{min})=0.693/k$$

$$\text{Intrinsic clearance (i.e. } CL_{int})(\mu\text{L/min/mg protein})=V\times0.693/t_{1/2}$$

where V=Incubation volume (µL)/Microsomal protein (mg)

Verapamil and dextromethorphan were included in the assay as controls and if the values for these compounds were not within the specified limits the results were rejected and the experiment repeated.

Determination of Hepatocycte Intrinsic Clearance ($Cl_{int}$).

The compounds of the invention (3 µM) were incubated in suspension with cryopreserved human (rat or mouse) hepatocytes pooled from multiple donors (>10) and samples taken at 6 time points over the course of a 60 min experiment and analysed by LC MS/MS. Williams E media supplemented with 2 mM L-glutamine and 25 mM HEPES and test compound (final substrate concentration 3 µM; final DMSO concentration 0.25%) were pre-incubated at 37° C. prior to the addition of a suspension of cryopreserved hepatocytes (final cell density 0.5×106 viable cells/mL in Williams E media supplemented with 2 mM L glutamine and 25 mM HEPES) to initiate the reaction. The final incubation volume is 500 µL. The reactions are stopped by transferring aliquots of incubate into acetonitrile at the appropriate time points, in a 1:2 ratio. The termination plates are centrifuged at 3,000 rpm for 20 min at 4° C. to precipitate the protein. Following protein precipitation, the sample supernatants were combined in cassettes of up to 4 compounds, internal standard was added and analysed by LC MS/MS. From a plot of ln peak area ratio (compound peak area/internal standard peak area) against time, the gradient of the line was determined. Subsequently, half-life (t½) and intrinsic clearance (CLint) were calculated using the equations below:

$$\text{Elimination rate constant } (k)=(-\text{gradient})$$

$$\text{Half-life } (t½)\ (\text{min})=0.693/k$$

$$\text{Intrinsic clearance (i.e. } CL_{int})\ (\mu\text{L/min/million cells})=V\times0.693/t_{1/2}$$

where V=Incubation volume (µL)/Number of cells

Verapamil and umbelliferone were included in the assay as controls and if the values for these compounds are not within the specified limits the results were rejected and the experiment repeated. The in-vitro and in-vivo pharmacokinetic parameters are presented in Table 2 below:

TABLE 2

| Compound | Intrinsic microsomal clearance (mouse, rat, human) µL/min/mg protein | Intrinsic hepatocyte clearance (human) µL/min/$10^6$ cells | PK parameters (mouse) | PK parameters (rat) |
|---|---|---|---|---|
| (1a) | <10, <10, <3 | <3.0 | Cl = 0.13 L/h/Kg $t_{1/2}$ = 17 h F = 79% | Cl = 0.06 L/h/Kg $t_{1/2}$ = 26 h F = 107% |

TABLE 2-continued

| Compound | Intrinsic microsomal clearance (mouse, rat, human) µL/min/mg protein | Intrinsic hepatocyte clearance (human) µL/min/$10^6$ cells | PK parameters (mouse) | PK parameters (rat) |
|---|---|---|---|---|
| (2)* | nd, nd, 13 | nd | n/d | n/d |
| (3a) | <10, <10, 6 | <10.0 | Cl = 0.10 L/h/Kg $t_{1/2}$ = 11 h F = 95% | Cl = 0.04 L/h/Kg $t_{1/2}$ = 11 h F = 95% |
| (4a) | <10, <10, <3 | <3.0 | Cl = 0.16 L/h/Kg $t_{1/2}$ = 41 h F = 56% | Cl = 0.03 L/h/Kg $t_{1/2}$ = 85 h F = 33% |
| (6a) | <10, nd, <3 | <3.0 | n/d | n/d |
| (7a) | <10, nd, <3 | <10.0 | Cl = 0.16 L/h/Kg $t_{1/2}$ = 18 h F = 108% | Cl = 0.09 L/h/Kg $t_{1/2}$ = 38 h F = 108% |
| (8a) | <10, nd, <3 | 4.0 | Cl = 0.2 L/h/Kg $t_{1/2}$ = 56 h F = 37% | n/d |
| (9a) | 10.1, <10, <3 | <3.0 | Cl = 0.19 L/h/Kg $t_{1/2}$ = 14 h F = 92% | Cl = 0.08 L/h/Kg $t_{1/2}$ = 22 h F = 65% |
| (+) SJ-733 (comparative compound) | 37, <6, 140 | 11.4 | Cl = 4.2 L/h/Kg $t_{1/2}$ = 1.1 h F = 66% | Cl = 0.8 L/h/Kg $t_{1/2}$ = 7.7 h F = 75% |

Note:
PK in mouse was determined at 10 mg/kg (IV; intra-venous) and 10 mg/kg (PO; per os). PK in rat was determined at 1 mg/kg (IV) and 3 mg/kg (PO). Clearance (Cl) and half-life ($t_{1/2}$) are derived from the IV arm. Data indicated with an asterisk are for the trans-racemic compound, n/d is not determined.

Taken together, these data support that the compounds of the invention clearly have exposure as required for a malarial drug via the oral route. Furthermore, the in-vitro metabolic stability is improved compared to the reference compound (+) SJ-733. Furthermore, the in-vivo half-lives in mouse and rat species are significantly improved compared to the reference compound (+) SJ-733, consistent with the improved in-vitro stability in microsome and hepatocyte incubations. Furthermore, the compound of example (1a) has an improved pharmacokinetic profile in dog species compared to the reference compound; i.e. compound (1a): (IV at 1 mg/kg, Cl=0.26 mL/min/Kg, t½=41 h) compared to (+) SJ-733 (IV at dose, 3 mg/kg, Cl=3 mL/min/Kg, t½=10 h).

Example 6: Determination of PK Parameters in Mouse/Rat

Swiss Albino male mice or Sprague Dawley rats (TCGLS, India) were kept under a 12/12 h light/dark cycle, 22±2° C. temp, 50±20% RH with free access to food and water ad libitum. Mice were selected randomly/based on body weight/age and fasted for 4 h before dosing and until 2 h after dosing. Three mice were used per route of administration. For IV determination (1 mg/kg, dose volume 5 ml/kg) the dose was administered by injection into the lateral tail vein (rats are anaesthetized using 3% v/v isoflurane: oxygen mixture). For PO determination (3 mg/kg, dose volume 10 ml/kg) the dose was administered by oral gavage in conscious animals.

Blood samples were taken (mice 50 µL, rat 100 µL) at regular timepoints from the saphenous vein (conscious restrained animals) and collected into heparinized capillary tubes and transferred into 0.5 mL microcentrifuge tubes. Samples were processed by centrifugation at 1640 g for 10 min at +4° C. within 30 min of collection and stored at −20° C. until bioanalysis. All samples were mixed with ice-cold acetonitrile containing an internal standard, centrifuged at 4000 rpm for 15 min at 15° C. Supernatant was then half diluted in water and analysed by LCMS/MS analysis to determine analyte peak area/IS peak area (the ratio). Concentration (plasma) of the compounds of the invention was determined by reference to a calibration curve. Pharmacokinetic parameters (Cmax, Tmax, AUC, $t_{1/2}$, CL, Vd, BA) were calculated using WinNonLin, using non-compartmental analysis (Phoenix, Version 6.3). The pharmacokinetic parameters for compounds shown in Table 2 support that compounds of the invention have pharmacokinetic properties associated with treatment of malaria via the oral route and that compounds have substantially longer half-lives than the reference compound.

Example 7: Determination of the Effect of Compounds of the Invention on Cytosolic [Na+] in Saponin-Isolated *Plasmodium falciparum* (Dd2 Strain)

Figure 4:
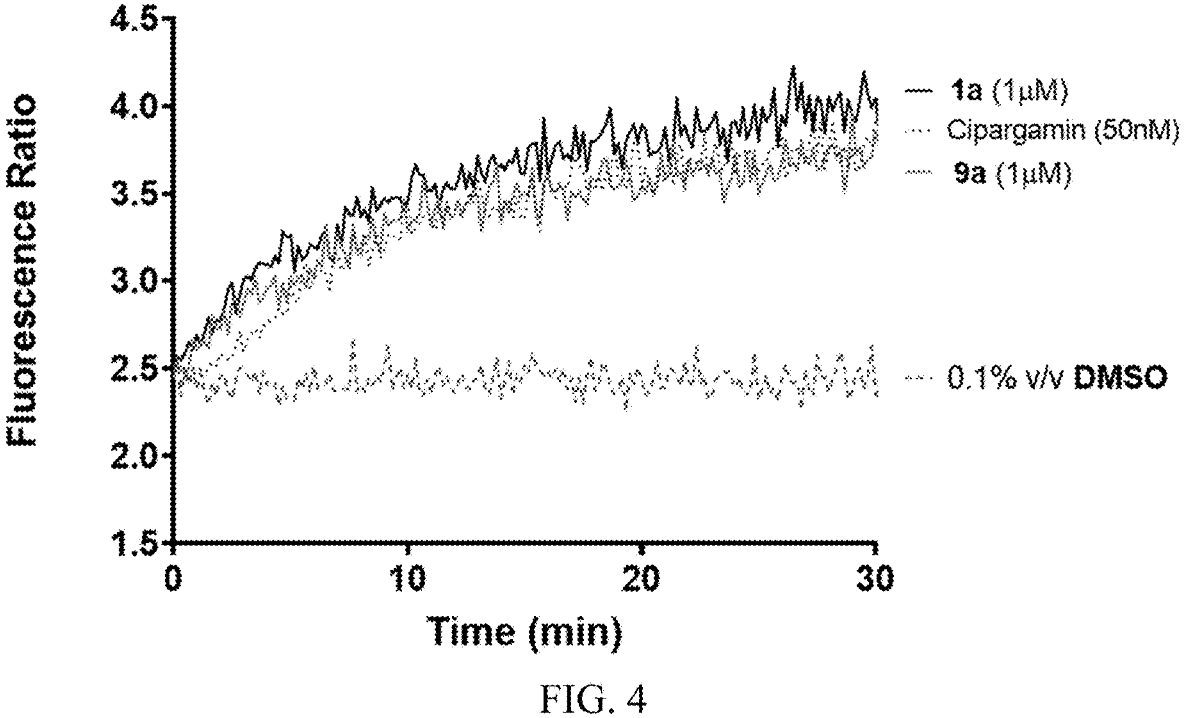
FIG. 4 represents the effect of compounds on cytosolic [Na+] in *Plasmodium falciparum* 3D7 strain following treatment with compounds of the invention (1a) and (9a) compared to positive control (Cipargamin, KAE609) and negative control (DMSO), as described in Example 7.

The ability of compounds of the invention to function as inhibitors of the Na+/H+-ATPase, which regulates parasite cytosolic sodium concentration has been tested in the following assay. Their effect on cytosolic sodium can be measured using a sodium flux assay (*Biochemical characterization and chemical inhibition of PfATP$_4$-associated Na+-ATPase activity in Plasmodium falciparum membranes*. Rosling J. E. O. et al., 2018, *J. Biol. Chem.,* 293: 13397). Saponin-isolated parasites at a density of 1.4-1.8×$10^8$ cells/mL, were suspended in bicarbonate-free RPMI1640 supplemented with 20 mM D-glucose, 0.2 mM hypoxanthine, 25 mM HEPES and 25 mg/L gentamycin sulfate (pH 7.10), then treated with sodium-binding benzofuran isophthalate acetoxymethyl ester (5.5 mM) and Pluronic F-127 (0.01% w/v) for 20 min at 37° C. The dye-loaded cells were washed twice (12,000 g, 0.5 min) in bicarbonate-free RPMI then incubated for a further 20 min at 37° C. to allow for complete de-esterification of the dye before being resuspended at a final cell concentration of 1.5-2.5×$10^7$ cells/mL in standard saline. Immediately following treatment with test compound (5 mM) or vehicle control (0.1% v/v DMSO), the dye-loaded cells were excited at 340 nm and 380 nm and fluorescence measurements recorded at 490 nm, every 15-45 s. [Na+] was determined according to reference to a calibration curve of the 340/380 nm fluorescence ratio as described previously (*In situ calibration and* [*H*+] *sensitivity of the fluorescent Na+ indicator SBFI*. Diarra A. et al., 2001, *Am. J. Physiol. Cell Physiol.,* 280: 1623). FIG. 4 shows the effect on intracellular [$Na^+$] in SBFI-loaded 3D7 parasites suspended in standard saline following treatment with compound (1a) and (9a) at 1 µM concentration, compared to cipargamin at 50 nM and DMSO control. The data indicate that the increase of cytosolic sodium concentration following treatment with compound is consistent with inhibition of the Na*ATPase (i.e. PfATP-4).

Altogether, those data support improved potency against *Plasmodium falciparum* and enhanced metabolic stability of compounds of the invention in mouse, rat and human microsomes and human hepatocytes, which translates to longer half-lives in mouse and rat and therefore enhanced efficacy in the mouse malaria model. The combined effects of enhancements in these parameters would be expected to be a significant reduction in the predicted single human dose, compared to (+) SJ-733.

Figure 5:
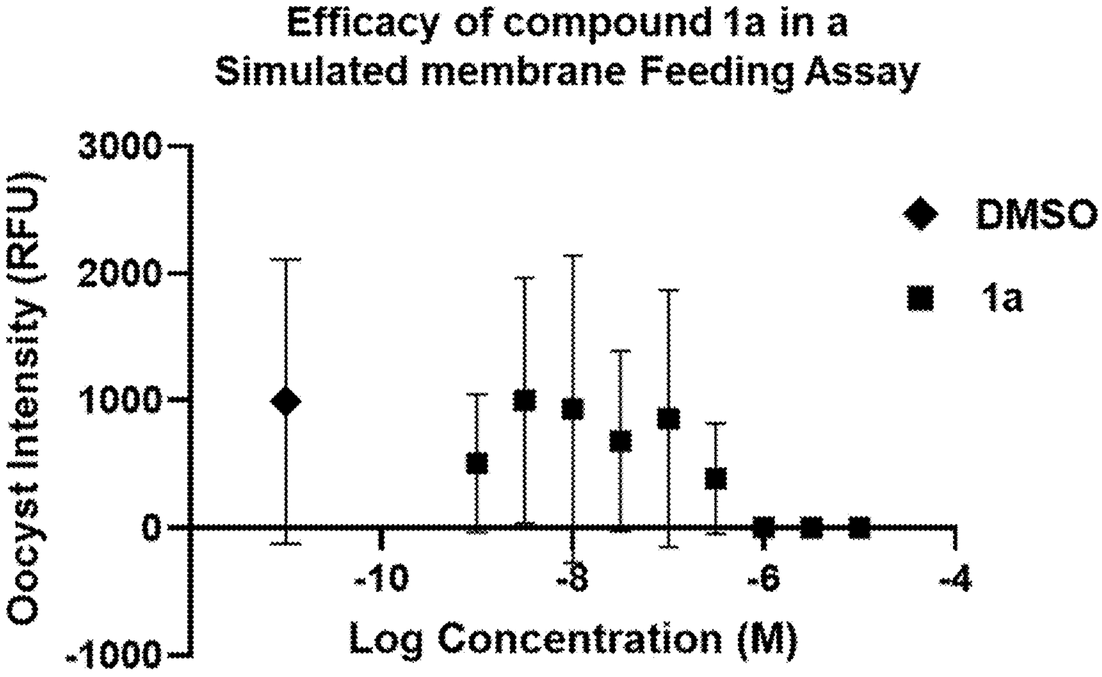
FIG. 5 represents the effect of compound (1a) on the transmission of *P. falciparum* from infected blood into A. Stefensi mosquitos, as determined by the number of oocysts in the mosquito midgut ($IC_{50}$=323 nM), as described in Example 8.

Example 8: Determination of Transmission-Blocking Potential Using a Standard Membrane Feeding Assay Standard Membrane Feeding Assays (SMFA) were performed using *P. falciparum* transgenic reporter strain NF54-HGL that expresses a firefly luciferase gene from an hsp70 promoter (Vos et al., 2015, *Scientific Reports,* 5). Stage V gametocytes were pre-incubated with test compound prior to mosquito feeding. Test compound is dissolved in DMSO to achieve a stock solution of 10 mM that was serially diluted in DMSO to achieve concentrations 1000-fold above the final test concentration. Subsequently, 10 µl of diluted compound in DMSO is then added to 990 µl pre-warmed RPMI 1640 medium supplemented with 367 µM hypoxanthine, 25 mM HEPES and 25 mM $NaHCO_3$ ('incomplete medium'). 40 µl of this intermediate dilution is added to 360 µl of parasite culture and incubated for 48 hrs at 37° C. in Eppendorf tubes, resulting in 0.1% final DMSO concentration. Hereafter, 300 µl of the gametocyte culture/compound mix is added to 180 µl of packed red blood cells and centrifuged for 20 seconds at 10,000×g. After carefully aspirating the supernatant, 200 µl of human serum type A is then added to the pellet. Finally, 300 µl of this mix is immediately injected into an individual membrane covered mini-feeder, where 50 female *A. stephensi* mosquitoes are allowed to feed for 10 minutes. Unfed and partially fed mosquitoes are then removed from the cage within 4 hours after feeding, and fed mosquitoes are maintained at 26° C., 80% humidity. Mosquitoes are processed for luminescence measurements to determine relative oocyst intensities as described previously (Stone et al., 2014, *Journal of Infectious Diseases,* 5, 16). Data is analyzed by fitting a four-parameter logistic regression model using maximum likelihood to find the best fit as described previously (Dechering et al., 2017, *Scientific Reports,* 7, 1) as shown under FIG. 5. These data show that compound (1a) has transmission blocking potential (i.e. transfer of the malaria parasite from human to mosquito).

The invention claimed is:

1. A compound according to Formula (I):

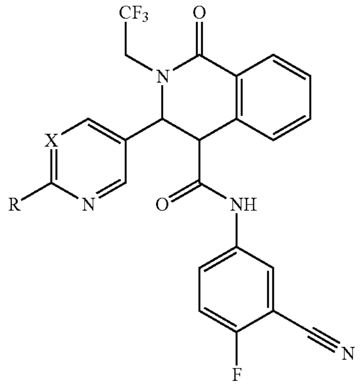

(I)

wherein X is selected from N and CH; when X is CH: R is selected from —$CF_3$, —$CHF_2$, —O-cyclopropyl, —O-isopropyl, —$OCHF_2$, —CN, —$OCH_2CF_3$ and —NH(C═O)$CH_3$; and when X is N: R is —$CF_3$; or a pharmaceutically acceptable salt, hydrate, solvate, tautomer, polymorph, racemic mixture, optically active form, or pharmaceutically active derivative thereof.

2. The compound according to claim 1, wherein X is CH.

3. The compound according to claim 1, wherein X is N.

4. The compound according to claim 1, wherein R is —$CF_3$.

5. The compound according to claim 1, wherein R is O-cyclopropyl.

6. The compound according to claim 1, wherein R is —O-isopropyl.

7. The compound according to claim 1, wherein R is —$OCHF_2$.

8. The compound according to claim 1, wherein R is —CN.

9. The compound according to claim 1, wherein R is —$OCH_2CF_3$.

10. The compound according to claim 1, wherein R is —NH(C═O)$CH_3$.

11. The compound according to claim 1, said compound being selected from the group consisting of:

N-(3-cyano-4-fluorophenyl)-1-oxo-2-(2,2,2-trifluoroethyl)-3-(6-(trifluoromethyl) pyridin-3-yl)-1,2,3,4-tetrahydroisoquinoline-4-carboxamide;

N-(3-cyano-4-fluorophenyl)-3-(6-(difluoromethyl) pyridin-3-yl)-1-oxo-2-(2,2,2-trifluoroethyl)-1,2,3,4-tetrahydroisoquinoline-4-carboxamide;

N-(3-cyano-4-fluorophenyl)-3-(6-cyclo propoxypyridin-3-yl)-1-oxo-2-(2,2,2-trifluoroethyl)-1,2,3,4-tetrahydroisoquinoline-4-carboxamide;

N-(3-cyano-4-fluorophenyl)-3-(6-isopropoxypyridin-3-yl)-1-oxo-2-(2,2,2-trifluoroethyl)-1,2,3,4-tetrahydroisoquinoline-4-carboxamide;

(3-cyano-4-fluorophenyl)-3-(6-(difluoromethoxy) pyridin-3-yl)-1-oxo-2-(2,2,2-trifluoroethyl)-1,2,3,4-tetrahydroisoquinoline-4-carboxamide;

N-(3-cyano-4-fluorophenyl)-3-(6-cyanopyridin-3-yl)-1-oxo-2-(2,2,2-trifluoroethyl)-1,2,3,4-tetrahydroisoquinoline-4-carboxamide;

N-(3-cyano-4-fluorophenyl)-1-oxo-3-(6-(2,2,2-trifluoroethoxy) pyridin-3-yl)-2-(2,2,2-trifluoroethyl)-1,2,3,4-tetrahydroisoquinoline-4-carboxamide;

3-(6-acetamidopyridin-3-yl)-N-(3-cyano-4-fluorophenyl)-1-oxo-2-(2,2,2-trifluoroethyl)-1,2,3,4-tetrahydroisoquinoline-4-carboxamide; and N-(3-cyano-4-fluorophenyl)-1-oxo-2-(2,2,2-trifluoroethyl)-3-(2-(trifluoromethyl) pyrimidin-5-yl)-1,2,3,4-tetrahydroisoquinoline-4-carboxamide, and a pharmaceutically acceptable salt, hydrate, solvate, tautomer, polymorph, racemic mixture, optically active form, or pharmaceutically active derivative thereof.

12. A pharmaceutical formulation containing at least one compound according to claim 1 and a pharmaceutically acceptable carrier, diluent, or excipient.

13. The pharmaceutical composition according to claim 12, said composition further comprising an antimalarial co-agent.

14. The pharmaceutical composition according to claim 13, wherein the co-agent is selected from artemisinin, arthemether, artesunate, dihydroartemisinin, chloroquine, hydroxychloroquine, quinine, quinidine, mefloquine, amodiaquine, a combination of atovaquone and proguanil, clindamycin, doxycycline, lumefantrine, piperaquine, pyronaridine, halofantrine, pyrimethamine-sulfadoxine, primaquine, quinacrine, ferroquine, tafenoquine, arterolane, Spiro [3H-indole-3,1'-[1H]pyrido [3,4-b]indol]-2 (1H)-one, 5,7'-dichloro-6'-fluoro-2',3',4',9'-tetrahydro-3'-methyl-,(1'R,3'S)-]

(Cipargamin, KAE609, CAS Registry Number: 1193314-23-6), 2-(1,1-difluoroethyl)-5-methyl-N-[4-(pentafluoro-$\lambda^6$-sulfanyl) phenyl]-[1,2,4]triazolo [1,5-a]pyrimidin-7-amine (DSM265, CAS Registry Number: 1282041-94-4), Morpholine, 4-[2-(4-cis-dispiro [cyclohexane-1,3'-[1,2,4]trioxolane-5',2"-tricyclo [3.3.1.13,7]decan]-4-ylphenoxy) ethyl]-] (Artefenomel, OZ439, CAS Registry Number: 1029939-86-3), 4-Quinolinecarboxamide, 6-fluoro-2-[4-(4-morpholinylmethyl) phenyl]-N-[2-(1-pyrrolidinyl) ethyl]-(DDD107498, CAS Registry Number: 1469439-69-7), Ethanone, 2-amino-1-[2-(4-fluorophenyl)-3-[(4-fluorophenyl) amino]-5,6-dihydro-8,8-dimethylimidazo [1,2-a]pyrazin-7 (8H)-yl]-(Ganaplacide, KAF-156, CAS Registry Number 1261113-96-5), 5-[4-(Methylsulfonyl) phenyl]-6'-(trifluoromethyl) [3,3'-bipyridin]-2-amine (MMV390048, CAS Registry Number: 1314883-11-8), 4(1H)-Quinolinone, and 6-chloro-7-methoxy-2-methyl-3-[4-[4-(trifluoromethoxy)phenoxy] phenyl]-(ELQ-300, CAS Registry Number: 1354745-52-0).

15. A method for the stereoselective preparation of the enantiomers of a compound of Formula (I) as set forth in claim 1, said method comprising a step of separation of the enantiomers of Formula (III) by stereoselective salt recrystallization with 1-2 equivalents of a chirally pure amine and transforming the specific enantiomers of Formula (III) into the corresponding enantiomer of Formula (I), in presence of an optionally substituted phenylamine

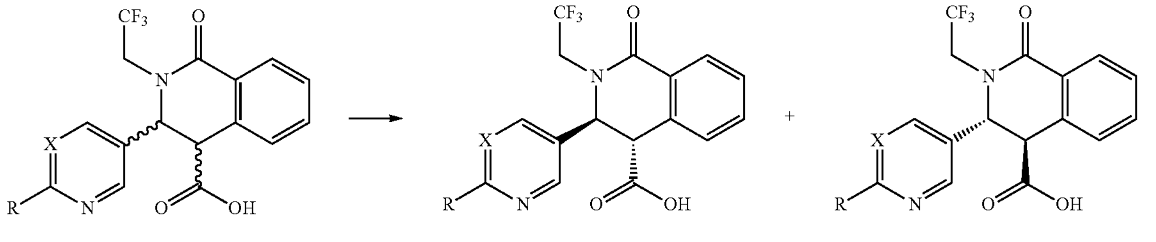

cis,trans - racemate (III)

S,S-(III)

R,R-(III)

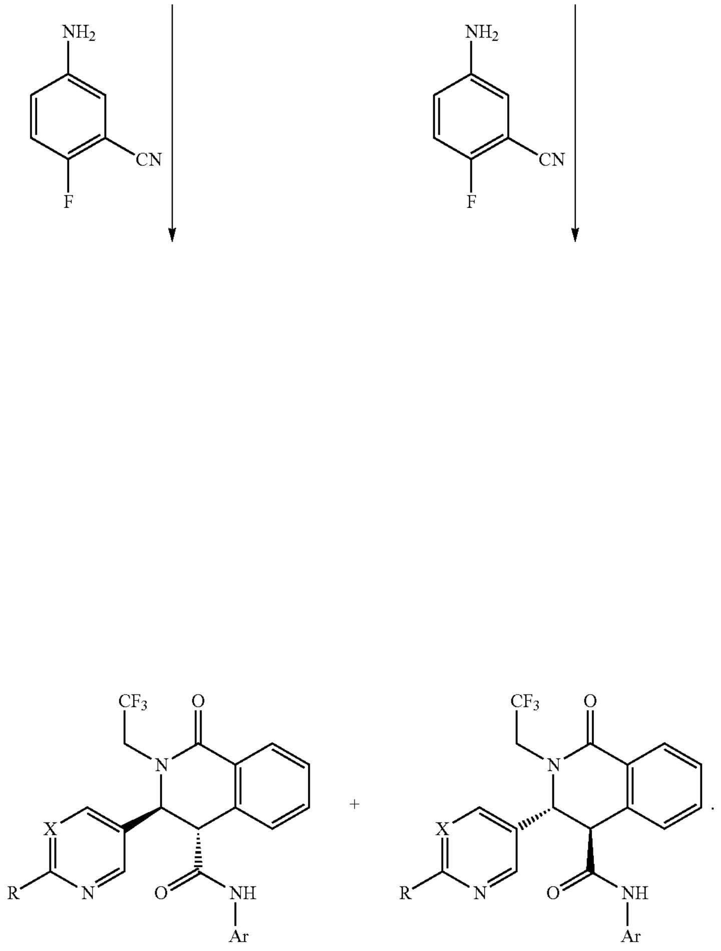

(Ia) (+)-S,S-enantiomer (Ib) (-)-R,R-enantiomer

16. A method for treating malaria in a subject, wherein said method comprises administering a compound according to claim 1 or a pharmaceutically acceptable salt thereof or a pharmaceutically active derivative thereof in a subject in need thereof.

17. An intermediate of Formula (III)

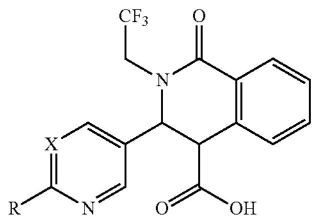

(III)

wherein X is selected from N and CH; when X is CH: R is selected from —$CF_3$, —$CHF_2$, —O-cyclopropyl, —O-isopropyl, —$OCHF_2$, —CN, —$OCH_2CF_3$, and —NH(C═O)$CH_3$; and when X is N: R is —$CF_3$.

18. The intermediate according to claim 17, said intermediate being selected from the group consisting of:

3-(6-cyclopropoxypyridin-3-yl)-1-oxo-2-(2,2,2-trifluoroethyl)-1,2,3,4-tetrahydroisoquinoline-4-carboxylic acid (III-1);

3-(6-methoxypyridin-3-yl)-1-oxo-2-(2,2,2-trifluoroethyl)-1,2,3,4-tetrahydroisoquinoline-4-carboxylic acid (III-2);

1-oxo-2-(2,2,2-trifluoroethyl)-3-(6-(trifluoromethyl) pyridin-3-yl)-1,2,3,4-tetrahydroisoquinoline-4-carboxylic acid (III-3);

1-oxo-3-(6-(2,2,2-trifluoroethoxy) pyridin-3-yl)-2-(2,2,2-trifluoroethyl)-1,2,3,4-tetrahydroisoquinoline-4-carboxylic acid (III-4);

3-(6-acetamidopyridin-3-yl)-1-oxo-2-(2,2,2-trifluoroethyl)-1,2,3,4-tetrahydroisoquinoline-4-carboxylic acid (III-5);

3-(6-cyanopyridin-3-yl)-1-oxo-2-(2,2,2-trifluoroethyl)-1,2,3,4-tetrahydroisoquinoline-4-carboxylic acid (III-6);

3-(6-(difluoromethoxy) pyridin-3-yl)-1-oxo-2-(2,2,2-trifluoroethyl)-1,2,3,4-tetrahydroisoquinoline-4-carboxylic acid (III-7);

3-(6-(difluoromethyl) pyridin-3-yl)-1-oxo-2-(2,2,2-trifluoroethyl)-1,2,3,4-tetrahydroisoquinoline-4-carboxylic acid (III-8); and 1-oxo-2-(2,2,2-trifluoroethyl)-3-(2-(trifluoromethyl) pyrimidin-5-yl)-1,2,3,4-tetrahydroisoquinoline-4-carboxylic acid (III-9).

19. An intermediate of Formula (IV-2)

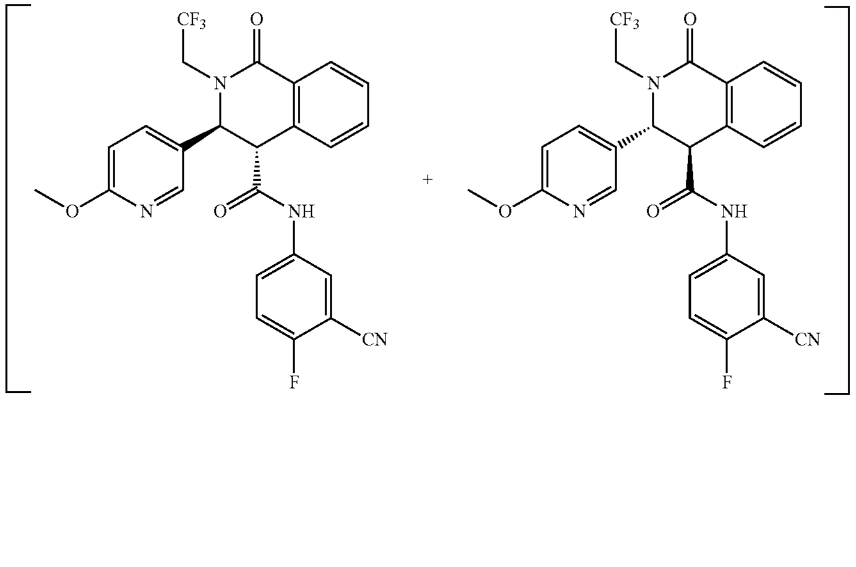

(IV-2), N-(3-cyano-4-fluorophenyl)-3-(6-methoxypyridin-3-yl)-1-oxo-2-(2,2,2-trifluoroethyl)-1,2,3,4-tetrahydroisoquinoline-4-carboxamide or an intermediate of Formula (V-2)

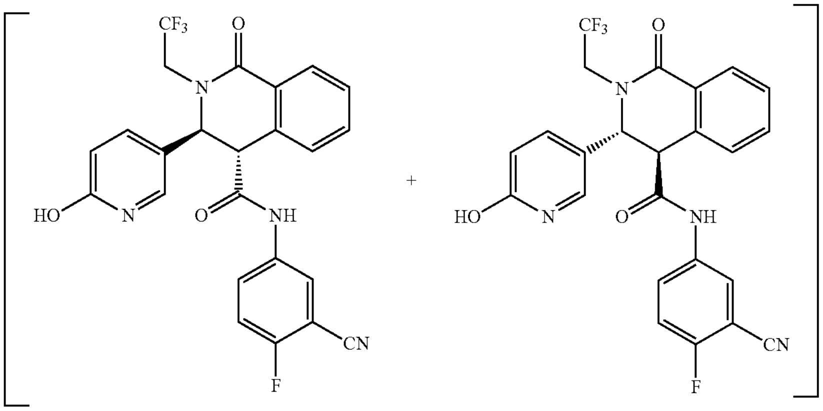

(V-2), N-(3-cyano-4-fluorophenyl)-3-(6-hydroxypyridin-3-yl)-1-oxo-2-(2,2,2-trifluoroethyl)-1,2,3,4-tetrahydroisoquinoline-4-carboxamide.

20. A method of preparation of the stereoselective preparation of an intermediate of Formula (III), said method comprising a step of separation of the enantiomers of Formula (III) by stereoselective salt recrystallization of a compound of Formula (III) with 1-2 equivalents of a chirally pure amine

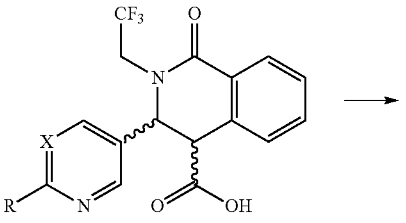

cis,trans - racemate
(III)

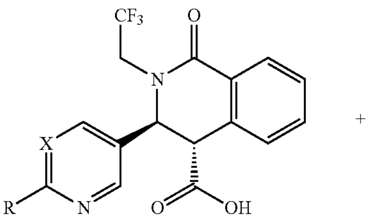

S,S-(III)

-continued
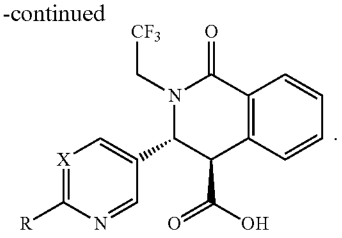
R,R-(III)
* * * * *